(12) United States Patent
Johansson et al.

(10) Patent No.: US 7,691,892 B2
(45) Date of Patent: Apr. 6, 2010

(54) TETRAZOLE COMPOUNDS AND THEIR USE AS METABOTROPIC GLUTAMATE RECEPTOR ANTAGONISTS

(75) Inventors: Martin Johansson, Södertälje (SE); Alexander Minidis, Södertälje (SE); Karin Staaf, Södertälje (SE); David Wensbo, Södertälje (SE); Donald McLeod, Salt Lake City, UT (US); Louise Edwards, Mississauga (CA); Methvin Isaac, Mississauga (CA); Anne O'Brien, Mississauga (CA); Abdelmalik Slassi, Mississauga (CA); Tao Xin, Mississauga (CA); Tomislav Stefanac, Mississauga (CA)

(73) Assignee: AstraZeneca AB, Sodertalje (SE)

( * ) Notice: Subject to any disclaimer, the term of this patent is extended or adjusted under 35 U.S.C. 154(b) by 1160 days.

(21) Appl. No.: 11/060,463

(22) Filed: Feb. 18, 2005

(65) Prior Publication Data

US 2006/0004021 A1 Jan. 5, 2006

Related U.S. Application Data

(60) Provisional application No. 60/545,291, filed on Feb. 18, 2004.

(51) Int. Cl.
*A61K 31/41* (2006.01)
*C07D 257/04* (2006.01)
(52) U.S. Cl. .................................. 514/383; 548/262.2
(58) Field of Classification Search ................. 514/383; 548/262.2
See application file for complete search history.

(56) References Cited

U.S. PATENT DOCUMENTS 4,663,332 A 5/1987 Carson et al.
2007/0197549 A1* 8/2007 Johansson et al. ...... 514/254.05

FOREIGN PATENT DOCUMENTS

| WO | WO-93-02677 A1 | 2/1993 |
|---|---|---|
| WO | WO-01-85705 A1 | 11/2001 |
| WO | WO-03-002559 A2 | 1/2003 |
| WO | WO-03-020721 A1 | 3/2003 |
| WO | WO-03/029210 A2 | 4/2003 |
| WO | WO-03/077918 A1 | 9/2003 |

OTHER PUBLICATIONS

Copending U.S. Appl. No. 10/588,756.*
STN International; file CAPLUS; AN; 2003:396864 (WO 03042188 A1, Jun. 6, 2007.
STN International; file Registry: RN728031-33-2, Jun. 6, 2007.
STN International; file Registry: RN695193-95-4, Jun. 6, 2007.
STN International; file Registry: RN681838-61-9, Jun. 6, 2007.
STN International; file Registry: RN497102-55-3, Jun. 6, 2007.
STN International; file Registry: RN497102-07-5, Jun, 6, 2007.
STN International; file Registry: RN497102-06-4, Jun. 6, 2007.
STN International; file Registry: RN486458-20-2, Jun. 6, 2007.
STN International; file Registry: RN486458-19-9, Jun. 6, 2007.
STN International; file Registry: RN486458-18-8, Jun. 6, 2007.
STN International; file Registry: RN483975-19-5, Jun. 6, 2007.
STN International; file Registry: RN483975-15-1, Jun. 6, 2007.
STN International; file Registry: RN483975-14-0, Jun. 6, 2007.
STN International; file Registry: RN483974-67-0, Jun. 6, 2007.
STN International; file Registry: RN483974-66-9, Jun. 6, 2007.
STN International; file Registry: RN461013-19-4, Jun. 6, 2007.
STN International; file Registry: RN442872-37-9, Jun. 6, 2007.
STN International; file Registry: RN442640-10-0, Jun. 6, 2007.
STN International; file Registry: RN442639-46-5, Jun. 6, 2007.
STN International; file Registry: RN442633-60-5, Jun. 6, 2007.
STN International; file Registry: RN420828-45-1, Jun. 6, 2007.
STN International; file Registry: RN328973-74-6, Jun. 6, 2007.
Schoepp et al., Trends Pharmacol. Sci. 14:13 (1993).
Schoepp, Neurochem. Int. 24:439 (1994).
Pin et al., Neuropharmacology 34:1 (1995).
Bordi and Ugolini, Prog. Neurobiol. 59:55 (1999).
Nakanishi, Neuron 13:1031 (1994).
Knopfel et al., J. Med. Chem. 38:1417 (1995).
Pin et al., PNAS 89:10331 (1992).
Minakami et al., BBRC 199:1136 (1994).
Joly et al., J. Neurosci. 15:3970 (1995).
Baskys, Trends Pharmacol. Sci. 15:92 (1992).
Watkins et al., Trends Pharmacol. Sci. 15:33 (1994).
Bashir et al., Nature 363:347 (1993).
Bortolotto et al., Nature 368:740 (1994).
Aiba et al., Cell 79:365 (1994).
Aiba et al., Cell 79:377 (1994).
Meller et al., Neuroreport 4:879 (1993).

(Continued)

*Primary Examiner*—Golam M M Shameem
*Assistant Examiner*—Susannah Chung
(74) *Attorney, Agent, or Firm*—Birch, Stewart, Kolasch & Birch, LLP

(57) ABSTRACT

The present invention relates to new compounds of formula I,

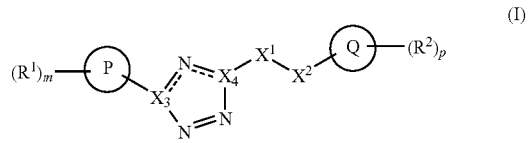

wherein P, Q, $X^1$, $X^2$, $X^3$, $X^4$, $R^1$, $R^2$, m and p, are as defined as in formula I, or, salts, solvates or solvated salts thereof, processes for their preparation and new intermediates used in the preparation thereof, pharmaceutical compositions containing said compounds and to the use of said compounds in therapy.

22 Claims, No Drawings

OTHER PUBLICATIONS

Bordi and Ugolini, Brain Res. 871:223 (2000).
Cunningham et al., Life Sci. 54:135 (1994).
Hollman et al., Ann. Rev. Neurosci. 17:31 (1994).
Spooren et al., Trends Pharmacol. Sci. 22:331 (2001).

Gasparini et al. Curr. Opin. Pharmacol. 2:43 (2002).
Neugebauer Pain 98:1 (2002).
Holloway & Dent (1990) Gastroenterol. Clin. N. Amer. 19, pp. 517-535.

* cited by examiner

TETRAZOLE COMPOUNDS AND THEIR USE AS METABOTROPIC GLUTAMATE RECEPTOR ANTAGONISTS

FIELD OF THE INVENTION

The present invention relates to a new class of compounds, to pharmaceutical compositions containing said compounds and to the use of said compounds in therapy. The present invention further relates to processes for the preparation of said compounds and to new intermediates used in the preparation thereof.

BACKGROUND OF THE INVENTION

Glutamate is the major excitatory neurotransmitter in the mammalian central nervous system (CNS). Glutamate produces its effects on central neurons by binding to and thereby activating cell surface receptors. These receptors have been divided into two major classes, the ionotropic and metabotropic glutamate receptors, based on the structural features of the receptor proteins, the means by which the receptors transduce signals into the cell, and pharmacological profiles.

The metabotropic glutamate receptors (mGluRs) are G protein-coupled receptors that activate a variety of intracellular second messenger systems following the binding of glutamate. Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels. Schoepp et al., *Trends Pharmacol. Sci.* 14:13 (1993), Schoepp, *Neurochem. Int.* 24:439 (1994), Pin et al., *Neuropharmacology* 34:1 (1995), Bordi and Ugolini, *Prog. Neurobiol.* 59:55 (1999).

Eight distinct mGluR subtypes, termed mGluR1 through mGluR8, have been identified by molecular cloning. Nakanishi, *Neuron* 13:1031 (1994), Pin et al., *Neuropharmacology* 34:1 (1995), Knopfel et al., *J. Med. Chem.* 38:1417 (1995). Further receptor diversity occurs via expression of alternatively spliced forms of certain mGluR subtypes. Pin et al., *PNAS* 89:10331 (1992), Minakami et al., *BBRC* 199:1136 (1994), Joly et al., *J. Neurosci.* 15:3970 (1995).

Metabotropic glutamate receptor subtypes may be subdivided into three groups, Group I, Group II, and Group III mGluRs, based on amino acid sequence homology, the second messenger systems utilized by the receptors, and by their pharmacological characteristics. Group I mGluR comprises mGluR1, mGluR5 and their alternatively spliced variants. The binding of agonists to these receptors results in the activation of phospholipase C and the subsequent mobilization of intracellular calcium.

Neurological, Psychiatric and Pain Disorders.

Attempts at elucidating the physiological roles of Group I mGluRs suggest that activation of these receptors elicits neuronal excitation. Various studies have demonstrated that Group I mGluRs agonists can produce postsynaptic excitation upon application to neurons in the hippocampus, cerebral cortex, cerebellum, and thalamus, as well as other CNS regions. Evidence indicates that this excitation is due to direct activation of postsynaptic mGluRs, but it also has been suggested that activation of presynaptic mGluRs occurs, resulting in increased neurotransmitter release. Baskys, *Trends Pharmacol. Sci.* 15:92 (1992), Schoepp, *Neurochem. Int.* 24:439 (1994), Pin et al., *Neuropharmacology* 34:1 (1995), Watkins et al., *Trends Pharmacol. Sci.* 15:33 (1994).

Metabotropic glutamate receptors have been implicated in a number of normal processes in the mammalian CNS. Activation of mGluRs has been shown to be required for induction of hippocampal long-term potentiation and cerebellar long-term depression. Bashir et al., *Nature* 363:347 (1993), Bortolotto et al., *Nature* 368:740 (1994), Aiba et al., *Cell* 79:365 (1994), Aiba et al., *Cell* 79:377 (1994). A role for mGluR activation in nociception and analgesia also has been demonstrated. Meller et al., *Neuroreport* 4:879 (1993), Bordi and Ugolini, *Brain Res.* 871:223 (1999). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex. Nakanishi, *Neuron* 13:1031 (1994), Pin et al., *Neuropharmacology* 34:1, Knopfel et al., *J. Med. Chem.* 38:1417 (1995).

Further, Group I metabotropic glutamate receptors have been suggested to play roles in a variety of acute and chronic pathophysiological processes and disorders affecting the CNS. These include stroke, head trauma, anoxic and ischemic injuries, hypoglycemia, epilepsy, neurodegenerative disorders such as Alzheimer's disease, psychiatric disorders and pain. Schoepp et al., *Trends Pharmacol. Sci.* 14:13 (1993), Cunningham et al., *Life Sci.* 54:135 (1994), Hollman et al., *Ann. Rev. Neurosci.* 17:31 (1994), Pin et al., *Neuropharmacology* 34:1 (1995), Knopfel et al., *J. Med. Chem.* 38:1417 (1995), Spooren et al., *Trends Pharmacol. Sci.* 22:331 (2001), Gasparini et al. *Curr. Opin. Pharmacol.* 2:43 (2002), Neugebauer *Pain* 98:1 (2002). Much of the pathology in these conditions is thought to be due to excessive glutamate-induced excitation of CNS neurons. Because Group I mGluRs appear to increase glutamate-mediated neuronal excitation via postsynaptic mechanisms and enhanced presynaptic glutamate release, their activation probably contributes to the pathology. Accordingly, selective antagonists of Group I mGluR receptors could be therapeutically beneficial in all conditions underlain by excessive glutamate-induced excitation of CNS neurons, specifically as neuroprotective agents, analgesics or anticonvulsants.

Recent advances in the elucidation of the neurophysiological roles of metabotropic glutamate receptors generally and Group I in particular, have established these receptors as promising drug targets in the therapy of acute and chronic neurological and psychiatric disorders and chronic and acute pain disorders.

Gastro Intestinal Disorders

The lower esophageal sphincter (LES) is prone to relaxing intermittently. As a consequence, fluid from the stomach can pass into the esophagus since the mechanical barrier is temporarily lost at such times, an event hereinafter referred to as "reflux".

Gastro-esophageal reflux disease (GERD) is the most prevalent upper gastrointestinal tract disease. Current pharmacotherapy aims at reducing gastric acid secretion, or at neutralizing acid in the esophagus. The major mechanism behind reflux has been considered to depend on a hypotonic lower esophageal sphincter. However, e.g. *Holloway & Dent* (1990) *Gastroenterol. Clin. N. Amer.* 19, pp. 517-535, has shown that most reflux episodes occur during transient lower esophageal sphincter relaxations (TLESRs), i.e. relaxations not triggered by swallows. It has also been shown that gastric acid secretion usually is normal in patients with GERD.

The novel compounds according to the present invention are assumed to be useful for the inhibition of transient lower esophageal sphincter relaxations (TLESRs) and thus for treatment of gastro-esophageal reflux disorder (GERD).

The wording "TLESR", transient lower esophageal sphincter relaxations, is herein defined in accordance with Mittal, R. K., Holloway, R. H., Penagini, R., Blackshaw, L. A., Dent, J., 1995; *Transient lower esophageal sphincter relaxation*. Gastroenterology 109, pp. 601-610.

The wording "reflux" is herein defined as fluid from the stomach being able to pass into the esophagus, since the mechanical barrier is temporarily lost at such times.

The wording "GERD", gastro-esophageal reflux disease, is herein defined in accordance with van Heerwarden, M. A., Smout A. J. P. M., 2000; *Diagnosis of reflux disease*. Baillière's Clin. Gastroenterol. 14, pp. 759-774.

Because of their physiological and pathophysiological significance, there is a need for new potent mGluR agonists and antagonists that display a high selectivity for mGluR subtypes, particularly the Group I receptor subtype.

SUMMARY OF THE INVENTION

In one aspect of the invention there is provided a compound according to formula I

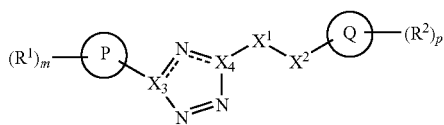

wherein $X_3$ and $X_4$ are selected from N and C, such that when $X_3$ is N, $X_4$ is C and when $X_3$ is C, $X_4$ is N;

P is selected from aryl and heteroaryl $R^1$ is attached to P via a carbon atom on ring P and is selected from the group consisting of hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl $C_{3-6}$cycloalkyl, $OC_{0-6}$alkyl$C_{3-6}$cycloalkyl, $C_{0-6}$alkylaryl, $OC_{0-6}$alkylaryl, CHO, $(CO)R^5$, $O(CO)R^5$, $O(CO)OR^5$, $O(CNR^5)OR^5$, $C_{1-6}$alkyl$OR^5$, $OC_{2-6}$alkyl$OR^5$, $C_{1-6}$alkyl$(CO)R^5$, $OC_{1-6}$alkyl$(CO)R^5$, $C_{0-6}$alkyl$CO_2R^5$, $OC_{1-6}$alkyl$CO_2R^5$, $C_{0-6}$alkylcyano, $OC_{2-6}$alkylcyano, $C_{0-6}$alkyl$NR^5R^6$, $OC_{2-6}$alkyl$NR^5R^6$, $C_{1-6}$alkyl$(CO)NR^5R^6$, $OC_{1-6}$alkyl$(CO)NR^5R^6$, $C_{0-6}$alkyl$NR^5(CO)R^6$, $OC_{2-6}$alkyl$NR^5(CO)R^6$, $C_{0-6}$alkyl$NR^5(CO)NR^5R^6$, $C_{0-6}$alkyl$SR^5$, $OC_{2-6}$alkyl$SR^5$, $C_{0-6}$alkyl$(SO)R^5$, $OC_{2-6}$alkyl$(SO)R^5$, $C_{0-6}$alkyl$SO_2R^5$, $OC_{2-6}$alkyl$SO_2R^5$, $C_{0-6}$alkyl$(SO_2)NR^5R^6$, $OC_{2-6}$alkyl$(SO_2)NR^5R^6$, $C_{0-6}$alkyl$NR^5(SO_2)R^6$, $OC_{2-6}$alkyl$NR^5(SO_2)R^6$, $C_{0-6}$alkyl$NR^5(SO_2)NR^5R^6$, $OC_{2-6}$alkyl$NR^5(SO_2)NR^5R^6$, $(CO)NR^5R^6$, $O(CO)NR^5R^6$, $NR^5OR^6$, $C_{0-6}$alkyl$NR^5(CO)OR^6$, $OC_{2-6}$alkyl$NR^5(CO)OR^6$, $SO_3R^5$ and a 5- or 6-membered ring containing one or more atoms independently selected from the group consisting of C, N, O and S;

$X^1$ is selected from the group consisting of $C_{2-3}$alkyl, $C_{2-3}$alkenyl, $NR^3$, O, S, $CR^3R^4$, SO, $SO_2$ $X^2$ is selected from the group consisting of a bond, $CR^3R^4$, O, S, $NR^3$, SO, $SO_2$ $R^3$ and $R^4$ are independently selected from a group consisting of hydrogen, hydroxy, $C_{1-6}$alyl, $C_{0-6}$alkylcyano, oxo, $=NR^5$, $=NOR^5$, $C_{1-4}$alkylhalo, halo, $C_{1-4}$alkyl$C_{3-7}$cycloalkyl, $C_{3-7}$cycloalkyl, $O(CO)C_{1-4}$alkyl, $(CO)C_{1-4}$alkyl, $C_{1-4}$alkyl$(SO)C_{0-4}$alkyl, $C_{1-4}$alkyl$(SO_2)C_{0-4}$alkyl, (SO)$C_{0-4}$alkyl, $(SO_2)C_{0-4}$alkyl, $OC_{1-4}$alkyl, $C_{1-4}$alkyl$OR^5$ and $C_{0-4}$alkyl$NR^5R^6$;

Q is a 4-, 5-, 6-, or 7-membered ring containing one or more heteroatoms selected from N, O and S, which is optionally fused to a 5-, 6-, or 7-membered ring containing one or more heteroatoms selected from N, O and S;

$R^2$ is selected from the group consisting of hydroxy, $C_{0-6}$alkylcyano, $=NR^5$, $=O$, $=NOR^5$, $C_{1-4}$alkylhalo, halo, $C_{1-6}$alkyl, $C_{3-6}$cycloalkyl, $C_{1-6}$alkylaryl, $C_{0-6}$alkylheteroaryl, $C_{0-6}$alkylcycloalkyl, $C_{0-6}$alkylheterocycloalkyl, $OC_{1-4}$alkyl, $OC_{0-6}$alkylaryl, $O(CO)C_{1-4}$alkyl, $(CO)O$ $C_{1-4}$alkyl, $C_{0-4}$alkyl$(S)C_{0-4}$alkyl, $C_{1-4}$alkyl$(SO)C_{0-4}$alkyl, $C_{1-4}$alkyl$(SO_2)C_{0-4}$alkyl, $(SO)C_{0-4}$alkyl, $(SO_2)C_{0-4}$alkyl, $C_{1-4}$alkyl$OR^5$, $C_{0-4}$alkyl$NR^5R^6$ and a 5- or 6-membered ring containing one or more atoms independently selected from C, N, O and S, which ring may optionally be fused with a 5- or 6-membered ring containing one or more atoms independently selected from the group consisting of C, N and O and wherein said ring and said fused ring may be substituted by one or more A; and any $C_{1-6}$alkyl, aryl, or heteroaryl defined under $R^1$, $R^2$ and $R^3$ may be substituted by one or more A; and A is selected from the group consisting of hydrogen, hydroxy, halo, nitro, oxo, $C_{0-6}$alkylcyano, $C_{0-4}$alkyl$C_{3-6}$cycloalkyl, $C_{1-6}$alkyl, $-OC_{1-6}$alkyl, $C_{1-6}$alkylhalo, $OC_{1-6}$alkylhalo, $C_{2-6}$alkenyl, $C_{0-3}$alkylaryl, $C_{0-6}$alkyl$OR^5$, $OC_{2-6}$alkyl$OR^5$, $C_{1-6}$alkyl$SR^5$, $OC_{2-6}$alkyl$SR^5$, $(CO)R^5$, $O(CO)R^5$, $O$ $C_{2-6}$alkylcyano, $OC_{1-6}$alkyl$CO_2R^5$, $O(CO)OR^5$, $OC_{1-6}$alkyl$(CO)R^5$, $C_{1-6}$alkyl$(CO)R^5$, $NR^5OR^6$, $C_{0-6}NR^5R^6$, $OC_{2-6}$alkyl$NR^5R^6$, $C_{0-6}$alkyl$(CO)NR^5R^6$, $OC_{1-6}$alkyl$(CO)NR^5R^6$, $OC_{2-6}$alkyl$NR^5(CO)R^6$, $C_{0-6}$alkyl$NR^5(CO)$ $R^6$, $C_{0-6}$alkyl$NR^5(CO)NR^5R^6$, $O(CO)NR^5R^6$, $C_{0-6}$alkyl$(SO_2)NR^5R^6$, $OC_{2-6}$alkyl$(SO_2)NR^5R^6$, $C_{0-6}$alkyl$NR^5(SO_2)R^6$, $OC_{2-6}$alkyl$NR^5(SO_2)R^6$, $SO_3R^5$, $C_{1-6}$alkyl$NR^5(SO_2)NR^5R^6$, $OC_{2-6}$alkyl$(SO_2)R^5$, $C_{0-6}$alkyl$(SO_2)R^5$, $C_{0-6}$alkyl$(SO)R^5$, $OC_{2-6}$alkyl$(SO)R^5$ and a 5- or 6-membered ring containing one or more atoms independently selected from the group consisting of C, N, O and S;

$R^5$ and $R^6$ are independently selected from, H, $C_{1-6}$alkyl, $C_{3-7}$cycloalkyl and aryl and salts and hydrates thereof m is selected from 0, 1, 2, 3 or 4 p is selected from 0, 1, 2, 3 or 4 or a salt or hydrate thereof.

with the proviso that the compound is not:

1-[hydroxyl-(2-phenyl-2H-tetrazol-5yl)-methyl]piperidine;

1-(2-phenyl-2H-tetrazol-5ylmethyl)-pyridine;

1-(2-phenyl-2H-tetrazol-5ylmethyl)-piperidine;

1-(2-benzothiazolyl)-4-[[5-(5-methyl-2-furanyl)-2H-tetrazol-2-yl]acetyl-piperazine;

1-(4-acetylphenyl)-4-[[5-(5-methyl-2-furanyl)-2H-tetrazol-2-yl]acetyl]-piperazine, or 5-(5-methyl-2-furanyl)-N-(2-phenyl-2H-benzotriazol-5-yl)-2H-tetrazole-2-acetamide.

In a further aspect of the invention there is provided pharmaceutical compositions comprising a therapeutically effective amount of the compound of formula I and a pharmaceutically acceptable diluent, excipients and/or inert carrier.

In yet a further aspect of the invention there is provided a pharmaceutical composition comprising the compound of formula I for use in the treatment of mGluR 5 receptor mediated disorders, and for use in the treatment of neurological disorders, psychiatric disorders, gastrointestinal disorders and pain disorders.

In still a further aspect of the invention there is provided the compound of formula I for use in therapy, especially for the treatment of mGluR 5 receptor mediated disorders, and for the treatment of neurological disorders, psychiatric disorders, gastrointestinal disorders and pain disorders.

In another aspect of the invention there is provided a processes for the preparation of compounds of formula I, and the intermediates used in the preparation thereof.

A further aspect of the invention is the use of a compound according to formula I for the manufacture of a medicament for the treatment or prevention of obesity and obesity related conditions, as well as treating eating disorders by inhibition of excessive food intake and the resulting obesity and complications associated therewith.

These and other aspects of the present invention are described in greater detail herein below.

DETAILED DESCRIPTION OF THE INVENTION

The object of the present invention is to provide compounds exhibiting an activity at metabotropic glutamate receptors (mGluRs), especially at the mGluR 5 receptors.

Listed below are definitions of various terms used in the specification and claims to describe the present invention.

For the avoidance of doubt it is to be understood that where in this specification a group is qualified by 'hereinbefore defined', 'defined hereinbefore' or 'defined above' said group encompasses the first occurring and broadest definition as well as each and all of the other definitions for that group.

For the avoidance of doubt it is to be understood that in this specification '$C_{1-6}$' means a carbon group having 1, 2, 3, 4, 5 or 6 carbon atoms. Similarly '$C_{1-3}$' means a carbon group having 1, 2, or 3 carbon atoms In the case where a subscript is the integer 0 (zero) the group to which the subscript refers indicates that the group is absent.

In this specification unless otherwise stated the term "heteroatom" refers to an atom which is not carbon or hydrogen. Examples of heteroatoms include but are not limited to nitrogen, oxygen, and sulfur In this specification, unless stated otherwise, the term "alkyl" includes both straight and branched chain alkyl groups and may be, but are not limited to methyl, ethyl, n-propyl, i-propyl, n-butyl, i-butyl, s-butyl, t-butyl, n-pentyl, i-pentyl, t-pentyl, neo-pentyl, n-hexyl or i-hexyl, t-hexyl. The term $C_{1-3}$alkyl has 1 to 3 carbon atoms and may be methyl, ethyl, n-propyl or i-propyl.

In this specification, unless stated otherwise, the term "alkenyl" includes both straight and branched chain alkenyl groups. The term "$C_{2-6}$alkenyl" refers to an alkenyl group having 2 to 6 carbon atoms and one or two double bonds, and may be, but is not limited to vinyl, allyl, propenyl, i-propenyl, butenyl, i-butenyl, crotyl, pentenyl, i-pentenyl and hexenyl.

In this specification, unless stated otherwise, the term "alkynyl" includes both straight and branched chain alkynyl groups. The term $C_{2-6}$alkynyl having 2 to 6 carbon atoms and one or two triple bonds, and may be, but is not limited to ethynyl, propargyl, butynyl, i-butynyl, pentynyl, i-pentynyl and hexynyl.

In this specification, unless stated otherwise, the term "cycloalkyl" refers to an optionally substituted, saturated cyclic hydrocarbon ring system. The term "$C_{3-7}$cycloalkyl" may be cyclopropyl, cyclobutyl, cyclopentyl, cyclohexyl or cycloheptyl.

In this specification, unless stated otherwise, the term "heterocycloalkyl" refers to an optionally substituted, saturated cyclic hydrocarbon ring system wherein one or more of the carbon atoms are replaced with heteroatom. The term "heterocycloalkyl" includes but is not limited to pyrrolidine, tetrahydrofuran, tetrahydrothiophene, piperidine, piperazine, morpholine, thiomorpholine, tetrahydropyran, tetrahydrothiopyran.

In this specification, unless stated otherwise, the term "alkoxy" includes both straight or branched alkoxy groups. $C_{1-3}$alkoxy may be, but is not limited to methoxy, ethoxy, n-propoxy or i-propoxy.

In this specification, unless stated otherwise, the term "halo" and "halogen" may be fluoro, chloro, bromo or iodo.

In this specification, unless stated otherwise, the term "alkylhalo" means an alkyl group as defined above, which is substituted with halo as described above.

The term "$C_{1-6}$alkylhalo" may include, but is not limited to fluoromethyl, difluoromethyl, trifluoromethyl, fluoroethyl, difluoroethyl or bromopropyl.

The term "$OC_{1-6}$alkylhalo" may include, but is not limited to fluoromethoxy, difluoromethoxy, trifluoromethoxy, fluoroethoxy or difluoroethoxy.

In this specification, unless otherwise stated, the term "aryl" refers to an optionally substituted monocyclic or bicyclic hydrocarbon ring system containing at least one unsaturated aromatic ring. Examples and suitable values of the term "aryl" are phenyl, naphthyl, 1,2,3,4-tetrahydronaphthyl, indyl and indenyl.

In this specification, unless stated otherwise, the term "heteroaryl" refers to an optionally substituted monocyclic or bicyclic unsaturated, aromatic ring system containing at least one heteroatom selected independently from N, O or S. Examples of "heteroaryl" may be, but are not limited to thiophene, thienyl, pyridyl, thiazolyl, furyl, pyrrolyl, triazolyl, imidazolyl, oxadiazolyl, oxazolyl, isoxazolyl, pyrazolyl, imidazolonyl, oxazolonyl, thiazolonyl, tetrazolyl and thiadiazolyl, benzoimidazolyl, benzooxazolyl, tetrahydrotriazolopyridyl, tetrahydrotriazolopyrimidinyl, benzofuryl, indolyl, isoindolyl, pyridonyl, pyridazinyl, pyrimidinyl, imidazopyridyl, oxazolopyridyl, thiazolopyridyl, pyridyl, imidazopyridazinyl, oxazolopyridazinyl, thiazolopyridazinyl and purinyl.

In this specification, unless stated otherwise, the term "alkylaryl", "alkylheteroaryl", "alkylcycloalkyl" and "alkylheterocycloalkyl" refer to a substituent that is attached via the alkyl group to an aryl, heteroaryl, cycloalkyl and heterocycloalkyl group.

In this specification, unless stated otherwise, the term "5- or 6-membered ring containing atoms independently selected from C, N, O or S", includes aromatic and heteroaromatic rings as well as carbocyclic and heterocyclic rings, which may be saturated, partially saturated or unsaturated. Examples of such rings may be, but are not limited to furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl, imidazolidinyl, imidazolinyl, triazolyl, morpholinyl, piperazinyl, piperidyl, piperidonyl, pyrazolidinyl, pyrazolinyl, pyrrolidinyl, pyrrolinyl, tetrahydropyranyl, thiomorpholinyl, phenyl, cyclohexyl, cyclopentyl and cyclohexenyl.

In this specification, unless stated otherwise, the term "4-, 5-, 6-, or 7-membered ring containing one or more heteroatoms selected from N, O and S, which ring is optionally fused to a 5-, 6-, or 7-membered ring containing one or more heteroatoms selected from N, O and S" refers to a heterocyclic or heteroaromatic ring which may be a saturated, partially unsaturated, or aromatic a ring Examples of such rings include, but are not limited to morpholinyl, thiomorpholinyl, piperazinyl, piperidinyl, piperidonyl, pyrazolidinyl, pyrazolinyl, pyrrolidinyl, pyrrolinyl, thiomorpholinyl furanyl, thiophenyl, pyridinyl, pyrazinyl, pyridazinyl, pyranyl, oxazolyl, thiazolyl, imidazolyl, triazolyl, tetrazolyl, azetidinyl, oxytanyl, azepanyl, oxazepanyl, oxepanyl, diazepanyl, thiazepanyl, and azepine and partially or fully unsaturated version thereof for example tetrahydropyranyl, dihydropyrazolyl and the like. This ring may be optionally fused to a second 5-, 6- or 7-membered ring which may be heterocyclic or heteroaromatic and which may be a saturated, partially unsaturated, or aromatic. The second or fused ring may be independently selected from examples such as morpholinyl, thiomorpholinyl, piperazinyl, piperidinyl, piperidonyl, pyrazolidinyl, pyrazolinyl, pyrrolidinyl, pyrrolinyl, thiomorpholinyl furanyl, thiophenyl, pyridinyl, pyrazinyl, pyridazinyl, pyranyl, oxazolyl, thiazolyl, imidazolyl, triazolyl, tetrazolyl, azetidinyl, oxytanyl, azepanyl, oxazepanyl, oxepanyl, diazepanyl, thiazepanyl, and azepine and unsaturated variations thereof, such as tetrahydropyranyl, dihydropyrazolyl and the like. Examples of fused rings systems that may be formed include but are not limited to isoquinoline, quinoline, quinazoline, quinoxaline, indole, indazole, indoline, benzoimidazole, benzooxazolyl, benzofuryl, imidazopyridyl, oxazolopyridyl, thiazolopyridyl, imidazopyridazinyl, oxalopyridazinyl, thiazolopyridazinyl, purinyl, tetrahydrotriazolopyridyl, tetrahydrotriazolopyrimidinyl, dihyrotriazolothiazine, tetrahydrotriazolopyrazine, tetrahydrotetraaza-azulene, dihydropyrollotriazol.

The term "fused" as used above refers to rings, which share two common atoms.

In this specification, unless stated otherwise, the term "bond" may be a saturated or unsaturated bond.

In this specification, unless stated otherwise, the term "=$NR^5$" and "=$NOR^5$" include imino- and oximo groups carrying an $R^5$ substituent and may be, or be part of, groups including, but not limited to iminoalkyl, iminohydroxy, iminoalkoxy, amidine, hydroxyamidine and alkoxyamidine.

In the case where a subscript is the integer 0 (zero) the group to which the subscript refers, indicates that the group is absent, i.e. there is a direct bond between the groups.

In this specification, unless stated otherwise, the term "bridge" means a molecular fragment, containing one or more atoms, or a bond, which connects two remote atoms in a ring, thus forming either bi- or tricyclic systems.

In one embodiment of the invention there are provided compounds of Formula I

Formula I wherein $X_3$ and $X_4$ are selected from N and C, such that when $X_3$ is N, $X_4$ is C and when $X_3$ is C, $X_4$ is N;

P is selected from aryl and heteroaryl $R^1$ is attached to P via a carbon atom on ring P and is selected from the group consisting of hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, CHO, $(CO)R^5$, $O(CO)R^5$, $O(CO)OR^5$, $O(CNR^5)OR^5$, $C_{1-6}$alkyl$OR^5$, $OC_{2-6}$alkyl$OR^5$, $C_{1-6}$alkyl(CO)$R^5$, $OC_{1-6}$alkyl(CO)$R^5$, $C_{0-6}$alkyl$CO_2R^5$, $OC_{1-6}$alkyl$CO_2R^5$, $C_{0-6}$alkylcyano, $OC_{2-6}$alkylcyano, $C_{0-6}$alkyl$NR^5R^6$, $OC_{2-6}$alkyl$NR^5R^6$, $C_{1-6}$alkyl(CO)$NR^5R^6$, $OC_{1-6}$alkyl(CO)$NR^5R^6$, $C_{0-6}$alkyl$NR^5$(CO)$R^6$, $OC_{2-6}$alkyl$NR^5$(CO)$R^6$, $C_{0-6}$alkyl$NR^5$(CO)$NR^5R^6$, $C_{0-6}$alkyl$SR^5$, $OC_{2-6}$alkyl$SR^5$, $C_{0-6}$alkyl(SO)$R^5$, $OC_{2-6}$alkyl(SO)$R^5$, $C_{0-6}$alkyl$SO_2R^5$, $OC_{2-6}$alkyl$SO_2R^5$, $C_{0-6}$alkyl($SO_2$)$NR^5R^6$, $OC_{2-6}$alkyl($SO_2$)$NR^5R^6$, $C_{0-6}$alkyl$NR^5$($SO_2$)$R^6$, $OC_{2-6}$alkyl$NR^5$($SO_2$)$R^6$, $C_{0-6}$alkyl$NR^5$($SO_2$)$NR^5R^6$, $OC_{2-6}$alkyl$NR^5$($SO_2$)$NR^5R^6$, (CO)$NR^5R^6$, O(CO)$NR^5R^6$, $NR^5OR^6$, $C_{0-6}$alkyl$NR^5$(CO)$OR^6$, $OC_{2-6}$alkyl$NR^5$(CO)$OR^6$, $SO_3R^5$ and a 5- or 6-membered ring containing one or more atoms independently selected from the group consisting of C, N, O and S;

$X^1$ is selected from the group consisting of $C_{1-3}$alkyl, $C_{2-3}$alkenyl, $NR^3$, O, S, $CR^3R^4$, SO, $SO_2$ $X^2$ is selected from the group consisting of a bond, $CR^3R^4$, O, S, $NR^3$, SO, $SO_2$ $R^3$ and $R^4$ are independently selected from a group consisting of hydrogen, hydroxy, $C_{1-6}$alyl, $C_{0-6}$alkylcyano, oxo, =$NR^5$, =$NOR^5$, $C_4$alkylhalo, halo, $C_{1-4}$alkyl, $C_{3-7}$cycloalkyl O(CO)$C_{1-4}$alkyl, (CO)$C_{1-4}$alkyl, $C_{1-4}$alkyl(SO)$C_{0-4}$alkyl, $C_{1-4}$alkyl($SO_2$)$C_{0-4}$alkyl, (SO)$C_{0-4}$alkyl, ($SO_2$)$C_{0-4}$alkyl, $OC_{1-4}$alkyl, $C_{1-4}$alkyl$OR^5$ and $C_{0-4}$alkyl$NR^5R^6$;

Q is a 4-, 5-, 6-, or 7-membered ring containing one or more heteroatoms selected from N, O and S, which ring is optionally fused to a 5-, 6-, or 7-membered ring containing one or more heteroatoms selected from N, O and S;

$R^2$ is selected from the group consisting of hydrogen, hydroxy, $C_{0-6}$alkylcyano, =$NR^5$, =O, =$NOR^5$, $C_{1-4}$alkylhalo, halo, $C_{1-6}$alkyl, $C_{3-6}$cycloalkyl, $C_{0-6}$alkylaryl, $C_{0-6}$alkylheteroaryl, $C_{0-6}$alkylcycloalkyl, $C_{0-6}$alkylheterocycloalkyl, $OC_{1-4}$alkyl, $OC_{0-6}$alkylaryl, $O(CO)C_{1-4}$alkyl, (CO)$OC_{1-4}$alkyl, $C_{0-4}$alkyl(S)$C_{0-4}$alkyl, $C_{1-4}$alkyl(SO)$C_{0-4}$alkyl, $C_{1-4}$alkyl($SO_2$)$C_{0-4}$alkyl, (SO)$C_{0-4}$alkyl, ($SO_2$)$C_{0-4}$alkyl, $C_{1-4}$alkyl$OR^5$, $C_{0-4}$alkyl$NR^5R^6$ and a 5- or 6-membered ring containing one or more atoms independently selected from C, N, O and S, which ring may optionally be fused with a 5- or 6-membered ring containing one or more atoms independently selected from the group consisting of C, N and O and wherein said ring and said fused ring may be substituted by one or more A; and any $C_{1-6}$alkyl, aryl, or heteroaryl defined under $R^1$, $R^2$ and $R^3$ may be substituted by one or more A; and A is selected from the group consisting of hydrogen, hydroxy, halo, nitro, oxo, $C_{0-6}$alkylcyano, $C_{0-4}$alkyl$C_{3-6}$cycloalkyl, $C_{1-6}$alkyl, —$OC_{1-6}$alkyl, $C_{1-6}$alkylhalo, $OC_{1-6}$alkylhalo, $C_{2-6}$alkenyl, $C_{0-3}$alkylaryl, $C_{0-6}$alkyl$OR^5$, $OC_{2-6}$alkyl$OR^5$, $C_{1-6}$alkyl$SR^5$, $OC_{2-6}$alkyl$SR^5$, $(CO)R^5$, $O(CO)R^5$, $OC_{2-6}$alkylcyano, $OC_{1-6}$alkyl$CO_2R^5$, $O(CO)OR^5$, $OC_{1-6}$alkyl(CO)$R^5$, $C_{1-6}$alkyl(CO)$R^5$, $NR^5OR^6$, $C_{0-6}NR^5R^6$, $OC_{2-6}$alkyl$NR^5R^6$, $C_{0-6}$alkyl(CO)$NR^5R^6$, $OC_{1-6}$alkyl(CO)$NR^5R^6$, $OC_{2-6}$alkyl$NR^5$(CO)$R^6$, $C_{0-6}$alkyl$NR^5$(CO)$R^6$, $C_{0-6}$alkyl$NR^5$(CO)$NR^5R^6$, O(CO)$NR^5R^6$, $C_{0-6}$alkyl($SO_2$)$NR^5R^6$, $OC_{2-6}$alkyl($SO_2$)$NR^5R^6$, $C_{0-6}$alkyl$NR^5$($SO_2$)$R^6$, $OC_{2-6}$alkyl$NR^5$($SO_2$)$R^6$, $SO_3R^5$, $C_{1-6}$alkyl$NR^5$($SO_2$)$NR^5R^6$, $OC_{2-6}$alkyl($SO_2$)$R^5$, $C_{0-6}$alkyl($SO_2$)$R^5$, $C_{0-6}$alkyl(SO)$R^5$, $OC_{2-6}$alkyl(SO)$R^5$ and a 5- or 6-membered ring containing one or more atoms independently selected from the group consisting of C, N, O and S;

$R^5$ and $R^6$ are independently selected from, H, $C_{1-6}$alkyl, $C_{3-7}$cycloalkyl and aryl and salts and hydrates thereof m is selected from 0, 1, 2, 3 or 4 p is selected from 0, 1, 2, 3 or 4 or a salt or hydrate thereof.

with the proviso that the compound is not:
1-[hydroxyl-(2-phenyl-2H-tetrazol-5yl)-methyl]piperidine;
1-(2-phenyl-2H-tetrazol-5ylmethyl)-pyridine; and
1-(2-phenyl-2H-tetrazol-5ylmethyl)-piperidine.

This invention relates to tetrazole compounds defined in formula 1. Compounds of formula 1 include those where P is an aryl or heteroaryl group. Particular embodiments of the invention include those wherein P is phenyl or pyridyl. P can be substituted with 0-4 substituents $R^1$. Preferably there are one or two $R^1$ substituents on P. In particular if there is one substituent $R^1$ it is preferable to have the substituent at the meta-position of the ring P relative to the attachment point of P at $X^3$, and if there are two substituents, at the 2-, and 5-positions of the ring P. Embodiments of the invention include those where $R^1$ is as defined in formula 1. In particular embodiments $R^1$ is selected from halo, $C_{1-6}$alkyl, —$OC_{1-6}$alkyl and $C_{0-6}$alkylcyano. More particularly $R^1$ is selected from Cl, F, cyano and methyl.

Formula 1 describes compounds having a 5-membered ring containing 4 nitrogen atoms and one carbon (tetrazole). Wherein the carbon can be either in the $X^3$ position or the $X^4$ position. Particular embodiments of the invention include compounds where the carbon is in the $X^4$ position.

Formula 1 describes variables $X^1$ and $X^2$, which form a linker between the 5-membered tetrazole ring and the ring Q. In embodiments of the invention $X^1$ is $CR^3R^4$. In preferred embodiments $R^3$ and $R^4$ are independently selected from H and $C_{0-6}$alkyl, and more particularly from H or methyl. In one embodiment of the invention $X^2$ is a bond. In another embodiment of the invention $X^2$ is selected from $CR^3R^4$, O, S and $NR^3$. When $X^2$ is $CR^3R^4$ or $NR^3$, $R^3$ and $R^4$ are as described above.

Q is defined as a ring having 4-, 5-, 6- or 7-members, wherein one or more of the ring members is a heteroatom selected from N, O and S. Furthermore the ring can be fused to a second ring having 5- or 6-memebers containing one or more heteroatoms to form a fused bicyclic group.

In one embodiment of the invention Q is a 5- or 6-member ring and is not fused to a second ring. In a more particular embodiment Q is a 5- or 6-membered heterocycloalkyl ring. Even more particularly Q is a 6-membered ring and more particularly a piperazine ring.

In another embodiment of the invention Q is a 5- or 6-membered heteroaromatic ring. In a more particular embodiment, Q is a 5-membered heteroaromatic ring, even more particularly Q is a triazole ring.

In yet another embodiment of the invention Q is 5-, 6- or 7-membered ring and is fused to a 5- or 6-membered ring. In a particular embodiment Q is a 5-, 6-, or 7-membered heterocyclic ring and is fused to a 5- or 6-membered heteroaryl ring. In a preferred embodiment Q is a 5-, 6-, or 7-membered heterocyclic ring fused to a triazole ring. In particular embodiments of the invention the fused bicyclic ring system formed is selected from tetrahydrotriazolopyridyl, tetrahydotriazolopyrimidinyl, dihyrotriazolothiazine, tetrahydotriazolopyrazine, tetrahydrotetraaza-azulene, dihydropyrollotriazol.

In a further embodiment of the invention when Q is a fused to a second ring as described above, $X^2$ is a bond and $X^1$ is $CR^3R^4$.

In still another embodiment when Q is a triazole that is not fused $X^1$ is $CR^3R^4$ and $X^2$ is $CR^3R^4$, O, S and $NR^3$, and when Q is piperazine, $X^1$ is $CR^3R^4$ and $X^2$ and is a bond.

In another aspect of the invention the ring Q (either or both of the 4, 5, or 7-membered ring and the fused 5, 6, or 7-memebered ring) may be further substituted with 0 to 4 substituents $R^2$.

In one embodiment $R^2$ is selected from $C_{1-6}$alkyl, $C_{1-6}$alkylhalo, $C_{3-7}$cylcoalkyl, $C_{0-6}$alkylaryl, $C_{0-6}$alkylheteroaryl, $(CO)OC_{1-4}$alkyl.

In a particular embodiment when Q is piperazine $R^2$ is $(CO)OC_{1-4}$alkyl. In another particular embodiment when Q is triazole $R^2$ is $C_{1-6}$alkyl, $C_{3-7}$cycloalkyl, $C_{0-6}$alkylaryl, $C_{0-6}$alkylheteroaryl. In a further embodiment there may be two substituents $R^2$ wherein one is selected from $C_{0-6}$alkylaryl, $C_{0-6}$alkylheteroaryl and the second is selected from $C_{1-6}$alkyl, $C_{3-7}$cylcoalkyl. More particularly one substituent may be selected from phenyl and pyridyl and the second may be selected from methyl or cyclopropyl.

In still another particular embodiment, when Q has a fused second ring, the second ring is substituted with $R^2$ selected from $C_{0-6}$alkylaryl, $C_{0-6}$alkylheteroaryl. More specifically when the fused ring is triazole the triazole ring is substituted with phenyl or pyridyl.

In another embodiment of the invention when $R^2$ is a 5- or 6-membered ring, $R^2$ may be substituted with one or more substituents A. Furthermore, any $C_{1-6}$alkyl, aryl or heteroaryl defined under $R^1$, $R^2$ and $R^3$ can be further substituted with one or more groups A. In a particular embodiment of the invention A is selected from halo, $C_{1-6}$alkyl, —$OC_{1-6}$alkyl and $C_{0-6}$alkylcyano.

The invention is also related to the following compounds;
Ethyl 4-{[2-(3-chlorophenyl)-2H-tetrazol-5-yl]methyl}piperazine-1-carboxylate
4-[2-(5-Chloro-2-fluoro-phenyl)-2H-tetrazol-5-ylmethyl]-piperazine-1-carboxylic acid ethyl ester
4-(2-m-Tolyl-2H-tetrazol-5-ylmethyl)-piperazine-1-carboxylic acid ethyl ester
4-[2-(3-Iodo-phenyl)-2H-tetrazol-5-ylmethyl]-piperazine-1-carboxylic acid ethyl ester
4-[2-(3-Cyano-phenyl)-2H-tetrazol-5-ylmethyl]-piperazine-1-carboxylic acid ethyl ester
4-[2-(2-Fluoro-5-methyl-phenyl)-2H-tetrazol-5-ylmethyl]-piperazine-1-carboxylic acid ethyl ester
4-[5-({[2-(3-chlorophenyl)-2H-tetrazol-5-yl]methyl}thio)-4-cyclopropyl-4H-1,2,4-triazol-3-yl]pyridine
4-[5-({1-[2-(3-chlorophenyl)-2H-tetrazol-5-yl]ethyl}thio)-4-cyclopropyl-4H-1,2,4-triazol-3-yl]pyridine
Ethyl 4-{1-[2-(3-chlorophenyl)-2H-tetrazol-5-yl]ethyl}piperazine-1-carboxylate
4-{5-[2-(5-Chloro-2-fluoro-phenyl)-2H-tetrazol-5-ylmethylsulfanyl]-4-methyl-4H-[1,2,4]triazol-3-yl}-pyridine
4-{5-[2-(5-Chloro-2-fluoro-phenyl)-2H-tetrazol-5-ylmethylsulfanyl]-4-cyclopropyl-4H-[1,2,4]triazol-3-yl}-pyridine
4-(5-{1-[2-(5-Chloro-2-fluoro-phenyl)-2H-tetrazol-5-yl]-ethylsulfanyl}-4-methyl-4H-[1,2,4]triazol-3-yl)-pyridine
4-(5-{1-[2-(5-Chloro-2-fluoro-phenyl)-2H-tetrazol-5-yl]-ethylsulfanyl}-4-cyclopropyl-4H-[1,2,4]triazol-3-yl)-pyridine
4-{1-[2-(5-Chloro-2-fluoro-phenyl)-2H-tetrazol-5-yl]-ethyl}-piperazine-1-carboxylic acid ethyl ester
4-[4-Cyclopropyl-5-(2-m-tolyl-2H-tetrazol-5-ylmethylsulfanyl)-4H-[1,2,4]triazol-3-yl]-pyridine
4-{4-Cyclopropyl-5-[1-(2-m-tolyl-2H-tetrazol-5-yl)-ethylsulfanyl]-4H-[1,2,4]triazol-3-yl}-pyridine
4-{4-Methyl-5-[1-(2-m-tolyl-2H-tetrazol-5-yl)-ethylsulfanyl]-4H-[1,2,4]triazol-3-yl}-pyridine
3-[5-(4-Cyclopropyl-5-pyridin-4-yl-4H-[1,2,4]triazol-3-ylsulfanylmethyl)-tetrazol-2-yl]-benzonitrile
3-{5-[1-(4-Cyclopropyl-5-pyridin-4-yl-4H-[1,2,4]triazol-3-ylsulfanyl)-ethyl]-tetrazol-2-yl}-benzonitrile
3-{5-[1-(4-Methyl-5-pyridin-4-yl-4H-[1,2,4]triazol-3-ylsulfanyl)-ethyl]-tetrazol-2-yl}-benzonitrile4-{4-Cyclopropyl-5-[2-(2-fluoro-5-methyl-phenyl)-2H-tetrazol-5-ylmethylsulfanyl]-4H-[1,2,4]triazol-3-yl]-pyridine
4-(4-Cyclopropyl-5-{1-[2-(2-fluoro-5-methyl-phenyl)-2H-tetrazol-5-yl]-ethylsulfanyl}-4H-[1,2,4]triazol-3-yl)-pyridine
4-(5-{1-[2-(2-Fluoro-5-methyl-phenyl)-2H-tetrazol-5-yl]-ethylsulfanyl}-4-methyl-4H-[1,2,4]triazol-3-yl)-pyridine
Methyl-(4-methyl-5-pyridin-4-yl-4H-[1,2,4]triazol-3-yl)-(2-m-tolyl-2H-tetrazol-5-ylmethyl)-amine
Methyl-(4-methyl-5-pyridin-4-yl-4H-[1,2,4]triazol-3-yl)-[1-(2-m-tolyl-2H-tetrazol-5-yl)-ethyl]-amine
[2-(3-Chloro-phenyl)-2H-tetrazol-5-ylmethyl]-methyl-(4-methyl-5-pyridin-4-yl-4H-[1,2,4]triazol-3-yl)-amine
{1-[2-(3-Chloro-phenyl)-2H-tetrazol-5-yl]-ethyl}-methyl-(4-methyl-5-pyridin-4-yl-4H-[1,2,4]triazol-3-yl)-amine
[2-(2-Fluoro-5-methyl-phenyl)-2H-tetrazol-5-ylmethyl]-methyl-(4-methyl-5-pyridin-4-yl-4H-[1,2,4]triazol-3-yl)-amine
{1-[2-(2-Fluoro-5-methyl-phenyl)-2H-tetrazol-5-yl]-ethyl}-methyl-(4-methyl-5-pyridin-4-yl-4H-[1,2,4]triazol-3-yl)-amine
[2-(3-Iodo-phenyl)-2H-tetrazol-5-ylmethyl]-methyl-(4-methyl-5-pyridin-4-yl-4H-[1,2,4]triazol-3-yl)-amine
{1-[2-(3-Iodo-phenyl)-2H-tetrazol-5-yl]-ethyl}-methyl-(4-methyl-5-pyridin-4-yl-4H-[1,2,4]triazol-3-yl)-amine
Methyl-(4-methyl-5-pyridin-4-yl-4H-[1,2,4]triazol-3-yl)-(2-m-tolyl-2H-tetrazol-5-ylmethyl)-amine
Methyl-(4-methyl-5-pyridin-4-yl-4H-[1,2,4]triazol-3-yl)-[1-(2-m-tolyl-2H-tetrazol-5-yl)-ethyl]-amine
[2-(3-Chloro-phenyl)-2H-tetrazol-5-ylmethyl]-methyl-(4-methyl-5-pyridin-4-yl-4H-[1,2,4]triazol-3-yl)-amine
{1-[2-(3-Chloro-phenyl)-2H-tetrazol-5-yl]-ethyl}-methyl-(4-methyl-5-pyridin-4-yl-4H-[1,2,4]triazol-3-yl)-amine
[2-(2-Fluoro-5-methyl-phenyl)-2H-tetrazol-5-ylmethyl]-methyl-(4-methyl-5-pyridin-4-yl-4H-[1,2,4]triazol-3-yl)-amine
{1-[2-(2-Fluoro-5-methyl-phenyl)-2H-tetrazol-5-yl]-ethyl}-methyl-(4-methyl-5-pyridin-4-yl-4H-[1,2,4]triazol-3-yl)-amine
8-[2-(3-Iodo-phenyl)-2H-tetrazol-5-ylmethyl]-3-pyridin-4-yl-5,6,7,8-tetrahydro-[1,2,4]triazolo[4,3-a]pyrimidine
8-{1-[2-(3-Iodo-phenyl)-2H-tetrazol-5-yl]-ethyl}-3-pyridin-4-yl-5,6,7,8-tetrahydro-[1,2,4]triazolo[4,3-a]pyrimidine
3-Pyridin-4-yl-8-(2-m-tolyl-2H-tetrazol-5-ylmethyl)-5,6,7,8-tetrahydro-4H-1,2,3a,8-tetraaza-azulene
3-Pyridin-4-yl-8-[1-(2-m-tolyl-2H-tetrazol-5-yl)-ethyl]-5,6,7,8-tetrahydro-4H-1,2,3a,8-tetraaza-azulene
8-[2-(3-Chloro-phenyl)-2H-tetrazol-5-ylmethyl]-3-pyridin-4-yl-5,6,7,8-tetrahydro-4H-1,2,3a,8-tetraaza-azulene
8-{1-[2-(3-Chloro-phenyl)-2H-tetrazol-5-yl]-ethyl}-3-pyridin-4-yl-5,6,7,8-tetrahydro-4H-1,2,3a,8-tetraaza-azulene
8-[2-(2-Fluoro-5-methyl-phenyl)-2H-tetrazol-5-ylmethyl]-3-pyridin-4-yl-5,6,7,8-tetrahydro-4H-1,2,3a,8-tetraaza-azulene
8-{1-[2-(2-Fluoro-5-methyl-phenyl)-2H-tetrazol-5-yl]-ethyl}-3-pyridin-4-yl-5,6,7,8-tetrahydro-4H-1,2,3a,8-tetraaza-azulene
8-[2-(3-Iodo-phenyl)-2H-tetrazol-5-ylmethyl]-3-pyridin-4-yl-5,6,7,8-tetrahydro-4H-1,2,3a,8-tetraaza-azulene
8-{1-[2-(3-Iodo-phenyl)-2H-tetrazol-5-yl]-ethyl}-3-pyridin-4-yl-5,6,7,8-tetrahydro-4H-1,2,3a,8-tetraaza-azulene
4-(5-{[2-(3-chlorophenyl)-2H-tetrazol-5-yl]methoxy}-4-methyl-4H-1,2,4-triazol-3-yl)pyridine
4-(5-{1-[2-(3-chlorophenyl)-2H-tetrazol-5-yl]ethoxy}-4-methyl-4H-1,2,4-triazol-3-yl)pyridine
4-[4-Methyl-5-(2-m-tolyl-2H-tetrazol-5-ylmethoxy)-4H-[1,2,4]triazol-3-yl]-pyridine
4-{4-Methyl-5-[1-(2-m-tolyl-2H-tetrazol-5-yl)-ethoxy]-4H-[1,2,4]triazol-3-yl}-pyridine
4-{5-[2-(2-Fluoro-5-methyl-phenyl)-2H-tetrazol-5-ylmethoxy]-4-methyl-4H-[1,2,4]triazol-3-yl}-pyridine
4-(5-{1-[2-(2-Fluoro-5-methyl-phenyl)-2H-tetrazol-5-yl]-ethoxy}-4-methyl-4H-[1,2,4]triazol-3-yl)-pyridine
4-{5-[2-(3-Chloro-phenyl)-2H-tetrazol-5-ylmethoxy]-4-cyclopropyl-4H-[1,2,4]triazol-3-yl}-pyridine
4-(5-{1-[2-(3-Chloro-phenyl)-2H-tetrazol-5-yl]-ethoxy}-4-cyclopropyl-4H-[1,2,4]triazol-3-yl)-pyridine
4-[4-Cyclopropyl-5-(2-m-tolyl-2H-tetrazol-5-ylmethoxy)-4H-[1,2,4]triazol-3-yl]-pyridine
4-{4-Cyclopropyl-5-[1-(2-m-tolyl-2H-tetrazol-5-yl)-ethoxy]-4H-[1,2,4]triazol-3-yl}-pyridine
4-{4-Cyclopropyl-5-[2-(2-fluoro-5-methyl-phenyl)-2H-tetrazol-5-ylmethoxy]-4H-[1,2,4]triazol-3-yl}-pyridine
4-(4-Cyclopropyl-5-{1-[2-(2-fluoro-5-methyl-phenyl)-2H-tetrazol-5-yl]-ethoxy}-4H-[1,2,4]triazol-3-yl)-pyridine
4-{5-[2-(3-Iodo-phenyl)-2H-tetrazol-5-ylmethoxy]-4-methyl-4H-[1,2,4]triazol-3-yl}-pyridine
4-(5-{1-[2-(3-Iodo-phenyl)-2H-tetrazol-5-yl]-ethoxy}-4-methyl-4H-[1,2,4]triazol-3-yl)-pyridine
4-{4-Cyclopropyl-5-[2-(3-iodo-phenyl)-2H-tetrazol-5-ylmethoxy]-4H-[1,2,4]triazol-3-yl}-pyridine
4-(4-Cyclopropyl-5-{1-[2-(3-iodo-phenyl)-2H-tetrazol-5-yl]-ethoxy}-4H-[1,2,4]triazol-3-yl)-pyridine
3-[5-(4-Methyl-5-pyridin-4-yl-4H-[1,2,4]triazol-3-yloxymethyl)-tetrazol-2-yl]-benzonitrile
3-{5-[1-(4-Methyl-5-pyridin-4-yl-4H-[1,2,4]triazol-3-yloxy)-ethyl]-tetrazol-2-yl}-benzonitrile
3-[5-(4-Cyclopropyl-5-pyridin-4-yl-4H-[1,2,4]triazol-3-yloxymethyl)-tetrazol-2-yl]-benzonitrile
3-{5-[1-(4-Cyclopropyl-5-pyridin-4-yl-4H-[1,2,4]triazol-3-yloxy)-ethyl]-tetrazol-2-yl}-benzonitrile
3-(5-{[Methyl-(4-methyl-5-pyridin-4-yl-4H-[1,2,4]triazol-3-yl)-amino]-methyl}-tetrazol-2-yl)-benzonitrile
3-(5-{1-[Methyl-(4-methyl-5-pyridin-4-yl-4H-[1,2,4]triazol-3-yl)-amino]-ethyl}-tetrazol-2-yl)-benzonitrile
3-[5-(3-Pyridin-4-yl-6,7-dihydro-5H-[1,2,4]triazolo[4,3-a]pyrimidin-8-ylmethyl)-tetrazol-2-yl]-benzonitrile
3-{5-[1-(3-Pyridin-4-yl-6,7-dihydro-5H-[1,2,4]triazolo[4,3-a]pyrimidin-8-yl)-ethyl]-tetrazol-2-yl}-benzonitrile
3-[5-(3-Pyridin-4-yl-4,5,6,7-tetrahydro-1,2,3a,8-tetraazaazulen-8-ylmethyl)-tetrazol-2-yl]-benzonitrile
3-{5-[1-(3-Pyridin-4-yl-4,5,6,7-tetrahydro-1,2,3a,8-tetraaza-azulen-8-yl)-ethyl]-tetrazol-2-yl}-benzonitrile
(R) & (S)-4-(5-{1-[2-(3-chlorophenyl)-2H-tetrazol-5-yl]ethoxy}-4-methyl-4H-1,2,4-triazol-3-yl)pyridine
2-(3-chloro-phenyl)-5-[(triphenyl-$\lambda^5$-phosphanyl)-methyl]-2H-tetrazole hydrobromide
4-(5-{2-[2-(3-chloro-phenyl)-2H-tetrazol-5-yl]-vinyl}-4-ethyl-4H-[1,2,4]triazol-3-yl)-pyridine
4-(5-{2-[2-(3-chloro-phenyl)-2H-tetrazol-5-yl]-vinyl}-4-ethyl-4H-[1,2,4]triazol-3-yl)-pyridine
1-[2-(3-Chloro-phenyl)-2H-tetrazol-5-yl]-2-(4-cyclopropyl-5-pyridin-4-yl-4H-[1,2,4]triazol-3-yl)-ethanol
2-[2-(3-Chloro-phenyl)-2H-tetrazol-5-yl]-1-(4-cyclopropyl-5-pyridin-4-yl-4H-[1,2,4]triazol-3-yl)-ethanol
4-(5-{2-[2-(3-chloro-phenyl)-2H-tetrazol-5-yl]-vinyl}-4-ethyl-4H-[1,2,4]triazol-3-yl)-pyridine
3-[4-Methyl-5-({[2-(3-methylphenyl)-2H-tetrazol-5-yl]methyl}thio)-4H-1,2,4-triazol-3-yl]benzonitrile,
5-({[5-(3,5-Difluorophenyl)-4-ethyl-4H-1,2,4-triazol-3-yl]thio}methyl)-2-(3-methylphenyl)-2H-tetrazole, 3-[4-Methyl-5-({1-[2-(3-methylphenyl)-2H-tetrazol-5-yl]ethyl)thio)-4H-1,2,4-triazol-3-yl]benzonitrile, 5-(1-{[5-(3,5-Difluorophenyl)-4-ethyl-4H-1,2,4-triazol-3-yl]thio}ethyl)-2-(3-methylphenyl)-2H-tetrazole, 6-(4-{1-[2-(3-Chlorophenyl)-2H-tetrazol-5-yl]ethyl}piperazin-1-yl)nicotinonitrile, 3-(4-{1-[2-(3-Chlorophenyl)-2H-tetrazol-5-yl]ethyl}piperazin-1-yl)pyrazine-2-carbonitrile, 2-(4-{1-[2-(3-Chlorophenyl)-2H-tetrazol-5-yl]ethyl}piperazin-1-yl)nicotinonitrile, 1-{1-[2-(3-Chlorophenyl)-2H-tetrazol-5-yl]ethyl}-4-(3-nitropyridin-2-yl)piperazine, 8-{1-[2-(3-Chlorophenyl)-2H-tetrazol-5-yl]ethyl}-3-(3,5-difluorophenyl)-5,6,7,8-tetrahydro[1,2,4]triazolo[4,3-a]pyrimidine, 8-{1-[2-(3-Chlorophenyl)-2H-tetrazol-5-yl]ethyl}-3-(4-methoxyphenyl)-5,6,7,8-tetrahydro[1,2,4]triazolo[4,3-a]pyrimidine, 3-(2-Chloro-6-methoxypyridin-4-yl)-8-{1-[2-(3-chlorophenyl)-2H-tetrazol-5-yl]ethyl}-5,6,7,8-Tetrahydro[1,2,4]triazolo[4,3-a]pyrimidine, 8-{1-[2-(3-Chlorophenyl)-2H-tetrazol-5-yl]ethyl}-3-(2-methoxypyridin-4-yl)-5,6,7,8-tetrahydro[1,2,4]triazolo[4,3-a]pyrimidine, 8-{[2-(3-Chlorophenyl)-2H-tetrazol-5-yl]methyl}-3-(2-methoxypyridin-4-yl)-5,6,7,8-tetrahydro[1,2,4]triazolo[4,3-a]pyrimidine, 3-(5-{[3-(2-Methoxypyridin-4-yl)-6,7-dihydro[1,2,4]triazolo[4,3-a]pyrimidine-8(5H)-yl]methyl}-2H-tetrazol-2-yl)benzonitrile, 3-(2-Methoxypyridin-4-yl)-8-{1-[2-(3-iodophenyl)-2H-tetrazol-5-yl]ethyl}-5,6,7,8-tetrahydro[1,2,4]triazolo[4,3-a]pyrimidine, 3-(5-{1-[3-(2-Methoxypyridin-4-yl)-6,7-dihydro[1,2,4]triazolo[4,3-a]pyrimidin-8(5H)-yl]ethyl}-2H-tetrazol-2-yl)benzonitrile, 3-(5-{[3-(2-Methoxypyridin-4-yl)-5,6,7,8-tetrahydro-9H-[1,2,4]triazolo[4,3-a][1,3]diazepin-9-yl]methyl}-2H-tetrazol-2-yl)benzonitrile, 3-(5-{[3-(2,6-Dimethoxypyrimidin-4-yl)-6,7-dihydro[1,2,4]triazolo[4,3-a]pyrimidin-8(5H)-yl]methyl}-2H-tetrazol-2-yl)benzonitrile, (R) 3-(5-{1-[3-(2-Methoxypyridin-4-yl)-6,7-dihydro[1,2,4]triazolo[4,3-a]pyrimidin-8(5H)-yl]ethyl}-2H-tetrazol-2-yl)benzonitrile, (S) 3-(5-{1-[3-(2-Methoxypyridin-4-yl)-6,7-dihydro[1,2,4]triazolo[4,3-a]pyrimidin-8(5H)-yl]ethyl}-2H-tetrazol-2-yl)benzonitrile, (R) Ethyl 4-{1-[2-(3-chlorophenyl)-2H-tetrazol-5-yl]ethyl}piperazine-1-carboxylate, (S) Ethyl 4-{1-[2-(3-chlorophenyl)-2H-tetrazol-5-yl]ethyl}piperazine-1-carboxylate, (R) Ethyl 4-{1-[2-(5-chloro-2-fluorophenyl)-2H-tetrazol-5-yl]ethyl}piperazine-1-carboxylate, (S) Ethyl 4-{1-[2-(5-chloro-2-fluorophenyl)-2H-tetrazol-5-yl]ethyl}piperazine-1-carboxylate, (R) 6-(4-{1-[2-(3-Chlorophenyl)-2H-tetrazol-5-yl]ethyl}piperazin-1-yl)nicotinonitrile, (S) 6-(4-{1-[2-(3-Chlorophenyl)-2H-tetrazol-5-yl]ethyl}piperazin-1-yl)nicotinonitrile, (R) 3-(4-{1-[2-(3-Chlorophenyl)-2H-tetrazol-5-yl]ethyl}piperazin-1-yl)pyrazine-2-carbonitrile, (S) 3-(4-{1-[2-(3-Chlorophenyl)-2H-tetrazol-5-yl]ethyl}piperazin-1-yl)pyrazine-2-carbonitrile, 4-(5-{(S)-1-[2-(3-Chloro-phenyl)-2H-tetrazol-5-yl]-ethoxy}-4-methyl-4H-[1,2,4]triazol-3-yl)-pyridine, 2-(3-Chloro-phenyl)-5-{(R)-1-[5-(3,5-difluoro-phenyl)-4-methyl-4H-[1,2,4]triazol-3-yloxy]-ethyl}-2H-tetrazole, 3-(5-{(R)-1-[2-(3-Chloro-phenyl)-2H-tetrazol-5-yl]-ethoxy}-4-methyl-4H-[1,2,4]triazol-3-yl)-pyridine, 4-(5-{2-[5-(3-Chlorophenyl)-2H-tetrazol-2-yl]propyl}-4-methyl-4H-1,2,4-triazol-3-yl)pyridine, 4-(5-{(R)-1-[2-(3-Chloro-phenyl)-2H-tetrazol-5-yl]-ethoxy}-4-methyl-4H-[1,2,4]triazol-3-yl)-pyridine, 2-(3-chlorophenyl)-5-[1-methyl-2-phenylvinyl]-2H-tetrazole, and 2-({1-[2-(3-chlorophenyl)-2H-tetrazol-5-yl]ethyl}thio)-imidazo[4,5-b]pyridine;

Embodiments of the invention include salt forms of compounds of formula 1. Salts for use in pharmaceutical compositions will be pharmaceutically acceptable salts, but other salts may be useful in the production of the compounds of formula I.

A suitable pharmaceutically acceptable salt of the compounds of the invention is, for example, an acid-addition salt, for example an inorganic or organic acid. In addition, a suitable pharmaceutically acceptable salt of the compounds of the invention is an alkali metal salt, an alkaline earth metal salt or a salt with an organic base.

Other pharmaceutically acceptable salts and methods of preparing these salts may be found in, for example, Remington's Pharmaceutical Sciences (18$^{th}$ Edition, Mack Publishing Co.) 1990.

Some compounds of formula I may have chiral centres and/or geometric isomeric centres (E- and Z-isomers), and it is to be understood that the invention encompasses all such optical, diastereoisomeric and geometric isomers.

The invention also relates to any and all tautomeric forms of the compounds of formula I. The invention also relates to any and all solvate and hydrate forms of compounds of formula 1.

Pharmaceutical Composition

According to one aspect of the present invention there is provided a pharmaceutical composition comprising as active ingredient a therapeutically effective amount of the compound of formula I, or salts, solvates or solvated salts thereof, in association with one or more pharmaceutically acceptable diluent, excipients and/or inert carrier.

The composition may be in a form suitable for oral administration, for example as a tablet, pill, syrup, powder, granule or capsule, for parenteral injection (including intravenous, subcutaneous, intramuscular, intravascular or infusion) as a sterile solution, suspension or emulsion, for topical administration e.g. as an ointment, patch or cream or for rectal administration e.g. as a suppository.

In general the above compositions may be prepared in a conventional manner using one or more conventional excipients, pharmaceutical acceptable diluents and/or inert carriers.

Suitable daily doses of the compounds of formula I in the treatment of a mammal, including man are approximately 0.01 to 250 mg/kg bodyweight at peroral administration and about 0.001 to 250 mg/kg bodyweight at parenteral administration.

The typical daily dose of the active ingredients varies within a wide range and will depend on various factors such as the relevant indication, severity of the illness being treated, the route of administration, the age, weight and sex of the patient and the particular compound being used, and may be determined by a physician.

Medical Use

It has been found that the compounds according to the present invention, or salts, solvates or solvated salts thereof, exhibit a high degree of potency and selectivity for individual metabotropic glutamate receptor (mGluR) subtypes. Accordingly, the compounds of the present invention are expected to be useful in the treatment of conditions associated with excitatory activation of mGluR5 and for inhibiting neuronal damage caused by excitatory activation of mGluR5. The compounds may be used to produce an inhibitory effect of mGluR5 in mammals, including man.

The mGluR Group I receptor including mGluR5 are highly expressed in the central and peripheral nervous system and in other tissues. Thus, it is expected that the compounds of the invention are well suited for the treatment of mGluR5-mediated disorders such as acute and chronic neurological and psychiatric disorders, gastrointestinal disorders, and chronic and acute pain disorders.

The invention relates to compounds of formula I as defined hereinbefore, for use in therapy.

The invention relates to compounds of formula I as defined hereinbefore, for use in treatment of mGluR5-mediated disorders.

The invention relates to compounds of formula I as defined hereinbefore, for use in treatment of Alzheimer's disease senile dementia, AIDS-induced dementia, Parkinson's disease, amylotropic lateral sclerosis, Huntington's Chorea, migraine, epilepsy, schizophrenia, depression, anxiety, acute anxiety, ophthalmological disorders such as retinopathies, diabetic retinopathies, glaucoma, auditory neuropathic disorders such as tinnitus, chemotherapy induced neuropathies, post-herpetic neuralgia and trigeminal neuralgia, tolerance, dependency, Fragile X, autism, mental retardation, schizophrenia and Down's Syndrome.

The invention relates to compounds of formula I as defined hereinbefore, for use in treatment of pain related to migraine, inflammatory pain, neuropathic pain disorders such as diabetic neuropathies, arthritis and rheumatoid diseases, low back pain, post-operative pain and pain associated with various conditions including angina, renal or biliary colic, menstruation, migraine and gout.

The invention relates to compounds of formula I as defined hereinbefore, for use in treatment of stroke, head trauma, anoxic and ischemic injuries, hypoglycemia, cardiovascular diseases and epilepsy.

The present invention relates also to the use of a compound of formula I as defined hereinbefore, in the manufacture of a medicament for the treatment of mGluR Group I receptor-mediated disorders and any disorder listed above.

One embodiment of the invention relates to the use of a compound according to formula I in the treatment of gastrointestinal disorders.

Another embodiment of the invention relates to the use of a compound according to formula I, for the manufacture of a medicament for the inhibition of transient lower esophageal sphincter relaxations, for the treatment of GERD, for the prevention of reflux, for the treatment regurgitation, treatment of asthma, treatment of laryngitis, treatment of lung disease and for the management of failure to thrive.

A further aspect of the invention is the use of a compound according to formula I for the manufacture of a medicament for the treatment or prevention of functional gastrointestinal disorders, such as functional dyspepsia (FD). Yet another aspect of the invention is the use of a compound according to formula I for the manufacture of a medicament for the treatment or prevention of irritable bowel syndrome (IBS), such as constipation predominant IBS, diarrhea predominant IBS or alternating bowel movement predominant IBS.

A further aspect of the invention is the use of a compound according to formula I for the manufacture of a medicament for the treatment or prevention of obesity and obesity related conditions, as well as treating eating disorders by inhibition of excessive food intake and the resulting obesity and complications associated therewith.

The invention also provides a method of treatment of mGluR5-mediated disorders and any disorder listed above, in a patient suffering from, or at risk of, said condition, which comprises administering to the patient an effective amount of a compound of formula I, as hereinbefore defined.

The dose required for the therapeutic or preventive treatment of a particular disorder will necessarily be varied depending on the host treated, the route of administration and the severity of the illness being treated.

In the context of the present specification, the term "therapy" and "treatment" includes prevention or prophylaxis, unless there are specific indications to the contrary. The terms "therapeutic" and "therapeutically" should be construed accordingly.

In this specification, unless stated otherwise, the term "antagonist" and "inhibitor" shall mean a compound that by any means, partly or completely, blocks the transduction pathway leading to the production of a response by the ligand.

The term "disorder", unless stated otherwise, means any condition and disease associated with metabotropic glutamate receptor activity.

Non-Medical Use

In addition to their use in therapeutic medicine, the compounds of formula I, salts, solvates or solvated salts thereof, are also useful as pharmacological tools in the development and standardisation of in vitro and in vivo test systems for the evaluation of the effects of inhibitors of mGluR related activity in laboratory animals such as cats, dogs, rabbits, monkeys, rats and mice, as part of the search for new therapeutics agents.

Methods of Preparation

Another aspect of the present invention provides processes for preparing compounds of formula I, or salts, solvates or solvated salts thereof. Processes for the preparation of the compounds in the present invention are described herein.

Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include for example, straight and reversed phase chromatography on column or rotating plate, recrystallisation, distillation and liquid-liquid or solid-liquid extraction, which will be readily understood by the one skilled in the art. The definitions of substituents and groups are as in formula I except where defined differently. The term "room temperature" and "ambient temperature" shall mean, unless otherwise specified, a temperature between 16 and 25° C.

The term "reflux" shall mean, unless otherwise stated, in reference to an employed solvent using a temperature at or above the boiling point of named solvent.

Methods of Preparation of Compounds of Formula I

The non-limiting synthetic paths given below, are useful for further preparation of intermediates and of compounds of formula I. Other starting materials used in the preparation of compounds of Formula I are either commercially available or can be prepared via methods described in the literature.

Compounds of formula v are prepared through condensation between aldehydes of formula ii, for example cinnamaldehyde or glyoxalic acid, with arylsulphonylhydrazines iii, such as 4-toluensulfonylhydrazine, in a suitable solvent, for example methanol, ethanol, DMF or dialkylethers, at a temperature between 0 to 100° C., alternatively without solvent under microwave irradiation. Similarly, arylhydrazones of formula vi may be formed from the reaction of arylhydrazine iv, with aldehydes of formula ii. [J. Med. Chem. 1980, 23, 631-634; Monatshefte fuer Chemie 2001, 403-406; J. Med. Chem. 2000, 43, 953-970; J. Med. Chem. 1978, 21, 1254-60]

Diazonium salts of formula viii are available from a suitably substituted aryl or heteroaryl amine of formula vii using well known methods, via diazotization using a nitrite source such as sodium nitrite or isoamyl nitrite in the presence of a suitable acid source such as hydrochloric acid or tetrafluoroboric acid in a solvent such as water at a temperature between −10 to 0° C. In the case where a less soluble counter ion X⁻ is employed, such as tetrafluoroborate, the diazonium salt thus formed may be collected by precipitation and used in subsequent reactions under non-aqueous conditions. Soluble diazonium salts formed using other acid sources may be precipitated by the addition of a suitable reagent such as tetrafluoroboric acid or sodium tetrafluoroborate [Angew. Chem. Int. Ed. Engl. 2004, 43, 897-900].

Tetrazoles of formula ix wherein G is an electron withdrawing group, such as an olefin, carbonyl or aryl group, may be prepared by 1,3-dipolar cycloaddition of a diazonium salt onto an aryl sulfonyl hydrazone followed by elimination of the arylsulfinic acid to generate the tetrazole ring, in protic solvents such as water and alcohol or mixtures thereof, in basic aprotic solvents such as pyridine, or mixtures of these solvents with protic solvents used to generate the diazonium salt. [J. Med. Chem. 2000, 43, 953-970]

Scheme 2

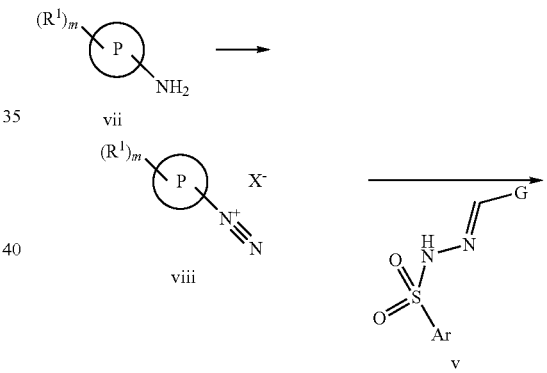

Scheme 1

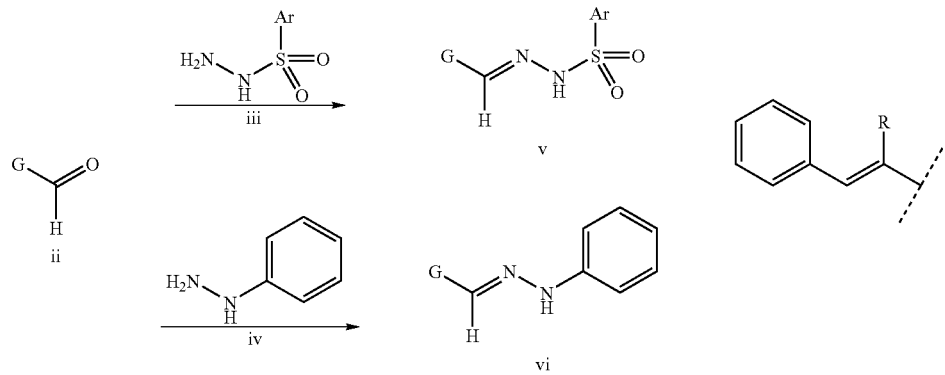

e.g. G = COOH,

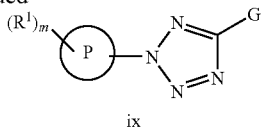

Tetrazoles of formula ix may also be prepared from the reaction of an arylhydrazone of formula vi with an aryl azide of formula xi, in a suitable solvent such as ethanol or pyridine. [J. Med. Chem. 1978, 21, 1254-60] Aryl azides of formula xi may be formed using sodium azide with an aryl diazonium salt of formula x, which may in turn be prepared as described above from an aryl amine, for example aniline or 2,4,6-tribromoaniline. The aryl azide may be considered as a nitrogen transfer reagent since cycloaddition onto the hydrazone is followed by elimination to regenerate the aryl amine precursor to diazonium salt x.

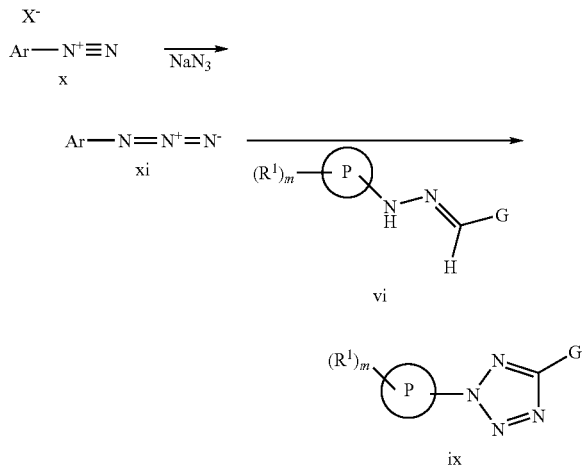

Typically, G is a group which may be employed as a precursor to the $X^1$—$X^2$-$Q(R^2)_p$ moiety in compounds of formula I, such as an olefin or carboxylic acid or acid derivative. When G is an aryl olefinic compound of formula xii, derived for example from cinnamaldehyde where $R^3$ is H, the olefin group can be cleaved to provide an aldehyde of formula xiii directly in a one-pot process using a reagent such as ozone or via the diol using a dihydroxylation reagent such as osmium tetroxide followed by subsequent cleavage using a reagent such as lead (IV) acetate. When a substituted cinnamaldehyde is employed the reaction to produce compounds of formula xii, such as α-methylcinnamaldehyde wherein $R^3$ is methyl, a ketone would result from the cleavage of the olefin. [J. Med. Chem. 2000, 43, 953-970; Adv. Synth. Catal. 2002, 344, 421-433; "Oxidations in Organic Chemistry", M. Hudlicky, ACS Monograph 186, (1990)]

Aldehydes of formula xiii wherein $R^3$ is H may be reduced to primary alcohols of formula xv wherein $R^3$ and $R^4$ are H, using well known reducing agents such as sodium or lithium borohydride, in a solvent such as methanol, THF or DMF at temperatures between 0-80° C. Secondary alcohols wherein $R^4$ is not H may also be formed from aldehydes of formula xiii via addition reactions of an organometallic reagent, for example Grignard reagents $R^4MgX$, in a solvent such as THF at temperatures between -78° C. to 80° C., and are typically performed between 0° C. and room temperature. Similarly, ketones of formula xiii, wherein $R^3$ is not H, may be employed to form secondary or tertiary alcohols of formula xv by reduction or addition of an organometallic reagent. Primary alcohols of formula xv, wherein $R^3$ and $R^4$ are H, are also available from compounds of formula xiv, by reduction of acid or ester derivative using reducing agents such as lithium borohydride in a suitable solvent such as THF or DMF at temperatures in the range of 20-80° C. Ketones of formula xiii are obtained by treatment of carboxylic acid esters with the appropriate carbon nucleophile, such as Grignard reagents $R^3MgX$ according to standard protocols. [J. Med. Chem. 1978, 21, 1254-60; J. Med. Chem. 1993, 36, 2676-2688; Can. J. Chem. 1995, 73, 885-895]

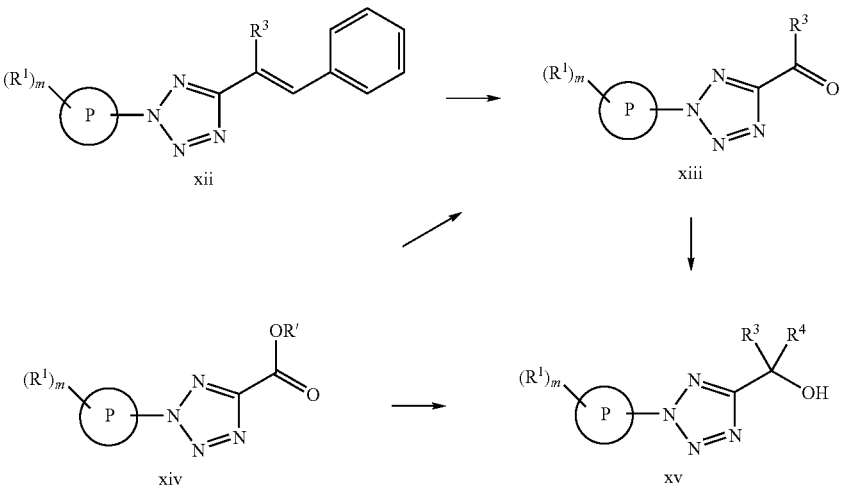

Enantiomerically pure or enriched products, as depicted in scheme 4a ($R^7$ is Me or Et; $X^3$ and $X^4$ as defined in formula I) are obtained by kinetic resolution of racemic or scalemic secondary alcohols using enzyme-catalyzed acetylation with for example polymer bound *Candida Antarctica* Lipase (Novozyme 435®), or other esterases, for example *Candida rugosa* or *Pseudomonas fluorescens*, in organic solvents such as toluene, tert-butyl methyl ether, tert-butanol or DCM at temperatures from 0 to 90° C., using acetylating reagents such as vinyl acetate, other substituted alkyl acetates, pentafluorophenyl acetate or nitro- or halophenyl acetates, which yields the enriched (R)-acetate and the enriched (S)-alcohol. The (R)-acetate may be hydrolyzed to the corresponding alcohol by e.g. lithium hydroxide in mixtures of THF and water or by any other methods as described herein below, to yield the opposite enantiomerically enriched or pure alcohol.

Scheme 4a

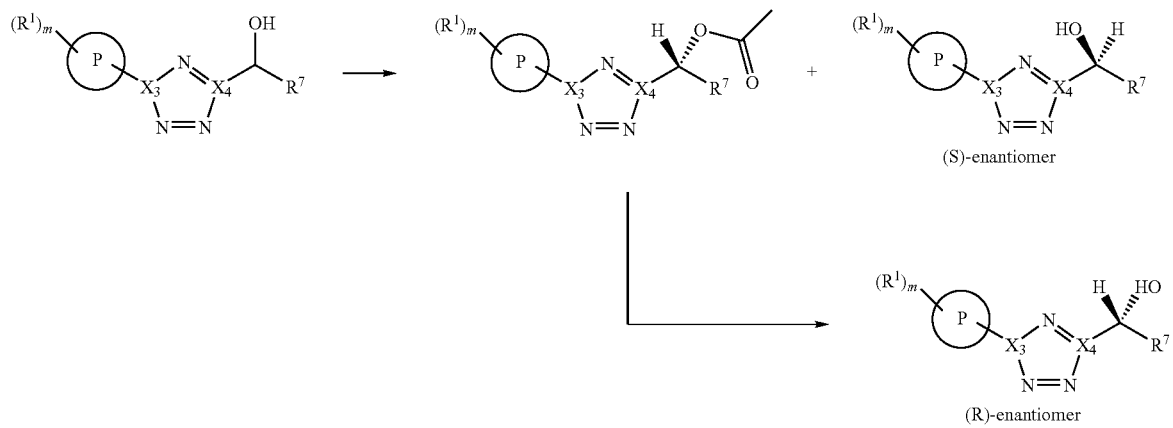

Alcohols of formula xv may be converted by standard methods to compounds of formula xvi wherein LG is a leaving group. Compounds of formula xvi wherein LG is a halide are formed by the use of reagents such as triphenylphosphine in combination with a halide source such as iodine, N-bromosuccinimide or N-chlorosuccinimide, or alternatively by treatment with tribromophosphine or thionyl chloride. The alcohol moiety in compounds of formula xv may also be transformed to leaving groups LG such as mesylates or tosylates by employing the appropriate sulfonyl halide or sulfonyl anhydride in the presence of a non-nucleophilic base to obtain the corresponding sulfonates. Chlorides or sulfonates can be converted to the corresponding bromides or iodides by treatment with bromide salts, for example LiBr, or iodide salts, such as LiI.

Scheme 5

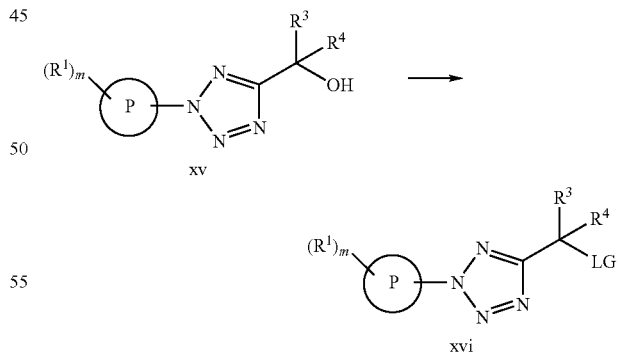

Amine intermediates of formula xvii may be formed using compounds of formula xvi wherein LG represents a leaving group, by displacement of said leaving group using a primary amine, $NH_2R^3$ or source of ammonia when $R^3$ is H, or may be formed using the corresponding carbonyl compounds of formula xiii via reductive amination using an amine, $NH_2R^3$, in the presence of a suitably mild reducing agent such as $NaBH_3CN$ or $NaBH(OAc)_3$ in a suitable solvent such as THF, methanol or 1,2-dichloroethane.

Scheme 6

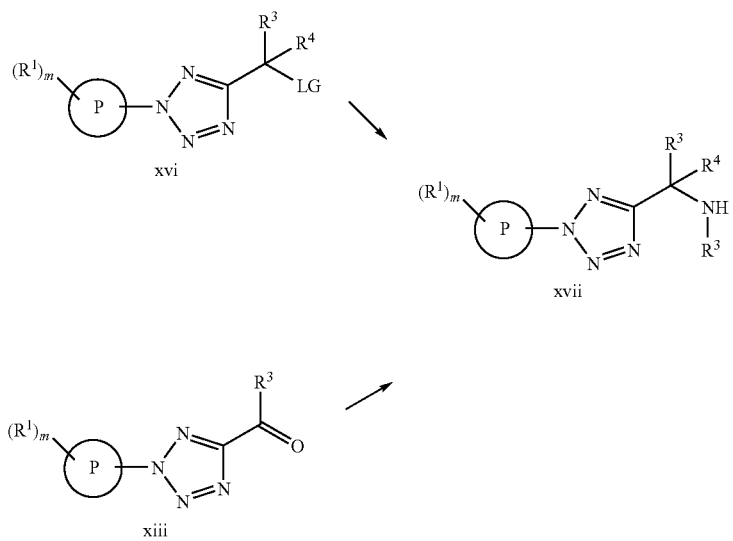

Compounds of formula xxiii containing the dihydro[1,2,4] triazole-3-thione ring may be prepared by initial N-acylation of a 4-alkylthiosemicarbazide of formula xix, using any suitable acylating agent of formula xviii in a suitable solvent, for example pyridine DMF, DCM, THF, or acetonitrile at a temperature from −20 to 100° C. A pre-formed acylating agent such as an acid halide may be employed, or an acid may be activated in situ by the treatment with standard activating reagents such as DCC, DIC, EDCl or HBTU, with or without the presence of co-reagents such as HOBt or DMAP. Formation of the acyclic intermediate xxii is followed by alkaline ring closure either spontaneously under the conditions of the acylation, or by heating at 50 to 150° C. in pyridine or in aqueous solvents in the presence of a base, such as NaOH, $NaHCO_3$ or $Na_2CO_3$, with or without co-solvents such as dioxane, THF, MeOH, EtOH or DMF. The acyclic intermediate of formula xxii can also be formed by treatment of an acyl hydrazide of formula xx with a suitable isothiocyanate of formula xxi in a suitable solvent, for example 2-propanol, DCM, THF or the like at temperatures in the range of −20 to 120° C.

Scheme 7

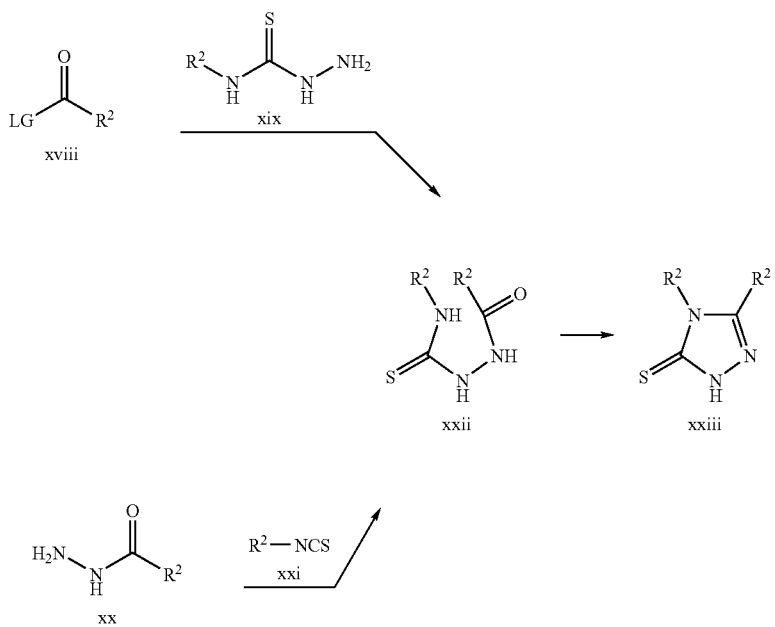

Compounds of formula xxiii may be converted to compounds of formula xxv by initial alkylation of the sulphur atom to form intermediates of formula xxiv using primary alkyl halides such as MeI and EtI (alkyl is Me and Et respectively) in MeOH, EtOH, THF, acetone or the like at −30 to 100° C., followed by oxidation of intermediates xxiv using for example KMnO₄ in mixtures of water and acetic acid, or MCPBA in DCM, at −20 to 120° C., or by using any other suitable oxidant.

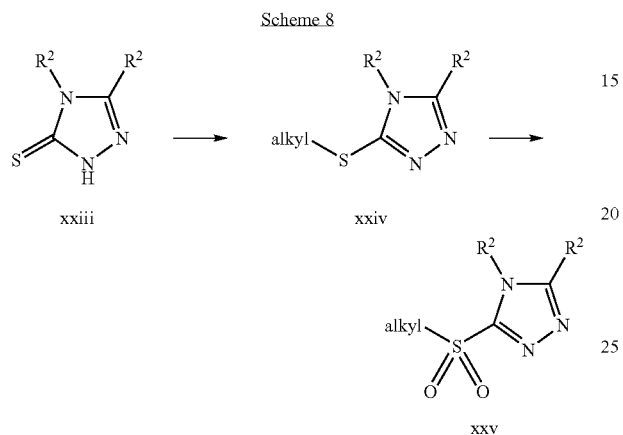

Scheme 8

3-Amino[1,2,4]triazole compounds of formula xxix, wherein the $R^{x'}$ and $R^x$ groups are equivalent to $R^2$ and $R^3$ in compounds of formula I wherein Q is a monocyclic triazole ring or may together form a ring leading to compounds of formula I wherein the Q group is a bicyclic system containing a fused triazolo ring, may be obtained by treating isothioureas of formula xxvi with either an acyl hydrazide of formula xxvii or in a stepwise manner by treatment with hydrazine followed by an acylating agent of formula xviii. The intermediates of formula xxviii may form a triazole ring by heating at 50 to 200° C. in a suitable solvent such as pyridine or DMF. Due to the possibility for cyclization of both NHR$^x$ groups in compounds of formula xxviii, this reaction works best when symmetrical thioureas are used to avoid a mixture of isomers that may occur when the R$^x$ groups are not identical. When unsymmetrical thioureas are used, the isomers may be separated by chromatographic purification.

The reaction of isothioureas of formula xxvi, in which the S-alkyl (for example S-Me or S-Et) moiety acts as a leaving group upon treatment with hydrazine or acyl hydrazide nucleophile, may be carried out in solvents such as pyridine, methanol, ethanol, 2-propanol, THF or the like at temperatures between −20 to 180° C. In the two-step process, the acylation may be carried out in suitable solvent such as THF, pyridine or DMF at −20 to 100° C. As described above, the leaving group LG in acylating agent xviii may include chloro or any other suitable leaving group such as that generated by in situ treatment of the corresponding acid with standard activating reagents. Isothioureas of formula xxvi may be obtained by S-alkylation of the corresponding thioureas with an alkyl halide, for example MeI or EtI, in a suitable solvent such as acetone, EtOH, THF, DCM or the like at temperatures between −100 to 100° C.

Carbon-substituted triazoles of formula xxxiii may be prepared in a similar manner by employing an amide of formula xxx. The amide group may be activated using a reagent such as POCl₃ or Me₃OBF₄ to generate compounds of formula xxxi such as chloroimidates (LG=Cl) or methoxyimidates (LG=OMe). Similar to isothioureas of formula xxvi above, compounds of formula xxxi may react with an acyl hydrazide or hydrazine followed by an acylating agent to generate intermediate xxxii, which may be closed to the triazole spontaneously or by heating. Fused [1,2,4]triazoles wherein the R$^x$ and R$^{x'}$ groups together form a 5-7 membered ring may be obtained by employing a suitable cyclic lactam instead of an acyclic amide. Such lactam imidates are available from their corresponding lactams by treatment with Me₃OBF₄ or dimethylsulfate. [Org. Prep. Proced. Int; 24, 1992, pp. 147-158 or Tetrahedron Lett. 42, 2001, pp. 173-1776]

Scheme 9

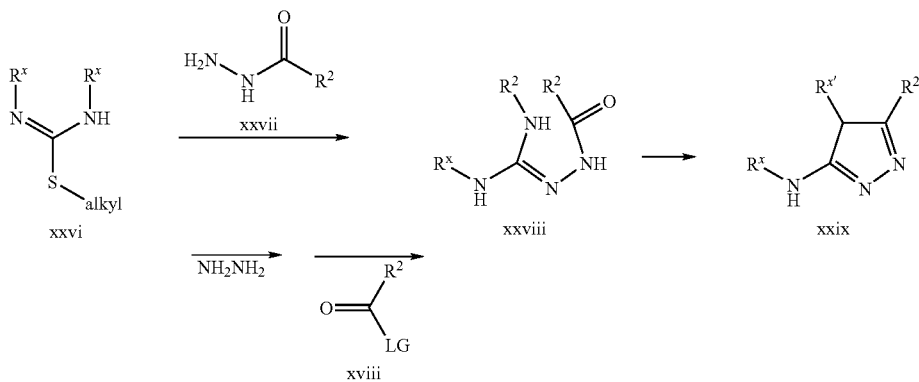

Scheme 10

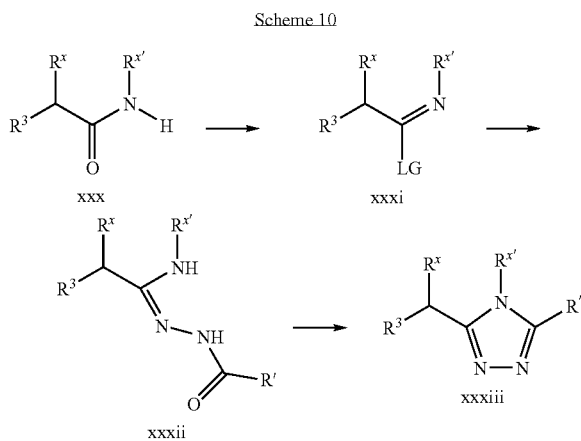

Compounds of formula xxiii may be converted to compounds of formula xxxiv by reduction of the thione moiety using a suitable reducing agent such as Raney Nickel, in a suitable solvent such as ethanol at a temperature between 50 to 100° C., and are typically carried out at 65° C. Compounds of formula xxxv are available from compounds of formula xxxiv by treatment with an aldehyde, for example formaldehyde, in a suitable solvent such as water at a temperature between room temperature to 100° C., and are typically carried out at 37° C. when aqueous formalin is used as the source of formaldehyde. The resulting alcohols of formula xxxv may be oxidized to provide aldehydes or ketones of formula xxxvi using oxidation procedures well known to the one skilled in the art, such as the employment of $MnO_2$ as oxidant, or by Swern oxidation. Alternatively, compounds of formula xxxvii wherein leaving group such as a halide may be prepared from compounds of formula xxxv as described above for alcohols of formula xv.

Scheme 11

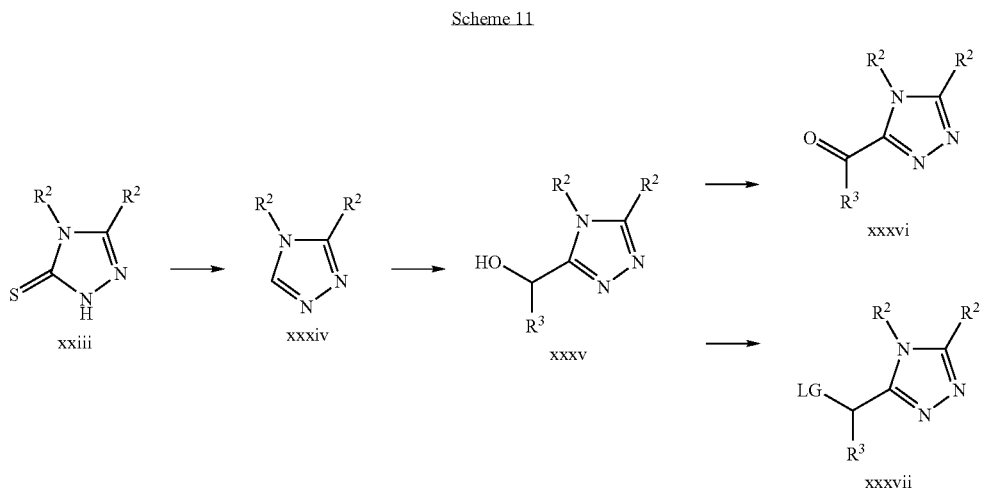

Examples of compounds of formula I wherein Q is comprised of a monocyclic group include bis amines such as piperazine and homopiperazine, that are connected to $X^1$ or $X^2$ by one N atom in the ring Q. Bis amines such as N-monosubstituted piperazines or piperazines which contain the $R^2$ moiety may be commercially available or may be prepared using methods known to one skilled in the art. Such compounds that are not available commercially may be prepared from amino acids via intermediates such as diketopiperazines, which may be reduced to amines such as piperazines. In certain reactions known to one skilled in the art, protection of the bis amine of Q is not required and the free amino compound may be used directly, for example in the displacement of the leaving group in compounds of formula xvi. In such cases, or in cases when the protecting group is removed, the free amine may be used to introduce the $R^2$ substituent in compounds of formula xxxviii, since such amines may be employed as nucleophiles in reactions with many types of electrophiles, such as alkyl halides, acid chlorides or anhydrides, chloroformates, carbamoyl chlorides, sulfonyl chlorides, isocyanates, isothiocyanates and the like. Compounds of formula xxxviii may also be obtained from carbonyl compounds of formula xiii using reductive amination conditions as described above for formation of compounds of formula xvii.

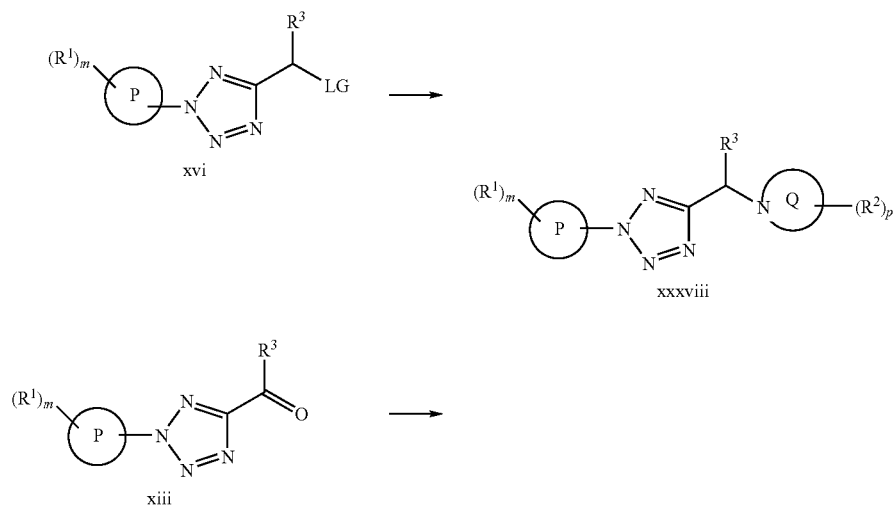

When Q in formula I is a cyclic diamine such as piperazine and R3 is aryl or heteroaryl, the required nucleophilic reagents (W=H or protecting group) may be prepared by coupling to an aryl halide with the cyclic diamine nucleophile, as shown in Scheme 12a. When the aryl group contains an activating group such as the presence of an adjacent N such as in 2-pyridine (X=N, other=CR), 2-pyrimidine (X=X$^5$=N or X=X$^3$=N) or 2-pyrazine (X=X$^4$=N), the reaction is facilitated and may occur under heating without additional catalyst. In the presence of additional activating electron withdrawing groups such as ortho or para NO$_2$ or CN, the reaction may occur at a lower temperature. Aromatic nucleophilic displacement with less reactive phenyl halides may be accomplished by addition of a suitable catalyst/ligand system {Urgaonkar, S.; Xu, J.-H.; Verkade, J. G. J. Org. Chem. 2003, 68, 8416; Urgaonkar, S.; Nagarajan, N.; Verkade, J. G. Org. Lett. 2003, 5, 815).

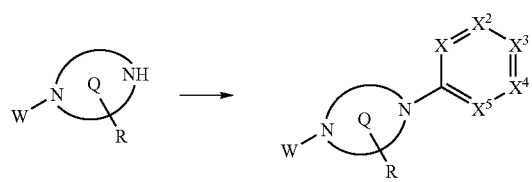

The Q ring may be constructed from compounds of formula xvii containing a primary amine moiety via any compatible method. One such method wherein the Q ring is a monocyclic bis amine such as piperazine involves ring construction by displacement of two leaving groups from a compound such as that shown in formula xxxix [Bioorg. Med. Chem. Lett. 2002, 12,791-794; Bioorg. Med. Chem. Lett. 2002, 12, 3195-3198; Synthesis 1990, 10, 925-930; J. Org. Chem. 1990, 55, 1684-1687].

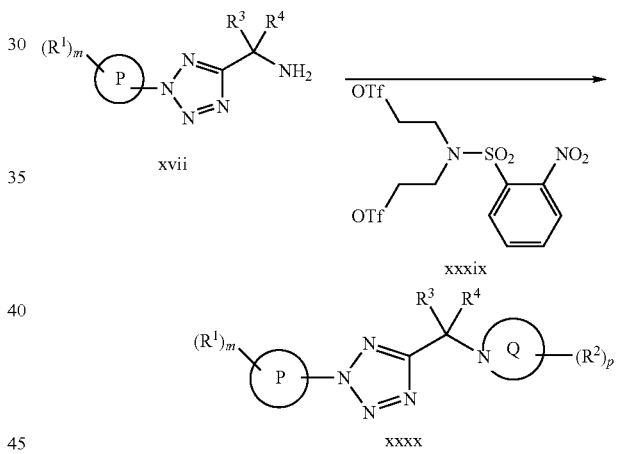

Compounds of formula xvii containing a secondary amine are ideally suited for construction of 3-amino-[1,2,4]triazoles asymmetrically substituted on the 3-amino substituent and the 4-N of the triazole ring. Amines of formula xvii may be converted to a wide variety of thioureas of formula xxxxi by reaction with a suitable isothiocyanate in a suitable solvent such as methanol, ethanol and the like, at a temperature between room temperature and 100° C., and are typically carried out at 60° C. Thioureas of formula xxxxi may be converted to compounds of formula xxxxii by conversion to an isothiourea, followed by reaction with an acyl hydrazine and cyclization to the amino triazole as was described above for xxix. In this case since the required (R$^1$)$_m$—P—CR$^3$R$^4$ group from formula I is already contained in the amine and the amine is secondary, the triazole cyclization has only one option to react through the NHR$^2$ moiety forming compounds of formula xxxxii and not the isomeric triazole.

Scheme 14

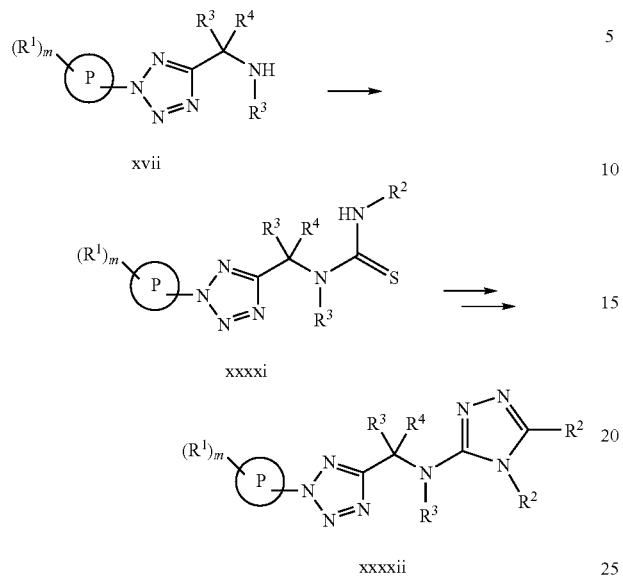

Compounds of formula xxxxii (wherein $X^2$ as drawn in formula I is $NR^3$) may also be prepared by displacement of the leaving group from compounds of formula xvi using a suitable 3-amino[1,2,4]triazole of formula xxix, including those monocyclic triazoles wherein $R^x$ groups become $R^3$ and $R^2$ and those fused triazoles wherein both $R^x$ groups together form a ring, with a strong base such as sodium hydride, in a solvent such as DMF at temperatures between room temperature to 100° C., and are typically performed between 60-80° C.

Scheme 15

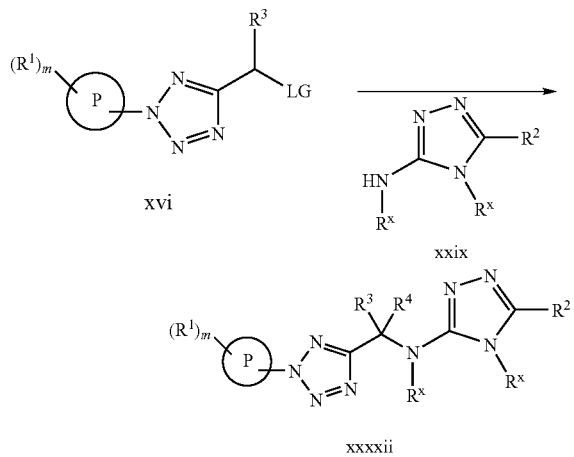

Similarly, compounds of formula xxxxiii (wherein $X^2$ as drawn in formula I is S) may also be prepared by displacement of the leaving group in compounds of formula xvi using a suitable nucleophile such as the dihydro-[1,2,4]triazole-3-thiones which react through their tautomeric [1,2,4]triazole-3-thiol form in the presence of a base such as potassium carbonate or triethylamine, in a suitable solvent such as acetonitrile or DMF, at temperatures between room temperature to 100° C., and are typically performed at room temperature.

Scheme 16

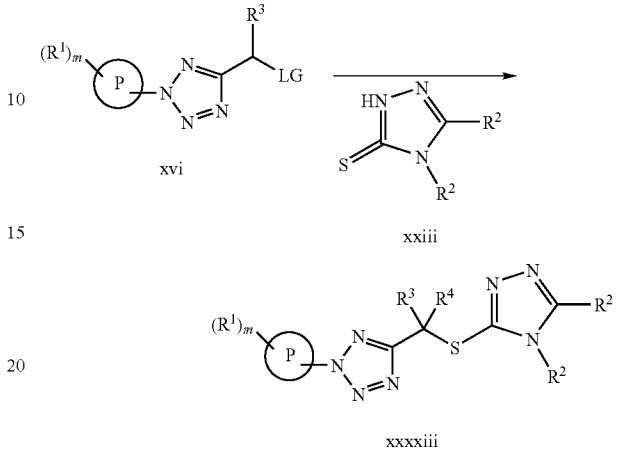

Compounds of formulae xxxxv and xxxxvi (wherein $X^2$ as drawn in formula I is $CR^3R^4$) may also be prepared by displacement of the leaving group in compounds of formula xvi or addition to the carbonyl moiety in compounds of formula xiii using a suitable carbon nucleophile such as contained in a compound of formula xxxxiv, $M\text{-}CR^3R^4\text{-}Q\text{-}(R_2)_p$ wherein M is a metal containing species such as Li or MgBr. Such a carbanion may be generated by deprotonation when Q is able to stabilize said carbanion, such as when Q is an aromatic heterocycle such as triazole, using a stronger base, such as n-butyllithium or tert-butyllithium, or from a insertion of a metal into a carbon-halogen bond such as occurs when a Grignard reagent is created from a compound of formula xvi (LG=Br). Carbanions may be generated and used in ethereal solvents such as THF and diethyl ether alone or as mixtures with alkanes such as pentane or hexane, at temperatures ranging from –78° C. to 80° C., and are typically initiated at –78° C. and gradually allowed to warm to room temperature after addition of the compound of formula xvi. The reaction of a carbanion with a benzylic mesylate or halide leaving group may be facilitated by addition of a copper salt to generate an organocuprate, whereas a Grignard reagent favors 1,2-addition to a carbonyl even when other options are possible. Similarly alcohols of formula xxxxix may be prepared by the addition of a Grignard reagent of formula xxxxvii, available from compounds of formula xvi (LG=Br), to a carbonyl compound of formula xxxxviii, which for example is equivalent to compounds of formula xxxvi when Q is a triazole.

Scheme 17

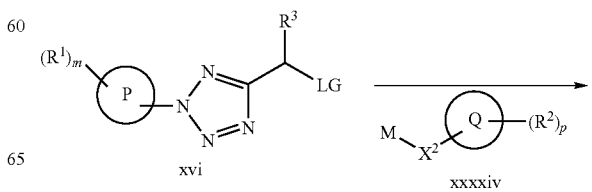

-continued

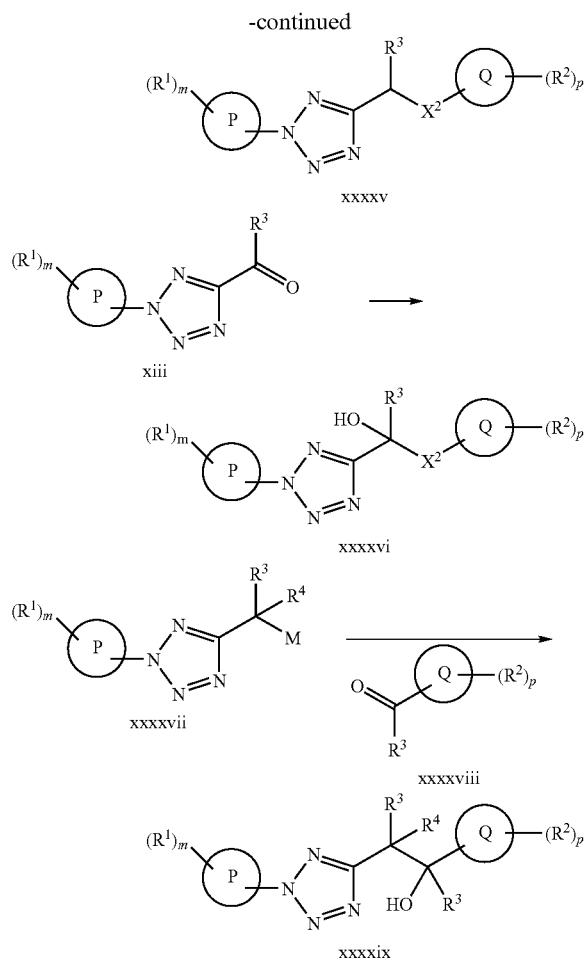

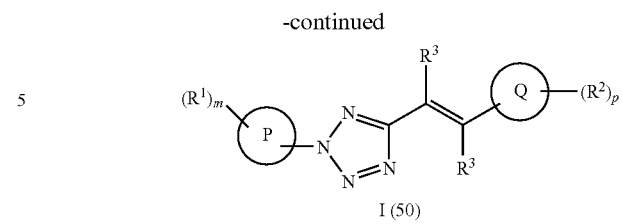

Olefinic compounds of formula 1 may be reduced by employing hydrogen in the presence of a metal catalyst such as palladium on carbon in a suitable solvent such as ethyl acetate or ethanol. Alternatively, such olefinic compounds may be reduced by the addition of a suitable reagent, such as dialkylboranes $R_2BH$ or trialkylsilylane $R_3SiH$, to the olefin, followed by reductive cleavage of the newly formed bonds. Such intermediates may also be employed in other reactions such as oxidation to generate alcohols of formula xxxxvi or xxxxix.

Scheme 19

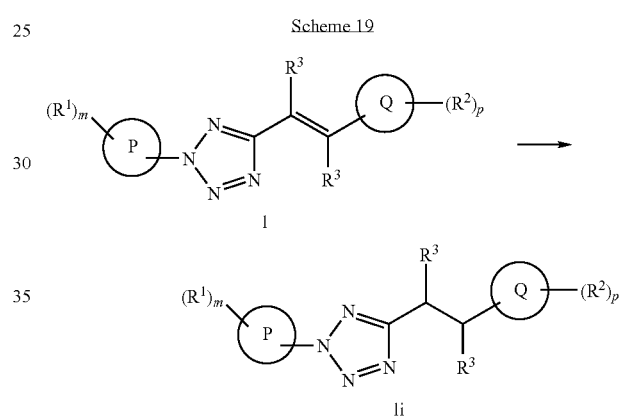

Compounds of formula 1 wherein $X^1$ is a $C_2$-alkenyl and $X^2$ is a bond, may be prepared from Wittig reagents generated by treatment of compounds of formula xvi (LG=Br) with a phosphorus reagent such as $PPh_3$, in a solvent such as toluene at a temperature between 50 to 100° C., typically at 80° C., followed by treatment of the resulting phosphonium bromide salt with a carbonyl compound of formula xxxxviii, for example when Q is triazole a compound of formula xxxxvi, in the presence of a base such as DBU, in a solvent such as DMF at a temperature between 50 to 100° C., typically at 80° C. similarly to the above reactions of Grignard and aldehyde to produce xxxxvi and xxxxix, the partners may be reversed, resulting in this case the same compound 1 due to the symmetry of the bond forming reaction.

Analogous compounds of formula lii and liii may also be available by reduction of the alcohol moiety in compounds of formula xxxxvi and xxxxix using a suitable reducing agent, for example a trialkyl- or triaryl-silane in the presence of an acid such as trifluoroacetic acid, either neat or in a suitable solvent such as dichloromethane or benzene at a temperature between room temperature and 80° C., preferably at 40° C.

Scheme 18

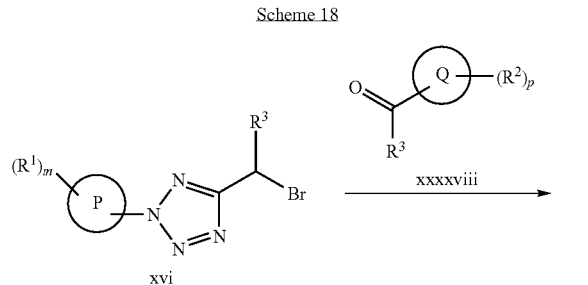

Scheme 20

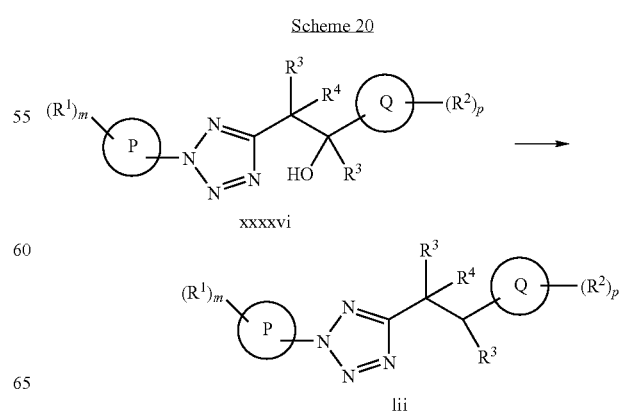

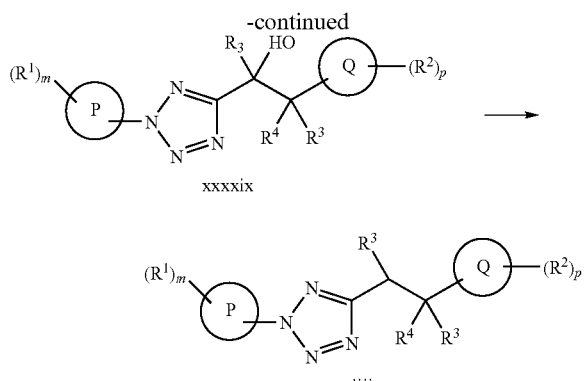

xxxxix

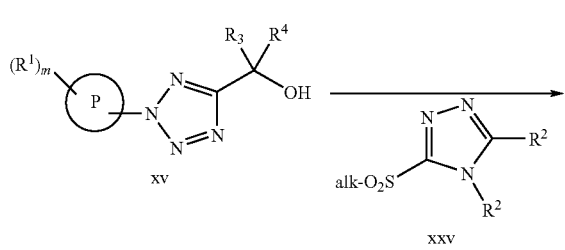

liii

Compounds of formula liv (wherein $X^2$ is O as drawn in formula I and R3=Me or Et and R4=H) may be prepared by bond formation through nucleophilic replacement of a leaving group such as alk-$SO_2$ from compounds of formula xxv wherein Q is triazole, by an alcohol or alkoxide nucleophile under basic conditions. The base used may include strong hydridic bases, for example, NaH or milder bases, such as $Cs_2CO_3$, at temperatures from 0 to 80° C. in polar aprotic solvents such as DMF or acetonitrile, whereas for enantiomerically enriched or pure compound xv (R4=H) the preferred base is $Cs_2CO_3$ in order to obtain enantiomerically pure products liv directly. Other suitable leaving groups may include halogens, such as chloro or bromo.

Scheme 21

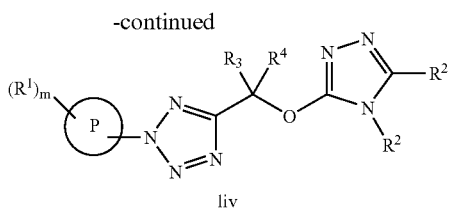

liv

Compounds of formula lviii wherein the tetrazole ring is reversed compared to all previous compounds described and $X^1$ and $X^2$ are both $CR^3R^4$, may be prepared by nucleophilic reactions of a suitably substituted aryl tetrazole of formula lv with a suitable electrophilic reagent of formula lvi. When such an intermediate is available, it may be employed directly in the reaction with the aryl tetrazole of formula lv, producing compounds of formula lvii directly. [J. Med. Chem. 1967, 10, 400-402, Pharm. Chem. J. (English Translation) 1993, 27, 204-209]. When such an intermediate is not available, other electrophilic reagents wherein G is a group which may later be converted to the Q-$(R^2)_p$ moiety may be employed leading to intermediates of formula lvi. [J. Med. Chem. 1995, 38, 4786-4792; J. Med. Chem. 1992, 35, 1191-1200; J. Med. Chem. 1992; 35, 1200-1209] For example, an aryl tetrazole of formula lv may add in the 1,4- or Michael sense to an olefinic compound conjugated to an electron withdrawing G group for example, nitrile, aldehyde, ester and the like, yielding a compound of formula lvii, wherein some of the $R^3$ and $R^4$ substituents may be H due to the valency requirements of the olefin or the reactivity of said electrophilic olefinic. Several non-limiting examples of electrophiles are listed in the scheme below containing a true leaving group LG such as a mesylate or halide. In such cases, G may also be a —$CH_2OPG$ group (or an equivalent thereof). Alternatively, an internal leaving group X such as an epoxide or activated aziridine wherein the X group is retained in the compound of formula lvii may be employed. When Q contains a triazole ring, methods that have been described for preceding examples may be employed.

Scheme 22

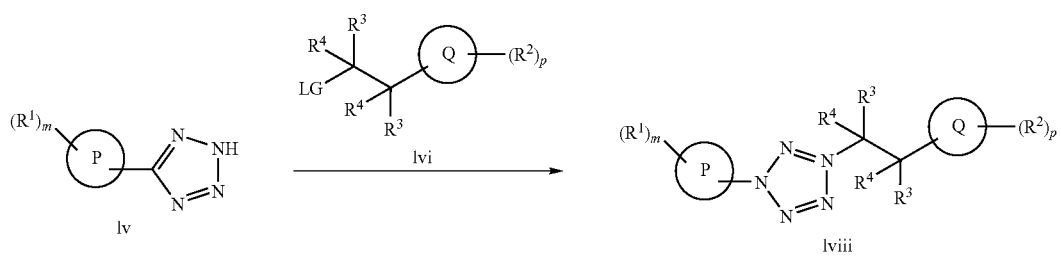

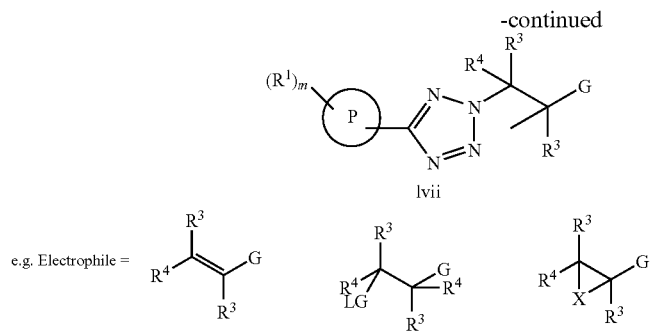

It is to be understood by one skilled in the art that when incompatible functional groups are present, such groups may be suitably protected to allow the reaction to proceed. It is also to be understood that products of formula I can also be converted to other products of formula I when suitable functional groups are present. Several non-limiting examples are listed here. When $X_2$ is S, the sulfide of formula I may be oxidized to the sulfoxide and sulfone. When an aryl halide such as iodide or bromide is present, transition metal catalysts such as palladium (0) tetrakis triphenylphosphine may effect transformation of such aryl iodides and bromides to groups such as cyano, alkenyl and aryl or heteroaryl in the presence of suitable coupling agents. When a suitable alcohol or secondary or primary amine is present in formula I, such groups may be alkylated or acylated.

The invention further relates to the following compounds, which may be used as intermediates in the preparation of the compound of formula I;

Cinnamaldehyde tosyl hydrazone
2-(3-Chloro-phenyl)-5-styryl-2H-tetrazole
2-(5-Chloro-2-fluoro-phenyl)-5-styryl-2H-tetrazole
5-Styryl-2-m-tolyl-2H-tetrazole
2-(3-Iodo-phenyl)-5-styryl-2H-tetrazole
3-(5-Styryl-tetrazol-2-yl)-benzonitrile
2-(2-Fluoro-5-methyl-phenyl)-5-styryl-2H-tetrazole
1-[2-(3-chloro-phenyl)-2H-tetrazol-5-yl]-2-phenyl-ethane-1,2-diol
1-[2-(5-Chloro-2-fluoro-phenyl)-2H-tetrazol-5-yl]-2-phenyl-ethane-1,2-diol
1-Phenyl-2-(2-m-tolyl-2H-tetrazol-5-yl)-ethane-1,2-diol
1-[2-(3-Iodo-phenyl)-2H-tetrazol-5-yl]-2-phenyl-ethane-1,2-diol
3-[5-(1,2-Dihydroxy-2-phenyl-ethyl)-tetrazol-2-yl]-benzonitrile
1-[2-(2-Fluoro-5-methyl-phenyl)-2H-tetrazol-5-yl]-2-phenyl-ethane-1,2-diol
2-(3-Chloro-phenyl)-2H-tetrazole-5-carbaldehyde
2-(5-Chloro-2-fluoro-phenyl)-2H-tetrazole-5-carbaldehyde
2-m-Tolyl-2H-tetrazole-5-carbaldehyde
2-(3-Iodo-phenyl)-2H-tetrazole-5-carbaldehyde
3-(5-Formyl-tetrazol-2-yl)-benzonitrile
2-(2-Fluoro-5-methyl-phenyl)-2H-tetrazole-5-carbaldehyde
[2-(3-Chloro-phenyl)-2H-tetrazol-5-yl]-methanol
[2-(5-Chloro-2-fluoro-phenyl)-2H-tetrazol-5-yl]-methanol
(2-m-Tolyl-2H-tetrazol-5-yl)-methanol
[2-(3-Iodo-phenyl)-2H-tetrazol-5-yl]-methanol
3-(5-Hydroxymethyl-tetrazol-2-yl)-benzonitrile
[2-(2-Fluoro-5-methyl-phenyl)-2H-tetrazol-5-yl]-methanol
1-[2-(3-chloro-phenyl)-2H-tetrazol-5-yl-ethanol
1-[2-(5-Chloro-2-fluoro-phenyl)-2H-tetrazol-5-yl]-ethanol
1-(2-m-Tolyl-2H-tetrazol-5-yl)-ethanol
1-[2-(3-Iodo-phenyl)-2H-tetrazol-5-yl]-ethanol
3-[5-(1-Hydroxy-ethyl)-tetrazol-2-yl]-benzonitrile
1-[2-(2-Fluoro-5-methyl-phenyl)-2H-tetrazol-5-yl]-ethanol
5-Bromomethyl-2-(3-chloro-phenyl)-2H-tetrazole
Methanesulfonic acid 1-[2-(3-chlorophenyl)-2H-tetrazol-5-yl]-ethyl ester
Methanesulfonic acid 2-(5-chloro-2-fluoro-phenyl)-2H-tetrazol-5-ylmethyl ester
Methanesulfonic acid 1-[2-(5-chloro-2-fluoro-phenyl)-2H-tetrazol-5-yl]-ethyl ester
Methanesulfonic acid 2-m-tolyl-2H-tetrazol-5-ylmethyl ester
Methanesulfonic acid 1-(2-m-tolyl-2H-tetrazol-5-yl)-ethyl ester
Methanesulfonic acid 2-(3-cyano-phenyl)-2H-tetrazol-5-ylmethyl ester
Methanesulfonic acid 1-[2-(3-cyano-phenyl)-2H-tetrazol-5-yl]-ethyl ester
Methanesulfonic acid 2-(2-fluoro-5-methyl-phenyl)-2H-tetrazol-5-ylmethyl ester
Methanesulfonic acid 1-[2-(2-fluoro-5-methyl-phenyl)-2H-tetrazol-5-yl]-ethyl ester
Methanesulfonic acid 2-(3-iodo-phenyl)-2H-tetrazol-5-ylmethyl ester
Methanesulfonic acid 1-[2-(3-iodo-phenyl)-2H-tetrazol-5-yl]-ethyl ester
4-Methyl-5-pyridin-4-yl-2,4-dihydro-[1,2,4]triazole-3-thione
4-Ethyl-5-pyridin-4-yl-2,4-dihydro-[1,2,4]triazole-3-thione
4-Cyclopropyl-5-pyridin-4-yl-2,4-dihydro-[1,2,4]triazole-3-thione
4-(4-Methyl-5-methylsulfanyl-4H-[1,2,4]triazol-3-yl)-pyridine
4-(4-Cyclopropyl-5-methylsulfanyl-4H-[1,2,4]triazol-3-yl)-pyridine
4-(5-Methanesulfonyl-4-methyl-4H-[1,2,4]triazol-3-yl)-pyridine
4-(4-Cyclopropyl-5-methanesulfonyl-4H-[1,2,4]triazol-3-yl)-pyridine
Methyl-(4-methyl-5-pyridin-4-yl-4H-[1,2,4]triazol-3-yl)-amine
3-Pyridin-4-yl-5,6,7,8-tetrahydro-[1,2,4]triazolo[4,3-a]pyrimidine
2-(methylthio)-4,5,6,7-tetrahydro-1H-1,3-diazepine
1,3-diazepan-2-onehydrazonehydroiodide
3-pyridin-4-yl-6,7,8,9-tetrahydro-5H-[1,2,4]triazolo[4,3-a][1,3]diazepine
4-(4-Ethyl-4H-[1,2,4]triazol-3-yl)-pyridine
(4-Ethyl-5-pyridin-4-yl-4H-[1,2,4]triazol-3-yl)-methanol
4-Ethyl-5-pyridin-4-yl-4H-[1,2,4]triazole-3-carbaldehyde The invention will now be illustrated by the following non-limiting examples.

General Methods

All starting materials are commercially available or earlier described in the literature. The $^1$H and $^{13}$C NMR spectra were recorded either on a Brucker 400 or a Varian 400 at 400 MHz and 100 MHz, respectively. The mass spectra were recorded utilising electrospray (LC-MS; LC: Waters 2790, column XTerra MS C$_8$ 2.5 µm 2.1×30 mm, buffer gradient H$_2$O+0.1% TFA:CH$_3$CN+0.04% TFA, MS: micromass ZMD) ionisation techniques.

EXAMPLE 1 a) Cinnamaldehyde tosyl hydrazone

Cinnamaldehyde (8.80 g, 66.59 mmol) was added to p-toluene sulfonamide (12.44 g, 66.79 mmol) in ethanol (70 mL). The reaction immediately turned solid and ethanol (20 mL) was again added. The reaction was allowed to stir at room temperature for one hour and was then filtered. The solid was washed with methanol and dried by reduced pressure to yield the title compound as a white solid (17.5 g, 87%). $^1$H NMR (CDCl$_3$) δ (ppm): 8.23 (s, 1H), 7.88 (d, 2H), 7.60 (d, 1H), 7.34 (m, 6H), 6.83 (m, 2H), 2.43 (s, 3H).

b) α-Methyl-cinnamaldehyde tosyl hydrazone

The title compound (32.2 g, 61%, white solid) was prepared by adding α-methylcinnamaldehyde (15 g, 102.6 mmol) to p-toluene sulfonamide (19.2 g, 102.9 mmol) in ethanol (100 mL), followed by removal of the solvent in vacuo to aid precipitation, and collection of the solid by filtration and the solid obtained was dried under reduced pressure. $^1$H NMR (CDCl$_3$) δ (ppm): 7.90 (s, 2H), 7.87 (s, 1H), 7.55 (s, 1H), 7.34 (m, 7H), 6.65 (s, 1H), 2.45 (s, 3H), 2.08 (s, 3H).

EXAMPLE 2 a) 2-(3-Chloro-phenyl)-5-styryl-2H-tetrazole

An aqueous (5 mL) solution of sodium nitrite (540.9 mg, 7.839 mmol) was added to a solution of 3-chloroaniline in water (7 mL), concentrated hydrochloric acid (3 mL) and ethanol (7 mL) via dropping funnel. The reaction was allowed to stir at 0° C. for ten minutes. This solution was poured into a dropping funnel and ice was added. This was added dropwise to a solution of cinnamaldehyde tosyl hydrazone (2.3 g, 7.682 mmol) in pyridine (20 mL). This was allowed to stir overnight. An aqueous workup was done extracting with dichloromethane three times. The combined layers were washed with brine, dried over sodium sulfate, filtered and concentrated. The crude product was purified by column chromatography (20% EtOAc/hexanes) to yield the title compound as a light purple solid (433.6 mg, 19%). $^1$H NMR (CDCl$_3$) δ (ppm): 8.21 (m, 1H), 8.09 (d of t, 1H), 7.89 (d, 1H), 7.61 (m, 2H), 7.49 (m, 5H), 7.24 (d, 1H).

Examples 2b to 2g were prepared as described for example 2a.

b) 2-(5-Chloro-2-fluoro-phenyl)-5-styryl-2H-tetrazole

The title compound (200 mg, 16%, dark brown solid) was obtained by adding the diazonium salt prepared from 5-chloro-2-fluoro-aniline (0.46 mL, 4.07 mmol) with aqueous sodium nitrite (286 mg, 4.1 mmol in 3 mL water), hydrochloric acid (5.5 mL, 17.8 mmol) in ethanol (4 mL) to a solution of cinnamaldehyde tosyl hydrazone (1.202 g, 4.0 mmol) in pyridine (30 mL). The crude product was partially purified by column chromatography (5% EtOAc/hexanes) and used in the next step without additional purification.

c) 5-Styryl-2-m-tolyl-2H-tetrazole

The title compound (320 mg, 30%, dark yellow solid) was obtained by adding the diazonium salt prepared from m-tolylamine (0.44 mL, 4.1 mmol) with aqueous sodium nitrite (286 mg, 4.1 mmol in 3 mL water), hydrochloric acid (5.5 mL, 17.8 mmol) in ethanol (4 mL), to a solution of cinnamaldehyde tosyl hydrazone (1.207 g, 4.1 mmol) in pyridine (30 mL). The crude product was purified by column chromatography (3-6% EtOAc/hexanes). $^1$H NMR (CDCl$_3$) δ (ppm): 8.00 (s, 1H), 7.98 (d, 1H), 7.88 (d, 1H), 7.63 (m, 2H), 7.38-7.47 (m, 4H), 7.33 (d, 1H), 7.26 (d, 1H), 2.55 (s, 3H).

d) 2-(3-Iodo-phenyl)-5-styryl-2H-tetrazole

The title compound is obtained by adding the diazonium salt prepared from 3-iodo-phenylamine (1 mmol) with aqueous sodium nitrite (1 mmol in 0.75 mL water), hydrochloric acid (4.3 mmol in 1.3 mL water) in ethanol (1 mL), to a solution of cinnamaldehyde tosyl hydrazone (1 mmol) in pyridine (7.5 mL).

e) 3-(5-Styryl-tetrazol-2-yl)-benzonitrile

The title compound is obtained by adding the diazonium salt prepared from 3-aminobenzonitrile (1 mmol) with aqueous sodium nitrite (1 mmol in 0.75 mL water), hydrochloric acid (4.3 mmol in 1.3 mL water) in ethanol (1 mL), to a solution of cinnamaldehyde tosyl hydrazone (1 mmol) in pyridine (7.5 mL).

f) 2-(2-Fluoro-5-methyl-phenyl)-5-styryl-2H-tetrazole

The title compound is obtained by adding the diazonium salt prepared from 2-fluoro-5-methyl-phenylamine (1 mmol) with aqueous sodium nitrite (1 mmol in 0.75 mL water), hydrochloric acid (4.3 mmol in 1.3 mL water) in ethanol (1 mL), to a solution of cinnamaldehyde tosyl hydrazone (1 mmol) in pyridine (7.5 mL).

g) 2-(3-chlorophenyl)-5-[1-methyl-2-phenylvinyl]-2H-tetrazole

The title compound (3.82 g, 37%, orange solid) was obtained by adding the diazonium salt prepared from 3-chloro-aniline (4.15 mL, 39.2 mmol) with aqueous sodium nitrite (2.7 g, 39.2 mmol in 25 mL water), hydrochloric acid (45 mL, 180 mmol) in ethanol (35 mL) to a solution of cinnamaldehyde tosyl hydrazone (10.77 g, 34.25 mmol) in pyridine (50 mL). The crude product was partially purified by column chromatography (15% EtOAc/hexanes) and used in the next step without additional purification. $^1$H NMR (CDCl$_3$) δ (ppm): 8.22 (m, 1H), 8.11 (dt, 1H), 7.94 (br s, 1H), 7.50 (m, 6H), 7.31 (m, 1H), 2.50 (s, 3H).

EXAMPLE 3 a) 1-[2-(3-chloro-phenyl)-2H-tetrazol-5-yl]-2-phenyl-ethane-1,2-diol 2-(3-Chloro-phenyl)-5-styryl-2H-tetrazole (127.0 mg, 0.446 mmol) was weighed into a vial and citric acid (171.35 mg, 0.892 mmol) was added followed by a 1:1 mixture of t-butanol and water (3 mL). Potassium osmate oxide hydrate (0.3 mg) was added followed by 4-methyl morpholine N-oxide (in 1.5 mL of water) and the reaction was allowed to stir overnight. The reaction was filtered and washed with water and 1M hydrochloric acid to yield the title compound as a beige solid (95.4 mg, 68%). $^1$H NMR (MeOD) δ (ppm): 8.086 (s, 1H); 8.012 (d of t, 1H); 7.584 (m, 2H); 7.252 (m, 5H); 5.148 (s, 2H).

Examples 3b to 3f were prepared as described for example 3a.

b) 1-[2-(5-Chloro-2-fluoro-phenyl)-2H-tetrazol-5-yl]-2-phenyl-ethane-1,2-diol The title compound (used crude, yield determined after next step) was obtained from 2-(5-chloro-2-fluoro-phenyl)-5-styryl-2H-tetrazole (637 mg, 2.1 mmol) using citric acid (796 mg, 4.1 mmol), potassium osmate oxide hydrate (small scoop), 4-methyl morpholine N-oxide (275 mg, 2.3 mmol) in 1:1 mixture of t-butanol and water (20 mL). The crude product from extraction was not further purified.

c) 1-Phenyl-2-(2-m-tolyl-2H-tetrazol-5-yl)-ethane-1,2-diol

The title compound (2.26 g, used crude, yield determined after next step) was obtained from 5-styryl-2-m-tolyl-2H-tetrazole (1.44 g, 5.5 mmol) using citric acid (2.1 g, 10.9 mmol), potassium osmate oxide hydrate (small scoop), 4-methyl morpholine N-oxide (710 mg, 6.1 mmol) in 1:1 mixture of t-butanol and water (52 mL). The crude product from extraction was not further purified.

d) 1-[2-(3-Iodo-phenyl)-2H-tetrazol-5-yl]-2-phenyl-ethane-1,2-diol

The title compound is obtained from 2-(3-iodo-phenyl)-5-styryl-2H-tetrazole (1 mmol) using citric acid (2 mmol), potassium osmate oxide hydrate (small scoop), 4-methyl morpholine N-oxide (1.1 mmol) in 1:1 mixture of t-butanol and water (10 mL). The crude product from extraction is not further purified.

e) 3-[5-(1,2-Dihydroxy-2-phenyl-ethyl)-tetrazol-2-yl]-benzonitrile

The title compound is obtained from 3-(5-styryl-tetrazol-2-yl)-benzonitrile (1 mmol) using citric acid (2 mmol), potassium osmate oxide hydrate (small scoop), 4-methyl morpholine N-oxide (1.1 mmol) in 1:1 mixture of t-butanol and water (10 mL). The crude product from extraction is not further purified.

f) 1-[2-(2-Fluoro-5-methyl-phenyl)-2H-tetrazol-5-yl]-2-phenyl-ethane-1,2-diol The title compound is obtained from 2-(2-fluoro-5-methyl-phenyl)-5-styryl-2H-tetrazole (1 mmol) using citric acid (2 mmol), potassium osmate oxide hydrate (small scoop), 4-methyl morpholine N-oxide (1.1 mmol) in 1:1 mixture of t-butanol and water (10 mL). The crude product from extraction is not further purified.

EXAMPLE 4 a) 2-(3-Chloro-phenyl)-2H-tetrazole-5-carbaldehyde

1-[2-(3-chloro-phenyl)-2H-tetrazol-5-yl]-2-phenyl-ethane-1,2-diol (50.0 mg, 0.158 mmol) was weighed into a vial and toluene (3 ml) was added. Potassium carbonate (47.0 mg, 0.340 mmol) and lead (IV) acetate (70.0 mg, 0.158 mmol) were added with stirring. The reaction was allowed to stir for 2.5 hours. The reaction was filtered and ethyl acetate was added to the filtrate and an aqueous workup was done. The organic layer was washed with brine, dried over sodium sulfate, filtered and concentrated. The crude product was purified by column chromatography (40% EtOAc/Hexanes) to yield the pure product as a white solid (22.3 mg, 68%). $^1$H NMR (CDCl$_3$) δ (ppm): 10.34 (s, 1H); 8.27 (s, 1H); 8.14 (m, 1H); 7.575 (d, 2H).

Examples 4b to 4f were prepared as described for example 4a.

b) 2-(5-Chloro-2-fluoro-phenyl)-2H-tetrazole-5-carbaldehyde

The title compound (286 mg, 60% over 2 steps) was obtained 1-[2-(5-chloro-2-fluoro-phenyl)-2H-tetrazol-5-yl]-2-phenyl-ethane-1,2-diol (crude from 2.1 mmol reaction above) using potassium carbonate (1.0 g, 7 mmol) and lead (IV) acetate (980 mg, 2.2 mmol) in toluene (14 mL). The crude product was purified by column chromatography (10-20% EtOAc/hexanes).

c) 2-m-Tolyl-2H-tetrazole-5-carbaldehyde

The title compound (870 mg, 84% over 2 steps) was obtained from 1-phenyl-2-(2-m-tolyl-2H-tetrazol-5-yl)-ethane-1,2-diol (crude from 5.5 mmol reaction above) using potassium carbonate (2.02 g, 14.6 mmol) and lead (IV) acetate (2.52 g, 5.7 mmol) in toluene (35 mL) and dichloromethane (20 mL). The crude product was purified by column chromatography (10% EtOAc/hexanes). $^1$H NMR (CDCl$_3$) δ (ppm): 10.34 (s, 1H), 8.06 (s, 1H), 8.03 (d, 1H), 7.50 (t, 1H), 7.40 (d, 1H), 2.50 (s, 3H).

d) 2-(3-Iodo-phenyl)-2H-tetrazole-5-carbaldehyde

The title compound is obtained from 1-[2-(3-iodo-phenyl)-2H-tetrazol-5-yl]-2-phenyl-ethane-1,2-diol (1 mmol) using potassium carbonate (~3 mmol) and lead (IV) acetate (1.05 mmol) in toluene (7 mL).

e) 3-(5-Formyl-tetrazol-2-yl)-benzonitrile

The title compound is obtained from 3-[5-(1,2-dihydroxy-2-phenyl-ethyl)-tetrazol-2-yl]-benzonitrile (1 mmol) using potassium carbonate (~3 mmol) and lead (IV) acetate (1.05 mmol) in toluene (7 mL).

f) 2-(2-Fluoro-5-methyl-phenyl)-2H-tetrazole-5-carbaldehyde

The title compound is obtained from 1-[2-(2-fluoro-5-methyl-phenyl)-2H-tetrazol-5-yl]-2-phenyl-ethane-1,2-diol (1 mmol) using potassium carbonate (~3 mmol) and lead (IV) acetate (1.05 mmol) in toluene (7 mL).

EXAMPLE 5 a) [2-(3-Chloro-phenyl)-2H-tetrazol-5-yl]-methanol 2-(3-Chloro-phenyl)-2H-tetrazole-5-carbaldehyde (70.8 mg, 0.339 mmol) was dissolved in THF (5 mL) and lithium borohydride (25.9 mg, 1.187 mmol) was added. The reaction was allowed to reflux under argon for three hours and was then allowed to stir overnight at room temperature. The reaction was quenched with 1M hydrochloric acid and an aqueous workup was done extracting with ethyl acetate three times. The combined organic layers were washed with brine, dried over sodium sulfate, filtered and concentrated to yield the title compound as a white solid (75.8 mg, 106%). $^1$H NMR (CDCl$_3$) δ (ppm): 8.190 (s, 1H), 8.070 (m, 1H), 7.507 (m, 2H), 5.082 (s, 2H).

Examples 5b to 5f were prepared as described for example 5a.

b) [2-(5-Chloro-2-fluoro-phenyl)-2H-tetrazol-5-yl]-methanol

The title compound (59.8 mg, 75%) was obtained from 2-(5-chloro-2-fluoro-phenyl)-2H-tetrazole-5-carbaldehyde (78.9 mg, 0.35 mmol) using lithium borohydride (1.0 mL, 2 mmol) in THF (5 mL). The crude product was purified by column chromatography (25-30% EtOAc/hexanes). $^1$H NMR (CDCl$_3$) δ (ppm): 7.92 (dd, 1H), 7.52 (ddd, 1H), 7.33 (t, 1H), 5.11 (d, 2H), 2.41 (t, 1H).

c) (2-m-Tolyl-2H-tetrazol-5-yl)-methanol

The title compound (221 mg, 96%, beige solid) was obtained from 2-m-tolyl-2H-tetrazole-5-carbaldehyde (229 mg, 1.22 mmol) using lithium borohydride (3.5 mL, 7 mmol) in THF (10 mL). The crude product was purified by column chromatography (20-30% EtOAc/hexanes). $^1$H NMR (CDCl$_3$) δ (ppm): 7.97 (s, 1H), 7.94 (d, 1H), 7.46 (t, 1H), 7.33 (d, 1H), 5.08 (d, 2H), 2.50 (s, 3H), 2.40 (t, 1H).

d) [2-(3-Iodo-phenyl)-2H-tetrazol-5-yl]-methanol

The title compound is obtained from 2-(3-iodo-phenyl)-2H-tetrazole-5-carbaldehyde (1 mmol) using lithium borohydride (3-6 mmol) in THF (8-10 mL).

e) 3-(5-Hydroxymethyl-tetrazol-2-yl)-benzonitrile

The title compound is obtained from 3-(5-formyl-tetrazol-2-yl)-benzonitrile (1 mmol) using lithium borohydride (3-6 mmol) in THF (8-10 mL).

f) [2-(2-Fluoro-5-methyl-phenyl)-2H-tetrazol-5-yl]-methanol

The title compound is obtained from 2-(2-fluoro-5-methyl-phenyl)-2H-tetrazole-5-carbaldehyde (1 mmol) using lithium borohydride (3-6 mmol) in THF (8-10 mL).

EXAMPLE 6 a) 1-[2-(3-chloro-phenyl)-2H-tetrazol-5-yl-ethanol 2-(3-Chloro-phenyl)-2H-tetrazole-5-carbaldehyde (75.6 mg, 0.362 mmol) was dissolved in THF (2 mL) under argon and the flask was immersed in ice. Methyl magnesium bromide (1M solution/butyl ether 0.51 mL, 0.507 mmol) was added dropwise while the reaction was cooled in ice. After fifteen minutes at 0° C., the ice bath was removed and the reaction was allowed to stir at room temperature for two hours. 1M Hydrochloric acid was added to quench the reaction and an aqueous workup was done extracting with ethyl acetate three times. The combined organic layers were washed with brine, dried over sodium sulfate, filtered and concentrated. The crude product was purified by column chromatography (3% MeOH/CH$_2$Cl$_2$) to yield the title compound as a clear oil (62.4 mg, 77%). $^1$H NMR (CDCl$_3$) δ (ppm): 8.18 (s, 1H), 8.06 (m, 1H), 7.50 (m, 2H), 5.32 (m, 1H), 2.69 (d, 1H), 1.76 (d, 3H).

Examples 6b to 6f were prepared as described for example 6a.

b) 1-[2-(5-Chloro-2-fluoro-phenyl)-2H-tetrazol-5-yl]-ethanol

The title compound (143.7 mg, 77%, estimated ~90% pure as carried to next steps) was obtained from 2-(5-chloro-2-fluoro-phenyl)-2H-tetrazole-5-carbaldehyde (174 mg, 0.77 mmol) using methyl magnesium bromide (2.0 mL, 2 mmol) in THF (5 mL). The crude product was purified by column chromatography (25-30% EtOAc/hexanes). $^1$H NMR (CDCl$_3$) δ (ppm): 7.90 (dd, 1H), 7.51 (ddd, 1H), 7.33 (t, 1H), 5.34 (q, 1H), 1.87 (t, 1H), 1.77 (d, 3H).

c) 1-(2-m-Tolyl-2H-tetrazol-5-yl)-ethanol

The title compound (221 mg, 96%, beige solid) was obtained from 2-m-tolyl-2H-tetrazole-5-carbaldehyde (229 mg, 1.22 mmol) using methyl magnesium bromide (3.5 mL, 7 mmol) in THF (10 mL). The crude product was purified by column chromatography (20-30% EtOAc/hexanes). $^1$H NMR (CDCl$_3$) δ (ppm): 7.94 (s, 1H), 7.92 (d, 1H), 7.43 (t, 1H), 7.31 (d, 1H), 5.31 (m, 1H), 2.48 (s, 3H), 1.77 (d, 3H).

d) 1-[2-(3-Iodo-phenyl)-2H-tetrazol-5-yl]-ethanol

The title compound is obtained from 2-(3-iodo-phenyl)-2H-tetrazole-5-carbaldehyde (1 mmol) using methyl magnesium bromide (1.4 mmol) in THF (5 mL).

e) 3-[5-(1-Hydroxy-ethyl)-tetrazol-2-yl]-benzonitrile

The title compound is obtained from 3-(5-formyl-tetrazol-2-yl)-benzonitrile (1 mmol) using methyl magnesium bromide (1 mmol) in THF (5 mL).

f) 1-[2-(2-Fluoro-5-methyl-phenyl)-2H-tetrazol-5-yl]-ethanol

The title compound is obtained from 2-(2-fluoro-5-methyl-phenyl)-2H-tetrazole-5-carbaldehyde (1 mmol) using methyl magnesium bromide (1.4 mmol) in THF (5 mL).

EXAMPLE 7 a) 5-Bromomethyl-2-(3-chloro-phenyl)-2H-tetrazole

Dichloromethane (5 mL) was added to 2-(3-chloro-phenyl)-2H-tetrazol-5-yl]-methanol (49.5 mg, 0.235 mmol) followed by triphenylphosphine (92.6 mg, 0.353 mmol). The reaction was immersed in a −40° C. bath and NBS (62.8 mg, 0.353 mmol) was added in dichloromethane (2 mL). The reaction was allowed to stir under Argon for two hours. Saturated sodium bicarbonate was added and the cold bath was removed. An aqueous workup was done extracting the product with dichloromethane three times. The combined organic layers were washed with brine, dried over sodium sulfate, filtered and concentrated. The crude product was purified by column chromatography (2% MeOH/CH$_2$Cl$_2$) to yield the title compound as a white solid (45.9 mg, 71%). $^1$H NMR (CDCl$_3$) δ (ppm): 8.179 (s, 1H), 8.050 (m, 1H), 7.518 (m, 2H), 4.730 (s, 2H).

b) 5-(1-Bromo-ethyl)-2-(3-chloro-phenyl)-2H-tetrazole

The title compound is prepared according to the procedure for 5-bromomethyl-2-(3-chloro-phenyl)-2H-tetrazole (example 7a) using 1-[2-(3-chloro-phenyl)-2H-tetrazol-5-yl-ethanol as starting material.

EXAMPLE 8 a) Methanesulfonic acid 1-[2-(3-chlorophenyl)-2H-tetrazol-5-yl]-ethyl ester

1-[2-(3-chloro-phenyl)-2H-tetrazol-5-yl-ethanol (55.3 mg, 0.246 mmol) was dissolved in dichloromethane under Argon and triethylamine (41.1 uL, 0.295 mmol) was added followed by methyl sulfonyl chloride (22.8 uL, 0.295 mmol). The reaction was allowed to stir at room temperature overnight.

Sodium bicarbonate (sat.) was added and an aqueous workup was done extracting with ethyl acetate three times. The combined organic layers were washed with brine, dried over sodium sulfate, filtered and concentrated. The crude product was purified by an SPE tube (5% MeOH/$CH_2Cl_2$) to yield the title compound as a yellow oil (27.7 mg, 37%). $^1$H NMR ($CDCl_3$) δ (ppm): 8.18 (s, 1H), 8.07 (m, 1H), 7.533 (m, 2H), 6.15 (q, 1H), 3.157 (s, 3H), 1.99 (d, 3H).

Examples 8b to 8k were prepared as described for example 8a.

b) Methanesulfonic acid 2-(5-chloro-2-fluoro-phenyl)-2H-tetrazol-5-ylmethyl ester The title compound was obtained from [2-(5-chloro-2-fluoro-phenyl)-2H-tetrazol-5-yl]-methanol (39 mg, 0.17 mmol) using methane sulfonyl chloride (0.02 mL, 0.26 mmol) and triethyl amine (0.05 mL, 0.36 mmol) in dichloromethane (5 mL). The crude extraction product was divided into two samples and carried forward to the next reaction without further purification.

c) Methanesulfonic acid 1-[2-(5-chloro-2-fluoro-phenyl)-2H-tetrazol-5-yl]-ethyl ester The title compound was obtained from 1-[2-(5-chloro-2-fluoro-phenyl)-2H-tetrazol-5-yl]-ethanol (103 mg, 65% pure, 0.28 mmol) using methane sulfonyl chloride (0.05 mL, 0.65 mmol) and triethyl amine (0.15 mL, 1.1 mmol) in dichloromethane (5 mL). The crude extraction product was divided into three samples and carried forward to the next reaction without further purification.

d) Methanesulfonic acid 2-m-tolyl-2H-tetrazol-5-ylmethyl ester

The title compound is obtained from (2-m-tolyl-2H-tetrazol-5-yl)-methanol (1 mmol) using methane sulfonyl chloride (1.5 mmol) and triethyl amine (2 mmol) in dichloromethane (15 mL).

e) Methanesulfonic acid 1-(2-m-tolyl-2H-tetrazol-5-yl)-ethyl ester

The title compound was obtained from 1-(2-m-tolyl-2H-tetrazol-5-yl)-ethanol (1 mmol) using methane sulfonyl chloride (1.5 mmol) and triethyl amine (2 mmol) in dichloromethane (15 mL).

f) Methanesulfonic acid 2-(3-cyano-phenyl)-2H-tetrazol-5-ylmethyl ester

The title compound is obtained from 3-(5-hydroxymethyl-tetrazol-2-yl)-benzonitrile (1 mmol) using methane sulfonyl chloride (1.5 mmol) and triethyl amine (2 mmol) in dichloromethane (5 mL).

g) Methanesulfonic acid 1-[2-(3-cyano-phenyl)-2H-tetrazol-5-yl]-ethyl ester

The title compound is obtained from 3-[5-(1-hydroxy-ethyl)-tetrazol-2-yl]-benzonitrile (1 mmol) using methane sulfonyl chloride (1.5 mmol) and triethyl amine (2 mmol) in dichloromethane (15 mL).

h) Methanesulfonic acid 2-(2-fluoro-5-methyl-phenyl)-2H-tetrazol-5-ylmethyl ester The title compound is obtained from [2-(2-fluoro-5-methyl-phenyl)-2H-tetrazol-5-yl]-methanol (1 mmol) using methane sulfonyl chloride (1.5 mmol) and triethyl amine (2 mmol) in dichloromethane (5 mL).

i) Methanesulfonic acid 1-[2-(2-fluoro-5-methyl-phenyl)-2H-tetrazol-5-yl]-ethyl ester The title compound is obtained from 1-[2-(2-fluoro-5-methyl-phenyl)-2H-tetrazol-5-yl]-ethanol (1 mmol) using methane sulfonyl chloride (1.5 mmol) and triethyl amine (2 mmol) in dichloromethane (5 mL).

j) Methanesulfonic acid 2-(3-iodo-phenyl)-2H-tetrazol-5-ylmethyl ester

The title compound is obtained from [2-(3-iodo-phenyl)-2H-tetrazol-5-yl]-methanol (1 mmol) using methane sulfonyl chloride (1.5 mmol) and triethyl amine (2 mmol) in dichloromethane (15 mL).

k) Methanesulfonic acid 1-[2-(3-iodo-phenyl)-2H-tetrazol-5-yl]-ethyl ester

The title compound was obtained from 1-[2-(3-iodo-phenyl)-2H-tetrazol-5-yl]-ethanol (1 mmol) using methane sulfonyl chloride (1.5 mmol) and triethyl amine (2 mmol) in dichloromethane (15 mL).

EXAMPLE 9 a) 4-Methyl-5-pyridin-4-yl-2,4-dihydro-[1,2,4]triazole-3-thione

Isonicotinoyl chloride hydrochloride (27.5 g, 154.5 mmol) and 4-methyl-3-thiosemicarbazide (16.4 g, 155.9 mmol) were mixed in pyridine (200 ml) and stirred under argon at ambient temperature overnight. After evaporation to dryness, aqueous sodium hydroxide (250 mL, 2M, 500 mmol) was added and the resulting solution was heated at 60° C. for 16 h. After cooling to room temperature, the solution was neutralized with 6N hydrochloric acid. The precipitate that formed was collected by filtration to give the title compound (pale yellow solid, 16.4 g, 55%). $^1$H NMR (DMSO-d6), δ (ppm): 8.78 (dd, 2H), 7.75 (dd, 2H), 3.59 (s, 3H).

EXAMPLE 10

Made in an analogous manner to above:

a) 4-Ethyl-5-pyridin-4-yl-2,4-dihydro-[1,2,4]triazole-3-thione

The title compound (pale yellow solid, 16.7 g, 58%) was prepared from isonicotinoyl chloride hydrochloride (25.1 g, 140.8 mmol) and 4-ethyl-3-thiosemicarbazide (16.87 g, 141.5 mmol) in pyridine (185 ml) with sodium hydroxide (220 mL, 2M, 440 mmol) added to the intermediate formed to effect cyclization. $^1$H NMR (DMSO-d6) δ (ppm): 8.80 (dd, 2H), 7.72 (dd, 2H), 4.11 (q, 2H), 3.59 (t, 3H).

EXAMPLE 11

4-Cyclopropyl-5-pyridin-4-yl-2,4-dihydro-[1,2,4]triazole-3-thione

A solution of isonicotinoyl hydrazide (2.62 g, 19.1 mmol) and cyclopropyl isothiocyanate (1.55 mL, 16.7 mmol) in methanol (15 mL) was heated at 60° C. for 1 h. The mixture was cooled to room temperature and the solvent was removed. Aqueous sodium hydroxide (9 mL, 2M, 18 mmol) was added and the resulting solution was heated at 60° C. for 20 h. After cooling to room temperature, the solution was neutralized with 3N hydrochloric acid. The precipitate that formed was collected by filtration to give the title compound (pale yellow solid, 3.58 g, 98%). $^1$H NMR (DMSO-d6) δ (ppm): 8.76 (dd, 2H), 7.80 (dd, 2H), 1.00 (m, 2H), 0.61 (m, 2H) (note one cyclopropyl-N signal blocked solvent signal at 3.32 ppm).

EXAMPLE 12

4-(4-Methyl-5-methylsulfanyl-4H-[1,2,4]triazol-3-yl)-pyridine

To a solution of 4-Methyl-5-pyridin-4-yl-2,4-dihydro-[1,2,4]triazole-3-thione (1000 mg, 5.20 mmol) in 1M sodium hydroxide (10 mL), added a solution of iodomethane (0.52 mL, 8.32 mmol) in ethanol (3 mL). Stirred at RT overnight. Extracted into 200 mL dichloromethane and washed with brine (50 mL). Dried over anhydrous sodium sulfate, filtered and concentrated in vacuo to yield title compound (1.00 g, 94% yield). $^1$H-NMR (CDCl$_3$) δ (ppm): 8.81 (d, 2H), 7.62 (d, 2H), 3.68 (s, 3H), 2.82 (s, 3H).

EXAMPLE 13

4-(4-Cyclopropyl-5-methylsulfanyl-4H-[1,2,4]triazol-3-yl)-pyridine

A solution of iodomethane (0.457 mL, 7.33 mmol) in ethanol (3 mL) was added to a solution of 4-cyclopropyl-5-pyridin-4-yl-4H-[1,2,4]triazole-3-thiol (1 g, 4.58 mmol) in 1M sodium hydroxide (10 mL) at room temperature. After stirring overnight, the reaction mixture was extracted with dichloromethane and then the organic layer was washed with brine, dried over anhydrous sodium sulfate, filtered and concentrated to afford the titled compound (729.1 mg, 69%, beige solid). $^1$H NMR (CDCl$_3$) δ (ppm): 8.77 (d, 2H), 7.75 (m 2H), 3.23 (m, 1H), 2.82 (s, 3H), 1.17 (m, 2H), 0.80 (m, 2H).

EXAMPLE 14 a) 4-(5-Methanesulfonyl-4-methyl-4H-[1,2,4]triazol-3-yl)-pyridine

To a solution of 4-(4-Methyl-5-methylsulfanyl-4H-[1,2,4]triazol-3-yl)-pyridine (1000 mg, 4.85 mmol) in acetic acid, added a solution of KMnO$_4$ (1.15 g, 7.28 mmol) in H$_2$O (50 mL) drop-wise. Stirred at RT for 3 hours. Added sodium hydrogen sulfite until purple colour was discharged. Extracted into chloroform (3×100 mL). Washed organic layer with saturated sodium bicarbonate (50 mL). Dried over anhydrous sodium sulfate, filtered and concentrated in vacuo to yield title compound (1.01 g, 87% yield). $^1$H-NMR (CDCl$_3$) δ (ppm): 8.89 (d, 2H), 7.64 (d, 2H), 4.05 (s, 3H), 3.64 (s, 3H).

b) 3-(5-Methanesulfonyl-4-methyl-4H-[1,2,4]triazol-3-yl)-pyridine

The title compound was prepared analogously to the sequence described in example 9, 12, and 14 using nicotinoyl chloride hydrochloride as starting material. $^1$H NMR (CDCl$_3$) δ (ppm): 3.59 (s, 3H) 3.99 (s, 3H) 7.52 (m, 1H) 8.02 (dt, 1H) 8.83 (dd, 1H) 8.91 (m, 1H).

c) 3-(3,5-Difluoro-phenyl)-5-methanesulfonyl-4-methyl-4H-[1,2,4]triazole

The title compound was prepared analogously to the sequence described in example 9, 12, and 14 using 3,5-difluoro-benzoyl chloride as starting material. 1H NMR (DMSO-D6) δ (ppm): 3.60 (s, 3H) 3.89 (s, 3H) 7.56 (s, 3H).

EXAMPLE 15

4-(4-Cyclopropyl-5-methanesulfonyl-4H-[1,2,4]triazol-3-yl)-pyridine

A solution of potassium permanganate (525 mg, 3.3 mmol) in water (22.0 mL) was added to a solution of 4-(4-cyclopropyl-5-methylsulfanyl-4H-[1,2,4]triazol-3-yl)-pyridine (514 mg, 2.2 mmol) in acetic acid (11 mL) drop-wise at room temperature. After stirring for 3 hours, sodium hydrogen sulfite was added until the purple color was discharged. The reaction mixture was extracted with chloroform and then the organic layer was washed with saturated sodium bicarbonate, dried over anhydrous sodium sulfate, filtered and concentrated to afford the titled compound (546.7 mg, 94%, white solid). $^1$H NMR (CDCl$_3$) δ (ppm): 8.86 (d, 2H), 7.77 (d, 2H), 3.64 (m, 1H), 3.63 (s, 3H), 1.25 (m, 2H), 1.01 (m, 2H).

EXAMPLE 16 a) Methyl-(4-methyl-5-pyridin-4-yl-4H-[1,2,4]triazol-3-yl)-amine

A mixture of 1000 mg (4.35 mmol) N-amino-N',N"-dimethyl-guanidine hydriodide (Henry; Smith; J. Amer. Chem. Soc.; 73; 1951; 1858) and 774 mg (4.35 mmol) isonicotinoyl chloride hydrochloride in 3 ml of pyridine was heated with microwaves for 5 min at 160° C. K$_2$CO$_3$(sat) was added and the mixture was extracted 4 times with CHCl$_3$. The organic phase was dried and concentrated. Recrystallization from ethanol, water and EtOAc gave 216 mg (26%) of a yellow white solid. 1H NMR (DMSO), d (ppm): 2.85 (d, 3H) 3.45 (s, 3H) 6.25 (d, 1H) 7.65 (m, 2H) 8.67 (m, 2H).

b) [5-(3,5-Difluoro-phenyl)-4-methyl-4H-[1,2,4]triazol-3-yl]-methyl-amine

The title compound was prepared according to the procedure for methyl-(4-methyl-5-pyridin-4-yl-4H-[1,2,4]triazol-3-yl)-amine (example 16a) from 3,5-difluoro-benzoyl chloride. 1H NMR (DMSO-D6) d (ppm): 2.83 (d, 3H) 3.41 (s, 3H) 6.20 (d, 1H) 7.35 (m, 3H), c) Methyl-(4-methyl-5-pyridin-3-yl-4H-[1,2,4]triazol-3-yl)-amine The title compound is prepared according to the procedure for methyl-(4-methyl-5-pyridin-4-yl-4H-[1,2,4]triazol-3-yl)-amine (example 16a) from nicotinoyl chloride hydrochloride.

EXAMPLE 17 a) 3-Pyridin-4-yl-5,6,7,8-tetrahydro-[1,2,4]triazolo [4,3-a]pyrimidine

A solution of 750 mg (3.1 mmol) (1,4,5,6-tetrahydro-pyrimidin-2-yl)-hydrazine hydroiodide (ref. Krezel, Izabella; Pharmazie; EN; 49; 1; 1994; 27-31) and 552 mg (3.1 mmol) isonicotinoyl chloride hydrochloride in 3 ml pyridine was heated at 120° C. over night. The reaction mixture was cooled and diluted with $K_2CO_3$ (sat) and extracted with 3×10 ml chloroform. The combined organic extracts were dried and concentrated. Flash chromatography ($CH_2Cl_2$/MeOH 10:1) afforded 83 mg (18%) of a white solid. 1H NMR ($CDCl_3$) d (ppm): 1.91 (m, 2H) 3.24 (m, 2H) 4.13 (m, 2H) 7.67 (m, 2H) 8.65 (m, 2H).

b) 3-Pyridin-3-yl-5,6,7,8-tetrahydro-[1,2,4]triazolo [4,3-a]pyrimidine

The title compound is prepared according to the procedure for 3-pyridin-4-yl-5,6,7,8-tetrahydro-[1,2,4]triazolo[4,3-a] pyrimidine (example 17a) from nicotinoyl chloride hydrochloride.

c) 3-(3,5-Difluoro-phenyl)-5,6,7,8-tetrahydro-[1,2,4] triazolo[4,3-a]pyrimidine The title compound is prepared according to the procedure for 3-pyridin-4-yl-5,6,7,8-tetrahydro-[1,2,4]triazolo[4,3-a] pyrimidine (example 17a) from 3,5-difluoro-benzoyl chloride.

EXAMPLE 18

2-(methylthio)-4,5,6,7-tetrahydro-1H-1,3-diazepine

Methyl iodide (0.55 ml, 1.15 mmol) was added to a solution of 1,3-diazepane-2-thione (1.00 g, 7.68 mmol) in acetone (8 ml). The reaction mixture was refluxed for 15 min. EtOH was added to the hot solution to dissolve the solids. After cooling to r.t. hex. was added and the precipitate was collected by filtration, washed with hex. and dried to give 1.79 g (86%) crude title compound which was used directly in the next step.

EXAMPLE 19

1,3-diazepan-2-one hydrazone hydroiodide

Hydrazine hydrate (0.44 ml, 7.23 mmol) was added to a solution of 2-(methylthio)-4,5,6,7-tetrahydro-1H-1,3-diazepine hydroiodide (1.79 d, 6.58 mmol) in EtOH (12 ml). The reaction mixture was refluxed for 5 h and cooled to r.t. $Et_2O$ was added and the product was collected by filtration, washed with $Et_2O$ and dried under vacuum to give 1.46 g (100%) crude title compound which was used directly in the next step.

EXAMPLE 20 a) 3-pyridin-4-yl-6,7,8,9-tetrahydro-5H-[1,2,4]triazolo[4,3-α][1,3]diazepine A mixture of 1,3-diazepan-2-one hydrazone hydroiodide (1.00 g, 3.9 mmol) and isonicotinoyl chloride hydrochloride (695 mg, 3.9 mmol) was heated in a microwave reactor at 160° C. for 10 min. The reaction mixture was poured into $Na_aCO_3$ solution, sat., and extracted with DCM. The organic phase was dried and concentrated. Flash chromatography (DCM/MeOH 20:1) gave 1.74 g crude title compound which was used directly in the next step. $^1$H NMR: 1.89 (s, 4H) 3.15 (m, 2H) 3.86 (m, 2H) 7.44 (d, 2H) 8.66 (d, 2H).

b) 3-Pyridin-3-yl-5,6,7,8-tetrahydro-4H-1,2,3a,8-tetraaza-azulene

The title compound is obtained from nicotinoyl chloride hydrochloride according to the procedure described for 3-pyridin-4-yl-6,7,8,9-tetrahydro-5H-[1,2,4]triazolo[4,3-a][1,3] diazepine (example 20a).

c) 3-(3,5-Difluoro-phenyl)-5,6,7,8-tetrahydro-4H-1, 2,3a,8-tetraaza-azulene

The title compound is obtained from 3,5-difluoro-benzoyl chloride according to the procedure described for 3-pyridin-4-yl-6,7,8,9-tetrahydro-5H-[1,2,4]triazolo[4,3-a][1,3]diazepine (example 20a).

EXAMPLE 21

4-(4-Ethyl-4H-[1,2,4]triazol-3-yl)-pyridine

4-Ethyl-5-pyridin-4-yl-2,4-dihydro-[1,2,4]triazole-3-thione (4.2 g, 20.4 mmol) was slowly added to Raney nickel (~40 g, washed three times with 25 mL portions of ethanol) in ethanol (50 mL). The resulting mixture was stirred at 65° C. for approximately 28 hours. The solution mixture was carefully filtered and concentrated in vacuo to yield the title compound (2.88 g, 81.3%). $^1$H NMR ($CDCl_3$) δ (ppm): 8.81 (d, 2H), 8.33 (s, 1H), 7.62 (d, 2H), 8.18 (q, 2H), 1.51 (t, 3H).

EXAMPLE 22

(4-Ethyl-5-pyridin-4-yl-4H-[1,2,4]triazol-3-yl)-methanol

A solution of 4-(4-ethyl-4H-[1,2,4]triazol-3-yl)-pyridine (2.55 g, 14.6 mmol) in 37% formaldehyde (~12 mL) was stirred at 37° C. for 16 hours. Flash chromatography (10% methanolic ammonia in dichloromethane) yielded title product (2.55 g, 85%, used without further purification to remove remaining para-formaldehyde). $^1$H NMR ($CDCl_3$) δ (ppm): 8.81 (d, 2H), 7.72 (d, 2H), 5.74 (t, 1H), 4.73 (d, 2H), 4.26 (q, 2H), 1.27 (t, 3H).

EXAMPLE 23 a) 4-Ethyl-5-pyridin-4-yl-4H-[1,2,4]triazole-3-carbaldehyde

Dichloromethane (4 mL) was added to a vial containing (4-ethyl-5-pyridin-4-yl-4H-[1,2,4]triazol-3-yl)-methanol (56.7 mg, 0.279 mmol) and manganese dioxide (364.3 mg, 4.19 mmol) was added. The vial was sealed and the reaction was allowed to stir for two hours. The reaction was filtered through celite and concentrated to yield the title compound. $^1$H NMR ($CDCl_3$) δ (ppm): 10.21 (s, 1H), 8.88 (d, 2H), 7.63 (d, 2H), 4.45 (q, 2H), 1.48 (t, 3H).

b) 4-Methyl-5-pyridin-3-yl-4H-[1,2,4]triazole-3-carbaldehyde

The title compound is prepared analogously to the sequence described for 4-(4-ethyl-4H-[1,2,4]triazol-3-yl)- pyridine (example 21), (4-ethyl-5-pyridin-4-yl-4H-[1,2,4]triazol-3-yl)-methanol (example 22), and 4-ethyl-5-pyridin-4-yl-4H-[1,2,4]triazole-3-carbaldehyde (example 23a) by using 4-methyl-5-pyridin-3-yl-2,4-dihydro-[1,2,4]triazole-3-thione as starting material.

c) 5-(3,5-Difluoro-phenyl)-4-methyl-4H-[1,2,4]triazole-3-carbaldehyde

The title compound is prepared analogously to the sequence described for 4-(4-ethyl-4H-[1,2,4]triazol-3-yl)-pyridine (example 21), (4-ethyl-5-pyridin-4-yl-4H-[1,2,4]triazol-3-yl)-methanol (example 22), and 4-ethyl-5-pyridin-4-yl-4H-[1,2,4]triazole-3-carbaldehyde (example 23a) by using 5-(3,5-Difluoro-phenyl)-4-methyl-2,4-dihydro-[1,2,4]triazole-3-thione as starting material.

EXAMPLE 24 a) Ethyl 4-{[2-(3-chlorophenyl)-2H-tetrazol-5-yl]methyl}piperazine-1-carboxylate 2-(3-Chloro-phenyl)-2H-tetrazole-5-carbaldehyde (22.3 mg, 0.107 mmol) was dissolved in 1,2-dichloroethane under argon and ethyl-1-piperazine carboxylate (16.4 uL, 0.112 mmol) was added followed by sodium triacetoxy borohydride (31.8 mg, 0.150 mmol). The reaction was allowed to stir overnight. Ethyl acetate was added and the solution was washed with sodium bicarbonate (sat.), brine, dried over sodium sulfate, filtered and concentrated. The crude product was purified by column chromatography using 45% EtOAc/Hexanes and 100% EtOAc to yield the title compound as a white solid (17.4 mg, 46%). $^1$H NMR (CDCl$_3$) δ (ppm): 8.190 (s, 1H); 8.070 (m, 1H); 7.469 (m, 2H); 4.139 (q, 2H); 3.983 (s, 2H); 3.541 (m, 4H); 2.604 (m, 4H); 1.263 (t, 3H).

Examples 24b to 24f were prepared as described for example 24a.

b) 4-[2-(5-Chloro-2-fluoro-phenyl)-2H-tetrazol-5-ylmethyl]-piperazine-1-carboxylic acid ethyl ester The title compound (28 mg, 79%, yellow oil) was obtained from 2-(5-chloro-2-fluoro-phenyl)-2H-tetrazole-5-carbaldehyde (21.8 mg, 0.1 mmol) using ethyl-1-piperazine carboxylate (0.03 uL, 0.2 mmol) and sodium triacetoxy borohydride (50 mg, 0.24 mmol) in 1,2-dichloroethane (1.3 mL). The crude product was purified by column chromatography (35-40% EtOAc/hexanes). $^1$H NMR (CDCl$_3$) δ (ppm): 7.93 (dd, 1H), 7.51 (ddd, 1H), 7.34 (t, 1H), 4.14 (q, 2H), 4.02 (s, 2H), 3.55 (m, 4H), 2.61 (m, 4H), 1.27 (t, 3H).

c) 4-(2-m-Tolyl-2H-tetrazol-5-ylmethyl)-piperazine-1-carboxylic acid ethyl ester The title compound (36 mg, 57%, yellow oil) was obtained from 2-m-tolyl-2H-tetrazole-5-carbaldehyde (36.1 mg, 0.19 mmol) using ethyl-1-piperazine carboxylate (0.04 uL, 0.27 mmol) and sodium triacetoxy borohydride (75 mg, 0.35 mmol) in 1,2-dichloroethane (2.5 mL). The crude product was purified by column chromatography (20-35% EtOAc/hexanes). $^1$H NMR (CDCl$_3$) δ (ppm): 7.97 (s, 1H), 7.94 (d, 1H), 7.45 (t, 1H), 7.32 (d, 1H), 4.14 (q, 2H), 4.00 (s, 2H), 3.55 (m, 4H), 2.61 (m, 4H), 2.49 (s, 3H), 1.27 (t, 3H).

d) 4-[2-(3-Iodo-phenyl)-2H-tetrazol-5-ylmethyl]-piperazine-1-carboxylic acid ethyl ester The title compound is obtained from 2-(3-iodo-phenyl)-2H-tetrazole-5-carbaldehyde (1 mmol) using ethyl-1-piperazine carboxylate (1.1-2 mmol) and sodium triacetoxy borohydride (1.5-2 mmol) in 1,2-dichloroethane (10-15 mL).

e) 4-[2-(3-Cyano-phenyl)-2H-tetrazol-5-ylmethyl]-piperazine-1-carboxylic acid ethyl ester The title compound is obtained from 3-(5-formyl-tetrazol-2-yl)-benzonitrile (1 mmol) using ethyl-1-piperazine carboxylate (1.1-2 mmol) and sodium triacetoxy borohydride (1.5-2 mmol) in 1,2-dichloroethane (10-15 mL).

f) 4-[2-(2-Fluoro-5-methyl-phenyl)-2H-tetrazol-5-ylmethyl]-piperazine-1-carboxylic acid ethyl ester The title compound is obtained from 2-(2-fluoro-5-methyl-phenyl)-2H-tetrazole-5-carbaldehyde (1 mmol) using ethyl-1-piperazine carboxylate (1.1-2 mmol) and sodium triacetoxy borohydride (1.5-2 mmol) in 1,2-dichloroethane (10-15 mL).

EXAMPLE 25 a) 4-[5-({[2-(3-chlorophenyl)-2H-tetrazol-5-yl]methyl}thio)-4-cyclopropyl-4H-1,2,4-triazol-3-yl]pyridine 5-Bromomethyl-2-(3-chloro-phenyl)-2H-tetrazole (18.7 mg, 0.068 mmol) was weighed into a vial and potassium carbonate (10.4 mg, 0.075 mmol) 4-cyclopropyl-5-pyridin-4-yl-2,4-dihydro-[1,2,4]triazole-3-thione (14.8 mg, 0.068 mmol) and acetonitrile (3 mL) were added. The vial was sealed and the reaction was allowed to stir at room temperature overnight. The reaction mixture was put through an SPE tube (10% methanol in dichloromethane) to yield the title compound as a white solid (18.3 mg, 66%). $^1$H NMR δ (ppm): 8.78 (d, 2H), 8.16 (s, 1H), 8.04 (m, 1H), 7.76 (d, 2H), 7.49 (m, 2H), 4.97 (s, 2H), 3.29 (m, 1H), 1.19 (m, 2H), 0.84 (m, 2H).

Examples 25b to 25y may be prepared as described for example 25a.

b) 4-[5-({1-[2-(3-chlorophenyl)-2H-tetrazol-5-yl]ethyl}thio)-4-cyclopropyl-4H-1,2,4-triazol-3-yl]pyridine The title compound (25.2 mg, 68%, white solid) was prepared from methanesulfonic acid 1-[2-(3-chlorophenyl)-2H-tetrazol-5-yl]-ethyl ester (26.4 mg, 0.087 mmol) using potassium carbonate (13.3 mg, 0.096 mmol) and 4-cyclopropyl-5-pyridin-4-yl-2,4-dihydro-[1,2,4]triazole-3-thione (19.0 mg, 0.087 mmol) in acetonitrile (3 mL) at room temperature overnight. The reaction mixture was purified by chromatography using a silica SPE tube (2% methanol in dichloromethane). $^1$H NMR (CDCl$_3$) δ (ppm): 8.78 (d, 2H), 8.16 (s, 1H), 8.04 (m, 1H), 7.75 (d, 2H), 7.49 (m, 2H), 5.67 (q, 1H), 3.24 (m, 1H), 2.08 (d, 3H), 1.16 (m, 2H), 0.82 (m, 2H).

c) Ethyl 4-{1-[2-(3-chlorophenyl)-2H-tetrazol-5-yl]ethyl}piperazine-1-carboxylate The title compound (12.3 mg, 37%, yellow oil) was prepared from methyl sulfonic acid 1-[2-(3-chlorophenyl)-2H-tetrazol-5-yl]-ethyl ester (27.7 mg, 0.091 mmol) using potassium carbonate (13.8 mg, 0.100 mmol) and 1-ethoxycarbonyl piperazine (13.3 uL, 0.091 mmol) in acetonitrile (4 mL) at 80° C. overnight. The product was purified was by chromatography using a silica SPE tube (10% MeOH/CH$_2$Cl$_2$) followed by a second chromatography using a silica SPE tube (5%

MeOH/CH$_2$Cl$_2$). $^1$H NMR (CDCl$_3$) δ (ppm): 8.17 (s, 1H), 8.07 (dt, 1H), 7.50 (m, 2H), 4.29 (q, 1H), 4.10 (q, 2H), 3.52 (m, 4H), 2.56 (m, 4H), 1.64 (d, 3H), 1.24 (t, 3H).

d) 4-{5-[2-(5-Chloro-2-fluoro-phenyl)-2H-tetrazol-5-ylmethylsulfanyl]-4-methyl-4H-[1,2,4]triazol-3-yl}-pyridine The title compound (32.1 mg, 94%, white solid) was obtained from methanesulfonic acid 2-(5-chloro-2-fluoro-phenyl)-2H-tetrazol-5-ylmethyl ester (~26 mg, 0.085 mmol) using potassium carbonate (38 mg, 0.27 mmol) and 4-methyl-5-pyridin-4-yl-2,4-dihydro-[1,2,4]triazole-3-thione (20 mg, 0.10 mmol) in acetonitrile (1.5 mL) at room temperature overnight. The reaction mixture was purified by chromatography using a silica SPE tube (2-3% methanol in dichloromethane). $^1$H NMR (CDCl$_3$) δ (ppm): 8.80 (br.s, 2H), 7.87 (dd, 1H), 7.62 (d, 2H), 7.49 (m, 1H), 7.31 (t, 1H), 4.84 (s, 2H), 3.71 (s, 3H).

e) 4-{5-[2-(5-Chloro-2-fluoro-phenyl)-2H-tetrazol-5-ylmethylsulfanyl]-4-cyclopropyl-4H-[1,2,4]triazol-3-yl}-pyridine The title compound (30.7 mg, 84%, white filmy solid) was obtained from methanesulfonic acid 2-(5-chloro-2-fluoro-phenyl)-2H-tetrazol-5-ylmethyl ester (~26 mg, 0.085 mmol) using potassium carbonate (38 mg, 0.27 mmol) and 4-cyclopropyl-5-pyridin-4-yl-2,4-dihydro-[1,2,4]triazole-3-thione (22 mg, 0.10 mmol) in acetonitrile (1.5 mL) at room temperature overnight. The reaction mixture was purified by chromatography using a silica SPE tube (2-3% methanol in dichloromethane). $^1$H NMR (CDCl$_3$) δ (ppm): 8.76 (br.s, 2H), 7.88 (dd, 1H), 7.75 (d, 2H), 7.49 (m, 1H), 7.32 (dd, 1H), 4.96 (s, 2H), 3.30 (septet, 1H), 1.18 (m, 2H), 0.83 (m, 2H).

f) 4-(5-{1-[2-(5-Chloro-2-fluoro-phenyl)-2H-tetrazol-5-yl]-ethylsulfanyl}-4-methyl-4H-[1,2,4]triazol-3-yl)-pyridine The title compound (12.3 mg, 32%, white foam) was obtained from methanesulfonic acid 1-[2-(5-chloro-2-fluoro-phenyl)-2H-tetrazol-5-yl]-ethyl ester (~29.5 mg, 0.09 mmol) using potassium carbonate (38 mg, 0.27 mmol) and 4-methyl-5-pyridin-4-yl-2,4-dihydro-[1,2,4]triazole-3-thione (22 mg, 0.11 mmol) in acetonitrile (1.5 mL) at room temperature overnight. The reaction mixture was purified by chromatography using a silica SPE tube (2-3% methanol in dichloromethane). $^1$H NMR (CDCl$_3$) δ (ppm): 8.80 (br.s, 2H), 7.85 (dd, 1H), 7.62 (d, 2H), 7.50 (m, 1H), 7.31 (t, 1H), 5.30 (q, 1H), 3.66 (s, 3H), 2.05 (d, 3H).

g) 4-(5-{1-[2-(5-Chloro-2-fluoro-phenyl)-2H-tetrazol-5-yl]-ethylsulfanyl}-4-cyclopropyl-4H-[1,2,4]triazol-3-yl)-pyridine The title compound (34.1 mg, 84%, white foam) was obtained from methanesulfonic acid 1-[2-(5-chloro-2-fluoro-phenyl)-2H-tetrazol-5-yl]-ethyl ester (~29.5 mg, 0.09 mmol) using potassium carbonate (38 mg, 0.27 mmol) and 4-cyclopropyl-5-pyridin-4-yl-2,4-dihydro-[1,2,4]triazole-3-thione (23 mg, 0.10 mmol) in acetonitrile (1.5 mL) at room temperature overnight. The reaction mixture was purified by chromatography using a silica SPE tube (2-2.5% methanol in dichloromethane). $^1$H NMR (CDCl$_3$) δ (ppm): 8.78 (d, 2H), 7.90 (dd, 1H), 7.75 (d, 2H), 7.49 (m, 1H), 7.32 (t, 1H), 5.67 (q, 1H), 3.26 (septet, 1H), 2.07 (d, 3H), 1.17 (m, 2H), 0.81 (m, 2H).

h) 4-{1-[2-(5-Chloro-2-fluoro-phenyl)-2H-tetrazol-5-yl]-ethyl}-piperazine-1-carboxylic acid ethyl ester The title compound (25.2 mg, 72%, yellow oil, ~90% pure) was prepared from methanesulfonic acid 1-[2-(5-chloro-2-fluoro-phenyl)-2H-tetrazol-5-yl]-ethyl ester (~29.5 mg, 0.09 mmol) using potassium carbonate (38 mg, 0.27 mmol) and 1-ethoxycarbonyl piperazine (20 uL, 0.14 mmol) in acetonitrile (1.5 mL) at 80° C. overnight. The product was purified by chromatography using a silica SPE tube (25-35% ethyl acetate in hexane). $^1$H NMR (CDCl$_3$) δ (ppm): 7.91 (dd, 1H), 7.51 (ddd, 1H), 7.33 (t, 1H), 4.32 (q, 1H), 4.11 (q, 2H), 3.52 (m, 4H), 2.61 (m, 2H), 2.51 (m, 2H), 1.65 (d, 3H), 1.24 (t, 3H).

i) 4-[4-Cyclopropyl-5-(2-m-tolyl-2H-tetrazol-5-ylmethylsulfanyl)-4H-[1,2,4]triazol-3-yl]-pyridine The title compound (29%, off-white solid) was obtained from methanesulfonic acid 2-m-tolyl-2H-tetrazol-5-ylmethyl ester (1 mmol) using potassium carbonate (3 mmol) and 4-cyclopropyl-5-pyridin-4-yl-2,4-dihydro-[1,2,4]triazole-3-thione (1 mmol) in acetonitrile (15 mL) at room temperature overnight. $^1$H NMR (CDCl$_3$) δ (ppm): 8.77 (d, 2H), 7.93 (s, 1H), 7.91 (d, 1H), 7.75 (d, 2H), 7.42 (t, 1H), 7.31 (d, 1H), 4.96 (s, 2H), 3.28 (m, 1H), 2.46 (s, 3H), 1.18 (m, 2H), 0.84 (m, 2H).

j) 4-{4-Cyclopropyl-5-[1-(2-m-tolyl-2H-tetrazol-5-yl)-ethylsulfanyl]-4H-[1,2,4]triazol-3-yl}-pyridine The title compound (31%, off-white solid) was obtained from methanesulfonic acid 1-(2-m-tolyl-2H-tetrazol-5-yl)-ethyl ester (1 mmol) using potassium carbonate (3 mmol) and 4-cyclopropyl-5-pyridin-4-yl-2,4-dihydro-[1,2,4]triazole-3-thione (1 mmol) in acetonitrile (15 mL) at room temperature overnight. $^1$H NMR in CDCl$_3$: 8.76 (d, 2H), 7.93 (s, 1H), 7.91 (d, 1H), 7.74 (d, 2H), 7.43 (t, 1H), 7.30 (d, 1H), 5.65 (q, 1H), 3.22 (m, 1H), 2.46 (s, 3H), 2.08 (d, 3H), 1.16 (m, 2H), 0.79 (m, 2H).

k) 4-{4-Methyl-5-[1-(2-m-tolyl-2H-tetrazol-5-yl)-ethylsulfanyl]-4H-[1,2,4]triazol-3-yl}-pyridine The title compound is obtained from methanesulfonic acid 1-(2-m-tolyl-2H-tetrazol-5-yl)-ethyl ester (1 mmol) using potassium carbonate (3 mmol) and 4-cyclopropyl-5-pyridin-4-yl-2,4-dihydro-[1,2,4]triazole-3-thione (1 mmol) in acetonitrile (15 mL) at room temperature overnight.

l) 3-[5-(4-Cyclopropyl-5-pyridin-4-yl-4H-[1,2,4]triazol-3-ylsulfanylmethyl)-tetrazol-2-yl]-benzonitrile The title compound is obtained from methanesulfonic acid 2-(3-cyano-phenyl)-2H-tetrazol-5-ylmethyl ester (1 mmol) using potassium carbonate (3 mmol) and 4-cyclopropyl-5-pyridin-4-yl-2,4-dihydro-[1,2,4]triazole-3-thione (1 mmol) in acetonitrile (15 mL) at room temperature overnight.

m) 3-{5-[1-(4-Cyclopropyl-5-pyridin-4-yl-4H-[1,2,4]triazol-3-ylsulfanyl)-ethyl]-tetrazol-2-yl}-benzonitrile The title compound is obtained methanesulfonic acid 1-[2-(3-cyano-phenyl)-2H-tetrazol-5-yl]-ethyl ester (1 mmol) using potassium carbonate (3 mmol) and 4-cyclopropyl-5-pyridin-4-yl-2,4-dihydro-[1,2,4]triazole-3-thione (1 mmol) in acetonitrile (15 mL) at room temperature overnight.

n) 3-{5-[1-(4-Methyl-5-pyridin-4-yl-4H-[1,2,4]triazol-3-ylsulfanyl)-ethyl]-tetrazol-2-yl}benzonitrile The title compound is obtained methanesulfonic acid 1-[2-(3-cyano-phenyl)-2H-tetrazol-5-yl]-ethyl ester (1 mmol) using potassium carbonate (3 mmol) and 4-cyclopropyl-5-pyridin-4-yl-2,4-dihydro-[1,2,4]triazole-3-thione (1 mmol) in acetonitrile (15 mL) at room temperature overnight.

o) 4-{4-Cyclopropyl-5-[2-(2-fluoro-5-methyl-phenyl)-2H-tetrazol-5-ylmethylsulfanyl]-4H-[1,2,4]triazol-3-yl}-pyridine The title compound is obtained from methanesulfonic acid 2-(2-fluoro-5-methyl-phenyl)-2H-tetrazol-5-ylmethyl ester (1 mmol) using potassium carbonate (3 mmol) and 4-cyclopropyl-5-pyridin-4-yl-2,4-dihydro-[1,2,4]triazole-3-thione (1 mmol) in acetonitrile (15 mL) at room temperature overnight.

p) 4-(4-Cyclopropyl-5-{1-[2-(2-fluoro-5-methyl-phenyl)-2H-tetrazol-5-yl]-ethylsulfanyl}-4H-[1,2,4]triazol-3-yl)-pyridine The title compound is obtained from methanesulfonic acid 1-[2-(2-fluoro-5-methyl-phenyl)-2H-tetrazol-5-yl]-ethyl ester (1 mmol) using potassium carbonate (3 mmol) and 4-cyclopropyl-5-pyridin-4-yl-2,4-dihydro-[1,2,4]triazole-3-thione (1 mmol) in acetonitrile (15 mL) at room temperature overnight.

q) 4-(5-{1-[2-(2-Fluoro-5-methyl-phenyl)-2H-tetrazol-5-yl]-ethylsulfanyl}-4-methyl-4H-[1,2,4]triazol-3-yl)-pyridine The title compound is obtained from methanesulfonic acid 1-[2-(2-fluoro-5-methyl-phenyl)-2H-tetrazol-5-yl]-ethyl ester (1 mmol) using potassium carbonate (3 mmol) and 4-cyclopropyl-5-pyridin-4-yl-2,4-dihydro-[1,2,4]triazole-3-thione (1 mmol) in acetonitrile (15 mL) at room temperature overnight.

In a similar manner, the following compounds were prepared:

r) 3-[4-methyl-5-({[2-(3-methylphenyl)-2H-tetrazol-5-yl]methyl}thio)-4H-1,2,4-triazol-3-yl]benzonitrile;

yield 7.1 mg, 23%, clear oil; $^1$HNMR CDCl$_3$: 7.93 (m, 4H), 7.82 (d of t, 1H), 7.67 (t, 1H), 7.44 (t, 1H), 7.28 (d, 1H), 4.82 (s, 2H), 3.64 (s, 3H), 2.47 (s, 3H).

s) 5-({[5-(3,5-difluorophenyl)-4-ethyl-4H-1,2,4-triazol-3-yl]thio}methyl)-2-(3-methylphenyl)-2H-tetrazole;

yield 23.7 mg, 77%, clear oil; $^1$H NMR CDCl$_3$: 7.89 (m, 2H), 7.43 (t, 1H), 7.33 (d, 1H), 7.17 (d of d, 2H), 6.99 (t of t, 1H), 4.87 (s, 2H), 4.03 (q, 2H), 2.47 (s, 3H), 1.33 (t, 3H).

t) 3-[4-methyl-5-({1-[2-(3-methylphenyl)-2H-tetrazol-5-yl]ethyl}thio)-4H-1,2,4-triazol-3-yl]benzonitrile;

yield 39.1 mg, 81%, clear oil; $^1$HNMR CDCl$_3$: 7.89 (m, 4H), 7.79 (d of t, 1H), 7.66 (t, 1H), 7.41 (t, 1H), 7.33 (d, 1H), 5.24 (q, 1H), 3.55 (s, 3H), 2.46 (s, 3H), 2.04 (d, 3H).

u) 5-(1-{[5-(3,5-difluorophenyl)-4-ethyl-4H-1,2,4-triazol-3-yl]thio}ethyl)-2-(3-methylphenyl)-2H-tetrazole;

yield 34.6 mg, 66%, sticky white solid; $^1$H NMR CDCl$_3$: 7.89 (m, 2H), 7.42 (t, 1H), 7.32 (d, 1H), 7.14 (m, 2H), 6.97 (t of t, 1H), 5.36 (q, 1H), 3.95 (q, 2H), 2.46 (s, 3H), 2.05 (d, 3H), 1.27 (t, 3H).

v) 6-(4-{1-[2-(3-chlorophenyl)-2H-tetrazol-5-yl]ethyl}piperazin-1-yl)nicotinonitrile;

yield 36.9 mg, 71%, yellow solid; $^1$H NMR CDCl$_3$: 8.38 (m, 1H); 8.16 (m, 1H); 8.06 (m, 1H); 7.60 (d, 1H); 7.57 (d, 1H); 7.50 (m, 1H); 6.56 (m, 1H); 4.34 (q, 1H); 3.71 (m, 4H); 2.69 (m, 4H); 1.69 (d, 3H).

w) 3-(4-{1-[2-(3-chlorophenyl)-2H-tetrazol-5-yl]ethyl}piperazin-1-yl)pyrazine-2-carbonitrile;

yield 15.4 mg, 47%, yellow oil; $^1$H NMR CDCl$_3$: 8.23 (m, 1H); 8.18 (m, 1H); 8.07 (m, 1H); 7.99 (m, 1H); 7.50 (m, 2H); 4.34 (q, 1H); 3.87 (m, 4H); 2.75 (m, 4H); 1.68 (d, 3H).

x) 2-(4-{1-[2-(3-chlorophenyl)-2H-tetrazol-5-yl]ethyl}piperazin-1-yl)nicotinonitrile;

yield 22 mg, 42%, clear oil; $^1$H NMR CDCl$_3$: 8.33 (m, 1H); 8.19 (m, 1H); 8.08 (m, 1H); 7.75 (m, 1H); 7.51 (m, 2H); 6.73 (m, 1H); 4.33 (q, 1H); 3.77 (m, 4H); 2.75 (m, 4H); 1.68 (d, 3H).

y) 1-{1-[2-(3-chlorophenyl)-2H-tetrazol-5-yl]ethyl}-4-(3-nitropyridin-2-yl)piperazine;

yield 30.3 mg, 55%, yellow oil; $^1$H NMR CDCl$_3$: 8.29 (m, 1H); 8.18 (m, 1H); 8.08 (m, 2H); 7.50 (m, 2H); 6.73 (m, 1H); 4.33 (q, 1H); 3.47 (m, 4H); 2.71 (m, 4H); 1.67 (d, 3H).

z) 2-({1-[2-(3-chlorophenyl)-2H-tetrazol-5-yl]ethyl}thio)-imidazo[4,5-b]pyridine;

yield 53 mg, 49%, yellow solid; $^1$H NMR CDCl$_3$: 8.33 (m, 1H), 8.10 (br.s., 1H), 8.00 (m, 2H), 7.48 (m, 2H), 7.25 (m, 1H), 5.45 (q, 1H), 2.05 (d, 3H).

EXAMPLE 26 a) Methyl-(4-methyl-5-pyridin-4-yl-4H-[1,2,4]triazol-3-yl)-(2-m-tolyl-2H-tetrazol-5-ylmethyl)-amine The title compound (53%, yellow oil) was obtained from methanesulfonic acid 2-m-tolyl-2H-tetrazol-5-ylmethyl ester (1 mmol) using sodium hydride (2 mmol) and methyl-(4-methyl-5-pyridin-4-yl-4H-[1,2,4]triazol-3-yl)-amine (1.8 mmol) in DMF (5 mL) at 60° C. overnight. $^1$H NMR CDCl$_3$: 8.78 (d, 2H), 7.93 (s, 1H), 7.92 (d, 1H), 7.66 (d of d, 2H), 7.44 (t, 1H), 7.33 (d, 1H), 4.75 (s, 2H), 3.76 (s, 3H), 3.09 (s, 3H), 2.48 (s, 3H).

Examples 26b to 26an may be prepared as described for example 26a.

b) Methyl-(4-methyl-5-pyridin-4-yl-4H-[1,2,4]triazol-3-yl)-[1-(2-m-tolyl-2H-tetrazol-5-yl)-ethyl]-amine The title compound (50%, yellow oil) was obtained from methanesulfonic acid 1-(2-m-tolyl-2H-tetrazol-5-yl)-ethyl ester (1 mmol) using sodium hydride (2 mmol) and methyl-(4-methyl-5-pyridin-4-yl-4H-[1,2,4]triazol-3-yl)-amine (1.8 mmol) in DMF (5 mL) at 60° C. overnight. ¹H NMR CDCl₃: 8.77 (d, 2H), 7.94 (s, 1H), 7.92 (d, 1H), 7.67 (d of d, 2H), 7.44 (t, 1H), 7.32 (d, 1H), 5.08 (q, 1H), 3.76 (s, 3H), 2.96 (s, 3H), 2.48 (s, 3H), 1.85 (d, 3H).

c) [2-(3-Chloro-phenyl)-2H-tetrazol-5-ylmethyl]-methyl-(4-methyl-5-pyridin-4-yl-4H-[1,2,4]triazol-3-yl)-amine The title compound is obtained from methanesulfonic acid 1-[2-(3-chlorophenyl)-2H-tetrazol-5-yl]-ethyl ester (1 mmol) using sodium hydride (2 mmol) and methyl-(4-methyl-5-pyridin-4-yl-4H-[1,2,4]triazol-3-yl)-amine (1.8 mmol) in DMF (5 mL) at 60° C. overnight.

d) {1-[2-(3-Chloro-phenyl)-2H-tetrazol-5-yl]-ethyl}-methyl-(4-methyl-5-pyridin-4-yl-4H-[1,2,4]triazol-3-yl)-amine The title compound is obtained from methanesulfonic acid 1-[2-(3-chlorophenyl)-2H-tetrazol-5-yl]-ethyl ester (1 mmol) using sodium hydride (2 mmol) and methyl-(4-methyl-5-pyridin-4-yl-4H-[1,2,4]triazol-3-yl)-amine (1.8 mmol) in DMF (5 mL) at 60° C. overnight.

e) [2-(2-Fluoro-5-methyl-phenyl)-2H-tetrazol-5-ylmethyl]-methyl-(4-methyl-5-pyridin-4-yl-4H-[1,2,4]triazol-3-yl)-amine The title compound is obtained from methanesulfonic acid 2-(2-fluoro-5-methyl-phenyl)-2H-tetrazol-5-ylmethyl ester 1-[2-(3-chlorophenyl)-2H-tetrazol-5-yl]-ethyl ester (1 mmol) using sodium hydride (2 mmol) and methyl-(4-methyl-5-pyridin-4-yl-4H-[1,2,4]triazol-3-yl)-amine (1.8 mmol) in DMF (5 mL) at 60° C. overnight.

f) {1-[2-(2-Fluoro-5-methyl-phenyl)-2H-tetrazol-5-yl]-ethyl}-methyl-(4-methyl-5-pyridin-4-yl-4H-[1,2,4]triazol-3-yl)-amine The title compound is obtained from methanesulfonic acid 1-[2-(2-fluoro-5-methyl-phenyl)-2H-tetrazol-5-yl]-ethyl ester (1 mmol) sodium hydride (2 mmol) and methyl-(4-methyl-5-pyridin-4-yl-4H-[1,2,4]triazol-3-yl)-amine (1.8 mmol) in DMF (5 mL) at 60° C. overnight.

g) [2-(3-Iodo-phenyl)-2H-tetrazol-5-ylmethyl]-methyl-(4-methyl-5-pyridin-4-yl-4H-[1,2,4]triazol-3-yl)-amine The title compound is obtained from methanesulfonic acid 2-(3-iodo-phenyl)-2H-tetrazol-5-ylmethyl ester (1 mmol) using sodium hydride (2 mmol) and methyl-(4-methyl-5-pyridin-4-yl-4H-[1,2,4]triazol-3-yl)-amine (1.8 mmol) in DMF (5 mL) at 60° C. overnight.

h) {1-[2-(3-Iodo-phenyl)-2H-tetrazol-5-yl]-ethyl}-methyl-(4-methyl-5-pyridin-4-yl-4H-[1,2,4]triazol-3-yl)-amine The title compound is obtained from methanesulfonic acid methanesulfonic acid 1-[2-(3-iodo-phenyl)-2H-tetrazol-5-yl]-ethyl ester (1 mmol) using sodium hydride (2 mmol) and methyl-(4-methyl-5-pyridin-4-yl-4H-[1,2,4]triazol-3-yl)-amine (1.8 mmol) in DMF (5 mL) at 60° C. overnight.

i) Methyl-(4-methyl-5-pyridin-4-yl-4H-[1,2,4]triazol-3-yl)-(2-m-tolyl-2H-tetrazol-5-ylmethyl)-amine The title compound (74%, yellow solid) was obtained from methanesulfonic acid 2-m-tolyl-2H-tetrazol-5-ylmethyl ester (1 mmol) using sodium hydride (2 mmol) and 3-Pyridin-4-yl-5,6,7,8-tetrahydro-[1,2,4]triazolo[4,3-a]pyrimidine (1.8 mmol) in DMF (5 mL) at room temperature overnight. ¹H NMR CDCl₃: 8.72 (s br, 2H), 7.92 (s, 1H), 7.90 (d, 1H), 7.63 (d, 2H), 7.42 (t, 1H), 7.30 (d, 1H), 5.19 (s, 2H), 4.16 (t, 2H), 3.62 (t, 2H), 2.47 (s, 3H), 2.25 (m, 2H).

j) Methyl-(4-methyl-5-pyridin-4-yl-4H-[1,2,4]triazol-3-yl)-[1-(2-m-tolyl-2H-tetrazol-5-yl)-ethyl]-amine The title compound (89%, yellow-brown solid) was obtained from methanesulfonic acid 1-(2-m-tolyl-2H-tetrazol-5-yl)-ethyl ester (1 mmol) using sodium hydride (2 mmol) and 3-Pyridin-4-yl-5,6,7,8-tetrahydro-[1,2,4]triazolo[4,3-a]pyrimidine (1.8 mmol) in DMF (5 mL) at room temperature overnight. ¹H NMR CDCl₃: 8.71 (d of d, 2H), 7.92 (m, 2H), 7.62 (d of d, 2H), 7.42 (t, 1H), 7.29 (d, 1H), 6.18 (q, 1H), 4.13 (m, 2H), 3.48 (m, 2H), 2.46 (s, 3H), 2.18 (m, 2H), 1.84 (d, 3H).

k) [2-(3-Chloro-phenyl)-2H-tetrazol-5-ylmethyl]-methyl-(4-methyl-5-pyridin-4-yl-4H-[1,2,4]triazol-3-yl)-amine The title compound is obtained from methanesulfonic acid 1-[2-(3-chlorophenyl)-2H-tetrazol-5-yl]-ethyl ester (1 mmol) using sodium hydride (2 mmol) and 3-Pyridin-4-yl-5,6,7,8-tetrahydro-[1,2,4]triazolo[4,3-a]pyrimidine (1.8 mmol) in DMF (5 mL) at room temperature overnight.

l) {1-[2-(3-Chloro-phenyl)-2H-tetrazol-5-yl]-ethyl}-methyl-(4-methyl-5-pyridin-4-yl-4H-[1,2,4]triazol-3-yl)-amine The title compound (42.1 mg, 63%, yellow solid) was obtained from methanesulfonic acid 1-[2-(3-chlorophenyl)-2H-tetrazol-5-yl]-ethyl ester (1 mmol) using sodium hydride (2 mmol) and 3-Pyridin-4-yl-5,6,7,8-tetrahydro-[1,2,4]triazolo[4,3-a]pyrimidine (1.8 mmol) in DMF (5 mL) at room temperature overnight. ¹H NMR CDCl₃: 8.72 (d, 2H), 8.15 (s, 1H), 8.03 (m, 1H), 7.62 (d, 2H), 7.5 (t, 2H), 6.16 (q, 1H), 4.12 (m, 2H), 3.5 (m, 2H), 2.2 (m, 2H), 1.84 (d, 3H)

m) [2-(2-Fluoro-5-methyl-phenyl)-2H-tetrazol-5-ylmethyl]-methyl-(4-methyl-5-pyridin-4-yl-4H-[1,2,4]triazol-3-yl)-amine The title compound is obtained from methanesulfonic acid 2-(2-fluoro-5-methyl-phenyl)-2H-tetrazol-5-ylmethyl ester 1-[2-(3-chlorophenyl)-2H-tetrazol-5-yl]-ethyl ester (1 mmol) using sodium hydride (2 mmol) and 3-Pyridin-4-yl-5,6,7,8-tetrahydro-[1,2,4]triazolo[4,3-a]pyrimidine (1.8 mmol) in DMF (5 mL) at room temperature overnight.

n) {1-[2-(2-Fluoro-5-methyl-phenyl)-2H-tetrazol-5-yl]-ethyl}-methyl-(4-methyl-5-pyridin-4-yl-4H-[1,2,4]triazol-3-yl)-amine The title compound is obtained from methanesulfonic acid 1-[2-(2-fluoro-5-methyl-phenyl)-2H-tetrazol-5-yl]-ethyl ester (1 mmol) using sodium hydride (2 mmol) and 3-Pyridin- 4-yl-5,6,7,8-tetrahydro-[1,2,4]triazolo[4,3-a]pyrimidine (1.8 mmol) in DMF (5 mL) at room temperature overnight.

o) 8-[2-(3-Iodo-phenyl)-2H-tetrazol-5-ylmethyl]-3-pyridin-4-yl-5,6,7,8-tetrahydro-[1,2,4]triazolo[4,3-a]pyrimidine The title compound is obtained from methanesulfonic acid 2-(3-iodo-phenyl)-2H-tetrazol-5-ylmethyl ester (1 mmol) using sodium hydride (2 mmol) and 3-Pyridin-4-yl-5,6,7,8-tetrahydro-[1,2,4]triazolo[4,3-a]pyrimidine (1.8 mmol) in DMF (5 mL) at room temperature overnight.

p) 8-{1-[2-(3-Iodo-phenyl)-2H-tetrazol-5-yl]-ethyl}-3-pyridin-4-yl-5,6,7,8-tetrahydro-[1,2,4]triazolo[4,3-a]pyrimidine The title compound is obtained from methanesulfonic acid 1-[2-(3-iodo-phenyl)-2H-tetrazol-5-yl]-ethyl ester (1 mmol) using sodium hydride (2 mmol) and 3-Pyridin-4-yl-5,6,7,8-tetrahydro-[1,2,4]triazolo[4,3-a]pyrimidine (1.8 mmol) in DMF (5 mL) at room temperature overnight.

q) 3-Pyridin-4-yl-8-(2-m-tolyl-2H-tetrazol-5-ylmethyl)-5,6,7,8-tetrahydro-4H-1,2,3a,8-tetraaza-azulene The title compound is obtained from methanesulfonic acid 2-m-tolyl-2H-tetrazol-5-ylmethyl ester (1 mmol) using sodium hydride (2 mmol) and 3-Pyridin-4-yl-5,6,7,8-tetrahydro-4H-1,2,3a,8-tetraaza-azulene (1.8 mmol) in DMF (5 mL) at room temperature overnight.

r) 3-Pyridin-4-yl-8-[1-(2-m-tolyl-2H-tetrazol-5-yl)-ethyl]-5,6,7,8-tetrahydro-4H-1,2,3a,8-tetraaza-azulene The title compound is obtained from methanesulfonic acid 1-(2-m-tolyl-2H-tetrazol-5-yl)-ethyl ester (1 mmol) using sodium hydride (2 mmol) and 3-Pyridin-4-yl-5,6,7,8-tetrahydro-4H-1,2,3a,8-tetraaza-azulene (1.8 mmol) in DMF (5 mL) at room temperature overnight.

s) 8-[2-(3-Chloro-phenyl)-2H-tetrazol-5-ylmethyl]-3-pyridin-4-yl-5,6,7,8-tetrahydro-4H-1,2,3a,8-tetraaza-azulene The title compound (39.6 mg, 53%; orange solid) was obtained from methanesulfonic acid 1-[2-(3-chlorophenyl)-2H-tetrazol-5-yl]-ethyl ester (1 mmol) using sodium hydride (2 mmol) and 3-Pyridin-4-yl-5,6,7,8-tetrahydro-4H-1,2,3a,8-tetraaza-azulene (1.8 mmol) in DMF (5 mL) at room temperature overnight. $^1$H NMR CDCl$_3$: 8.76 (d, 2H), 8.17 (s, 1H), 8.05 (d, 1H), 7.51 (d, 4H), 5.08 (br, 2H), 4.07 (br, 2H), 3.4 (br, 2H), 1.96 (br, 2H)

t) 8-{1-[2-(3-Chloro-phenyl)-2H-tetrazol-5-yl]-ethyl}-3-pyridin-4-yl-5,6,7,8-tetrahydro-4H-1,2,3a,8-tetraaza-azulene The title compound is obtained from methanesulfonic acid 1-[2-(3-chlorophenyl)-2H-tetrazol-5-yl]-methyl ester (1 mmol) using sodium hydride (2 mmol) and 3-Pyridin-4-yl-5,6,7,8-tetrahydro-4H-1,2,3a,8-tetraaza-azulene (1.8 mmol) in DMF (5 mL) at room temperature overnight.

u) 8-[2-(2-Fluoro-5-methyl-phenyl)-2H-tetrazol-5-ylmethyl]-3-pyridin-4-yl-5,6,7,8-tetrahydro-4H-1,2,3a,8-tetraaza-azulene The title compound is obtained from methanesulfonic acid 2-(2-fluoro-5-methyl-phenyl)-2H-tetrazol-5-ylmethyl ester 1-[2-(3-chlorophenyl)-2H-tetrazol-5-yl]-ethyl ester (1 mmol) using sodium hydride (2 mmol) and 3-Pyridin-4-yl-5,6,7,8-tetrahydro-4H-1,2,3a,8-tetraaza-azulene (1.8 mmol) in DMF (5 mL) at room temperature overnight.

v) 8-{1-[2-(2-Fluoro-5-methyl-phenyl)-2H-tetrazol-5-yl]-ethyl}-3-pyridin-4-yl-5,6,7,8-tetrahydro-4H-1,2,3a,8-tetraaza-azulene The title compound is obtained from methanesulfonic acid 1-[2-(2-fluoro-5-methyl-phenyl)-2H-tetrazol-5-yl]-ethyl ester (1 mmol) using sodium hydride (2 mmol) and 3-Pyridin-4-yl-5,6,7,8-tetrahydro-4H-1,2,3a,8-tetraaza-azulene (1.8 mmol) in DMF (5 mL) at room temperature overnight.

w) 8-[2-(3-Iodo-phenyl)-2H-tetrazol-5-ylmethyl]-3-pyridin-4-yl-5,6,7,8-tetrahydro-4H-1,2,3a,8-tetraaza-azulene The title compound is obtained from methanesulfonic acid 2-(3-iodo-phenyl)-2H-tetrazol-5-ylmethyl ester (1 mmol) using sodium hydride (2 mmol) and 3-Pyridin-4-yl-5,6,7,8-tetrahydro-4H-1,2,3a,8-tetraaza-azulene (1.8 mmol) in DMF (5 mL) at room temperature overnight.

x) 8-{1-[2-(3-Iodo-phenyl)-2H-tetrazol-5-yl]-ethyl}-3-pyridin-4-yl-5,6,7,8-tetrahydro-4H-1,2,3a,8-tetraaza-azulene The title compound is obtained from methanesulfonic acid 1-[2-(3-iodo-phenyl)-2H-tetrazol-5-yl]-ethyl ester (1 mmol) using sodium hydride (2 mmol) and 3-Pyridin-4-yl-5,6,7,8-tetrahydro-4H-1,2,3a,8-tetraaza-azulene (1.8 mmol) in DMF (5 mL) at room temperature overnight.

y) {1-[2-(3-Chloro-phenyl)-2H-tetrazol-5-yl]-ethyl}-methyl-(4-methyl-5-pyridin-3-yl-4H-[1,2,4]triazol-3-yl)-amine The title compound is obtained from methanesulfonic acid 1-[2-(3-chlorophenyl)-2H-tetrazol-5-yl]-ethyl ester (1 mmol) using sodium hydride (2 mmol) and methyl-(4-methyl-5-pyridin-3-yl-4H-[1,2,4]triazol-3-yl)-amine (1.8 mmol) in DMF (5 mL) at room temperature overnight.

z) {1-[2-(3-Chloro-phenyl)-2H-tetrazol-5-yl]-ethyl}-[5-(3,5-difluoro-phenyl)-4-methyl-4H-[1,2,4]triazol-3-yl]-methyl-amine The title compound is obtained from methanesulfonic acid 1-[2-(3-chlorophenyl)-2H-tetrazol-5-yl]-ethyl ester (1 mmol) using sodium hydride (2 mmol) and [5-(3,5-difluoro-phenyl)-4-methyl-4H-[1,2,4]triazol-3-yl]-methyl-amine (1.8 mmol) in DMF (5 mL) at room temperature overnight.

aa) 8-{1-[2-(3-Chloro-phenyl)-2H-tetrazol-5-yl]-ethyl}-3-pyridin-3-yl-5,6,7,8-tetrahydro-[1,2,4]triazolo[4,3-a]pyrimidine The title compound is obtained from methanesulfonic acid 1-[2-(3-chlorophenyl)-2H-tetrazol-5-yl]-ethyl ester (1 mmol) using sodium hydride (2 mmol) and 3-pyridin-3-yl-5,6,7,8-tetrahydro-[1,2,4]triazolo[4,3-a]pyrimidine (1.8 mmol) in DMF (5 mL) at room temperature overnight.

ab) 8-{1-[2-(3-Chloro-phenyl)-2H-tetrazol-5-yl]-ethyl}-3-(3,5-difluoro-phenyl)-5,6,7,8-tetrahydro-[1,2,4]triazolo[4,3-a]pyrimidine The title compound is obtained from methanesulfonic acid 1-[2-(3-chlorophenyl)-2H-tetrazol-5-yl]-ethyl ester (1 mmol) using sodium hydride (2 mmol) and 3-(3,5-Difluoro-phenyl)-5,6,7,8-tetrahydro-[1,2,4]triazolo[4,3-a]pyrimidine (1.8 mmol) in DMF (5 mL) at room temperature overnight.

ac) 8-[2-(3-Chloro-phenyl)-2H-tetrazol-5-ylmethyl]-3-pyridin-3-yl-5,6,7,8-tetrahydro-4H-1,2,3a,8-tetraaza-azulene The title compound is obtained from 5-bromomethyl-2-(3-chloro-phenyl)-2H-tetrazole (1 mmol) using sodium hydride (2 mmol) and 3-pyridin-3-yl-5,6,7,8-tetrahydro-4H-1,2,3a,8-tetraaza-azulene (1.8 mmol) in DMF (5 mL) at room temperature overnight.

ad) 8-[2-(3-Chloro-phenyl)-2H-tetrazol-5-ylmethyl]-3-(3,5-difluoro-phenyl)-5,6,7,8-tetrahydro-4H-1,2,3a,8-tetraaza-azulene The title compound is obtained from 5-bromomethyl-2-(3-chloro-phenyl)-2H-tetrazole (1 mmol) using sodium hydride (2 mmol) and 3-(3,5-Difluoro-phenyl)-5,6,7,8-tetrahydro-4H-1,2,3a,8-tetraaza-azulene (1.8 mmol) in DMF (5 mL) at room temperature overnight.

In a similar manner, the following compounds were prepared:

ae) 8-{1-[2-(3-chlorophenyl)-2H-tetrazol-5-yl]ethyl}-3-(3,5-difluorophenyl)-5,6,7,8-tetrahydro[1,2,4]triazolo[4,3-a]pyrimidine;

yield 40.4 mg, 55%, light yellow solid; $^1$H NMR CDCl$_3$: 8.15 (s, 1H), 8.03 (m, 1H), 7.5 (m, 2H), 7.25 (m, 2H), 6.89 (m, 1H), 6.16 (q, 1H), 4.07 (m, 2H), 3.48 (m, 2H), 2.2 (m, 2H), 1.83 (d, 3H)

af) 8-{1-[2-(3-chlorophenyl)-2H-tetrazol-5-yl]ethyl}-3-(4-methoxyphenyl)-5,6,7,8-tetrahydro[1,2,4]triazolo[4,3-a]pyrimidine;

yield 40.2 mg, 56%, yellow oil; $^1$H NMR CDCl$_3$: 8.15 (s, 1H), 8.04 (m, 1H), 7.6 (d, 2H), 7.55 (d, 2H), 6.98 (d, 2H), 6.16 (q, 1H), 3.97 (t, 2H), 3.86 (s, 3H), 3.46 (m, 2H), 2.13 (m, 2H), 1.82 (d, 3H)

ag) 3-(2-chloro-6-methoxypyridin-4-yl)-8-{1-[2-(3-chlorophenyl)-2H-tetrazol-5-yl]ethyl}-5,6,7,8-tetrahydro[1,2,4]triazolo[4,3-a]pyrimidine;

yield 47.5 mg, 61%, yellow oil; $^1$H NMR CDCl$_3$: 8.15 (s, 1H), 8.04 (m, 1H), 7.5 (m, 2H), 7.47 (s, 1H), 6.92 (s, 1H), 6.17 (q, 1H), 4.09 (m, 2H), 3.98 (s, 3H), 3.49 (m, 2H), 2.18 (m, 2H), 1.85 (d, 3H)

ah) 8-{1-[2-(3-chlorophenyl)-2H-tetrazol-5-yl]ethyl}-3-(2-methoxypyridin-4-yl)-5,6,7,8-tetrahydro[1,2,4]triazolo[4,3-a]pyrimidine;

yield 167.3 mg, 77%, yellow solid; $^1$H NMR CDCl$_3$: 8.25 (d, 1H), 8.14 (s, 1H), 8.02 (m, 1H), 7.48 (m, 1H), 7.28 (d, 1H), 6.98 (s, 1H), 6.16 (q, 1H), 4.1 (m, 2H), 3.97 (s, 3H), 3.49 (m, 2H), 2.19 (m, 2H), 1.82 (d, 3H)

ai) 8-{[2-(3-chlorophenyl)-2H-tetrazol-5-yl]methyl}-3-(2-methoxypyridin-4-yl)-5,6,7,8-tetrahydro[1,2,4]triazolo[4,3-a]pyrimidine;

yield 108.2 mg, 59%, orange solid; $^1$H NMR CDCl$_3$: 8.26 (d, 1H), 8.24 (s, 1H), 8.15 (m, 1H), 7.48 (m, 2H), 7.28 (m, 1H), 6.98 (s, 1H), 5.18 (s, 2H), 4.13 (t, 2H), 3.98 (s, 3H), 3.61 (t, 2H), 2.25 (m, 2H)

aj) 3-(5-{[3-(2-methoxypyridin-4-yl)-6,7-dihydro[1,2,4]triazolo[4,3-a]pyrimidine-8(5H)-yl]methyl}-2H-tetrazol-2-yl)benzonitrile;

yield 115.6 mg, 64%, yellow foam; $^1$H NMR CDCl$_3$: 8.42 (m, 2H), 8.24 (d, 1H), 7.7 (m, 2H), 7.25 (t, 1H), 6.97 (s, 1H), 5.18 (s, 2H), 4.12 (m, 2H), 3.97 (s, 3H), 3.63 (t, 2H), 2.24 (m, 2H)

ak) 3-(2-methoxypyridin-4-yl)-8-{1-[2-(3-iodophenyl)-2H-tetrazol-5-yl]ethyl}-5,6,7,8-tetrahydro[1,2,4]triazolo[4,3-a]pyrimidine;

yield 220 mg, 51%, yellow foam; $^1$H NMR CDCl$_3$: 8.42 (br, 1H), 8.2 (d, 1H), 8.04 (d, 1H), 7.77 (d, 1H), 7.27 (m, 2H), 6.95 (s, 1H), 6.13 (m, 1H), 4.06 (t, 2H), 3.93 (d, 3H), 3.44 (m, 2H), 2.15 (br, 2H), 1.79 (d, 3H)

al) 3-(5-{1-[3-(2-methoxypyridin-4-yl)-6,7-dihydro[1,2,4]triazolo[4,3-a]pyrimidin-8(5H)-yl]ethyl}-2H-tetrazol-2-yl)benzonitrile;

yield 87.8 mg, 58%, off white solid; $^1$H NMR CDCl$_3$: 8.44 (s, 1H), 8.37 (d, 1H), 8.26 (d, 1H), 7.77 (m, 2H), 7.29 (m, 1H), 6.98 (s, 1H), 6.18 (q, 1H), 4.12 (m, 2H), 3.98 (s, 3H), 3.52 (m, 2H), 2.19 (m, 2H), 1.85 (d, 3H)

am) 3-(5-{[3-(2-methoxypyridin-4-yl)-5,6,7,8-tetrahydro-9H-[1,2,4]triazolo[4,3-α][1,3]diazepin-9-yl]methyl}-2H-tetrazol-2-yl)benzonitrile;

yield 32%; $^1$H NMR CDCl$_3$: 8.44 (s, 1H), 8.40 (d, 1H), 8.26 (d, 1H), 7.76 (d, 1H), 7.68 (t, 1H), 7.08 (d, 1H), 6.88 (s, 1H), 5.05 (s, 2H), 3.97 (s, 3H), 3.94 (m, 2H), 3.39 (m, 2H), 1.93 (m, 2H).

an) 3-(5-{[3-(2,6-dimethoxypyrimidin-4-yl)-6,7-dihydro[1,2,4]triazolo[4,3-α]pyrimidin-8(5H)-yl]methyl}-2H-tetrazol-2-yl)benzonitrile;

yield 67% $^1$H NMR (dmso-d$_6$): 8.50 (br s, 1H), 8.36 (d, 1H), 8.04 (d, 1H), 7.83 (dd, 1H), 6.96 (s, 1H), 5.06 (s, 2H), 4.44 (t, 2H), 3.91 (s, 3H), 3.88 (s, 3H), 3.49 (m, 2H), 2.10 (m, 2H).

EXAMPLE 27 a) 4-(5-{[2-(3-chlorophenyl)-2H-tetrazol-5-yl]methoxy}-4-methyl-4H-1,2,4-triazol-3-yl)pyridine Sodium hydride (7.5 mg, 0.187 mmol) was added to a vial containing [2-(3-chloro-phenyl)-2H-tetrazol-5-yl]-methanol (32.9 mg, 0.156 mmol) and dimethylformamide (3 mL). The reaction was allowed to stir for forty-five minutes. The vial was then capped and heated at 80° C. overnight. After cooling, water was added and an aqueous workup was done extracting with ethyl acetate three times. The combined organic layers were washed with brine, dried over sodium sulfate, filtered and concentrated. The crude product was purified by column chromatography (5% methanol in dichloromethane) to yield the title compound as a white solid (21.6 mg, 38%). $^1$H NMR (CDCl$_3$) δ (ppm): 8.79 (d, 2H), 8.22 (s, 1H), 8.09 (m, 1H), 7.64 (m, 2H), 7.54 (m, 2H), 5.96 (s, 2H), 3.64(s, 3H).

Examples 27b to 27r may be prepared as described for example 27a.

b) 4-(5-{1-[2-(3-chlorophenyl)-2H-tetrazol-5-yl]ethoxy}-4-methyl-4H-1,2,4-triazol-3-yl)pyridine The title compound (44.0 mg, 48%, clear oil) was prepared from 1-[2-(3-chloro-phenyl)-2H-tetrazol-5-yl-ethanol (54.3 mg, 0.242 mmol), sodium hydride (12.0 mg, 0.29 mmol) and 4-(5-methanesulfonyl-4-methyl-4H-[1,2,4]triazol-3-yl)-pyridine (69.1 mg, 0.29 mmol). $^1$H NMR (CDCl$_3$) δ (ppm): 8.75 (m, 2H), 8.16 (m, 1H), 8.04 (m, 1H), 7.61 (m, 2H), 7.49 (m, 2H), 6.59 (q, 1H), 3.63 (s, 3H), 2.04 (d, 3H).

c) 4-[4-Methyl-5-(2-m-tolyl-2H-tetrazol-5-ylmethoxy)-4H-[1,2,4]triazol-3-yl]-pyridine The title compound (23.6 mg, 52%, white solid) was prepared from (2-m-tolyl-2H-tetrazol-5-yl)-methanol (24.8 mg, 0.13 mmol), sodium hydride (8 mg, 0.2 mmol) and 4-(5-methanesulfonyl-4-methyl-4H-[1,2,4]triazol-3-yl)-pyridine (38 mg, 0.16 mmol). The product was purified by chromatography using a silica SPE tube (2.5-5% methanol in dichloromethane, desired product was second product eluting). $^1$H NMR (CDCl$_3$) δ (ppm): 8.78 (m, 2H), 7.98 (s, 1H), 7.97 (d, 1H), 7.64 (d, 2H), 7.46 (t, 1H), 7.34 (d, 1H), 5.94 (s, 2H), 3.63 (s, 3H), 2.50 (s, 3H).

d) 4-{4-Methyl-5-[1-(2-m-tolyl-2H-tetrazol-5-yl)-ethoxy]-4H-[1,2,4]triazol-3-yl}-pyridine The title compound (70 mg, 79%, off-white solid) was prepared from 1-(2-m-tolyl-2H-tetrazol-5-yl)-ethanol (50.3 mg, 0.24 mmol), sodium hydride (16 mg, 0.4 mmol) and 4-(5-methanesulfonyl-4-methyl-4H-[1,2,4]triazol-3-yl)-pyridine (70.2 mg, 0.30 mmol). The product was purified by chromatography using a silica SPE tube (2.5-4% methanol in dichloromethane). $^1$H NMR (CDCl$_3$) δ (ppm): 8.76 (br.d, 2H), 7.95 (s, 1H), 7.94 (d, 1H), 7.62 (d, 2H), 7.44 (t, 1H), 7.32 (d, 1H), 6.61 (q, 1H), 3.63 (s, 3H), 2.28 (s, 3H), 2.04 (d, 3H).

e) 4-{5-[2-(2-Fluoro-5-methyl-phenyl)-2H-tetrazol-5-ylmethoxy]-4-methyl-4H-[1,2,4]triazol-3-yl}-pyridine The title compound is prepared from [2-(2-fluoro-5-methyl-phenyl)-2H-tetrazol-5-yl]-methanol (1 mmol), sodium hydride (1.5 mmol) and 4-(5-methanesulfonyl-4-methyl-4H-[1,2,4]triazol-3-yl)-pyridine (1.25 mmol).

f) 4-(5-{1-[2-(2-Fluoro-5-methyl-phenyl)-2H-tetrazol-5-yl]-ethoxy}-4-methyl-4H-[1,2,4]triazol-3-yl)-pyridine The title compound is prepared from 1-[2-(2-fluoro-5-methyl-phenyl)-2H-tetrazol-5-yl]-ethanol (1 mmol), sodium hydride (1.5 mmol) and 4-(5-methanesulfonyl-4-methyl-4H-[1,2,4]triazol-3-yl)-pyridine (1.25 mmol).

g) 4-{5-[2-(3-Chloro-phenyl)-2H-tetrazol-5-ylmethoxy]-4-cyclopropyl-4H-[1,2,4]triazol-3-yl}-pyridine The title compound is prepared from [2-(3-chloro-phenyl)-2H-tetrazol-5-yl]-methanol (1 mmol), sodium hydride (1.5 mmol) and 4-(4-cyclopropyl-5-methanesulfonyl-4H-[1,2,4]triazol-3-yl)-pyridine (1.25 mmol).

h) 4-(5-{1-[2-(3-Chloro-phenyl)-2H-tetrazol-5-yl]-ethoxy}-4-cyclopropyl-4H-[1,2,4]triazol-3-yl)-pyridine The title compound is prepared from 1-[2-(3-chloro-phenyl)-2H-tetrazol-5-yl-ethanol (1 mmol), sodium hydride (1.5 mmol) 4-(4-cyclopropyl-5-methanesulfonyl-4H-[1,2,4]triazol-3-yl)-pyridine (1.25 mmol).

i) 4-[4-Cyclopropyl-5-(2-m-tolyl-2H-tetrazol-5-ylmethoxy)-4H-[1,2,4]triazol-3-yl]-pyridine The title compound (4.6 mg, 11%, yellow solid) was prepared from (2-m-tolyl-2H-tetrazol-5-yl)-methanol (1 mmol), sodium hydride (1.5 mmol) and 4-(4-cyclopropyl-5-methanesulfonyl-4H-[1,2,4]triazol-3-yl)-pyridine (1.25 mmol). $^1$H NMR (CDCl$_3$) δ (ppm): 8.77 (s br, 2H), 7.97 (m, 2H), 7.79 (d, 2H), 7.47 (t, 1H), 7.35 (d, 1H), 5.94 (s, 2H), 3.21 (m, 1H), 2.50 (s, 3H), 1.12 (m, 2H), 0.86 (m, 2H).

j) 4-{4-Cyclopropyl-5-[1-(2-m-tolyl-2H-tetrazol-5-yl)-ethoxy]-4H-[1,2,4]triazol-3-yl}-pyridine The title compound (7.8 mg, 19%, clear oil) was prepared from 1-(2-m-tolyl-2H-tetrazol-5-yl)-ethanol (1 mmol), sodium hydride (1.5 mmol) and 4-(4-cyclopropyl-5-methanesulfonyl-4H-[1,2,4]triazol-3-yl)-pyridine (1.25 mmol). $^1$H NMR (CDCl$_3$) δ (ppm): 8.73 (d, 2H), 7.93 (m, 2H), 7.78 (d, 2H), 7.45 (t, 1H), 7.33 (d, 1H), 6.62 (q, 1H), 3.22 (m, 1H), 2.49 (s, 3H), 2.05 (d, 3H), 1.14 (m, 2H), 1.00 (m, 2H).

k) 4-{4-Cyclopropyl-5-[2-(2-fluoro-5-methyl-phenyl)-2H-tetrazol-5-ylmethoxy]-4H-[1,2,4]triazol-3-yl}-pyridine The title compound is prepared from [2-(2-fluoro-5-methyl-phenyl)-2H-tetrazol-5-yl]-methanol (1 mmol), sodium hydride (1.5 mmol) and 4-(4-cyclopropyl-5-methanesulfonyl-4H-[1,2,4]triazol-3-yl)-pyridine (1.25 mmol).

l) 4-(4-Cyclopropyl-5-{1-[2-(2-fluoro-5-methyl-phenyl)-2H-tetrazol-5-yl]-ethoxy}-4H-[1,2,4]triazol-3-yl)-pyridine The title compound is prepared from 1-[2-(2-fluoro-5-methyl-phenyl)-2H-tetrazol-5-yl]-ethanol (1 mmol), sodium hydride (1.5 mmol) and 4-(4-cyclopropyl-5-methanesulfonyl-4H-[1,2,4]triazol-3-yl)-pyridine (1.25 mmol).

m) 4-{5-[2-(3-Iodo-phenyl)-2H-tetrazol-5-ylmethoxy]-4-methyl-4H-[1,2,4]triazol-3-yl}-pyridine The title compound is prepared from [2-(3-iodo-phenyl)-2H-tetrazol-5-yl]-methanol (1 mmol), sodium hydride (1.5 mmol) and 4-(5-methanesulfonyl-4-methyl-4H-[1,2,4]triazol-3-yl)-pyridine (1.25 mmol).

n) 4-(5-{1-[2-(3-Iodo-phenyl)-2H-tetrazol-5-yl]-ethoxy}-4-methyl-4H-[1,2,4]triazol-3-yl)-pyridine The title compound is prepared from 1-[2-(3-iodo-phenyl)-2H-tetrazol-5-yl-ethanol (1 mmol), sodium hydride (1.5 mmol) 4-(5-methanesulfonyl-4-methyl-4H-[1,2,4]triazol-3-yl)-pyridine (1.25 mmol).

o) 4-{4-Cyclopropyl-5-[2-(3-iodo-phenyl)-2H-tetrazol-5-ylmethoxy]-4H-[1,2,4]triazol-3-yl}-pyridine The title compound is prepared from [2-(3-iodo-phenyl)-2H-tetrazol-5-yl]-methanol (1 mmol), sodium hydride (1.5 mmol) and 4-(4-cyclopropyl-5-methanesulfonyl-4H-[1,2,4]triazol-3-yl)-pyridine (1.25 mmol).

p) 4-(4-Cyclopropyl-5-{1-[2-(3-iodo-phenyl)-2H-tetrazol-5-yl]-ethoxy)-4H-[1,2,4]triazol-3-yl)-pyridine The title compound is prepared from 1-[2-(3-iodo-phenyl)-2H-tetrazol-5-yl-ethanol (1 mmol), sodium hydride (1.5 mmol) 4-(4-cyclopropyl-5-methanesulfonyl-4H-[1,2,4]triazol-3-yl)-pyridine (1.25 mmol).

q) 3-(5-[(1-[2-(3-Chloro-phenyl)-2H-tetrazol-5-yl]-ethoxy}-4-methyl-4H-[1,2,4]triazol-3-yl)-pyridine The title compound is prepared from 1-[2-(3-chloro-phenyl)-2H-tetrazol-5-yl-ethanol (1 mmol), sodium hydride (1.5 mmol), and 3-(5-methanesulfonyl-4-methyl-4H-[1,2,4]triazol-3-yl)-pyridine (1.25 mmol).

r) 2-(3-Chloro-phenyl)-5-[(1-[5-(3,5-difluoro-phenyl)-4-methyl-4H-[1,2,4]triazol-3-yloxy]-ethyl}-2H-tetrazole The title compound is prepared from 1-[2-(3-chloro-phenyl)-2H-tetrazol-5-yl-ethanol (1 mmol), sodium hydride (1.5 mmol), and 3-(3,5-Difluoro-phenyl)-5-methanesulfonyl-4-methyl-4H-[1,2,4]triazole (1.25 mmol).

EXAMPLE 28 a) 3-[5-(4-Methyl-5-pyridin-4-yl-4H-1,2,4]triazol-3-yloxymethyl)-tetrazol-2-yl]-benzonitrile The title compound is prepared from 4-{5-[2-(3-iodo-phenyl)-2H-tetrazol-5-ylmethoxy]-4-methyl-4H-[1,2,4]triazol-3-yl}-pyridine (1 mmol), zinc cyanide (1.1 mmol), palladium (0) tetrakis-triphenylphosphine (0.05 mmol) in DMF (5 mL) at 80° C. overnight. The solvent is removed in vacuo, and the product is purified by flash chromatography.

Examples 28b to 28j were prepared as described for example 28a.

b) 3-{5-[1-(4-Methyl-5-pyridin-4-yl-4H-[1,2,4]triazol-3-yloxy)-ethyl]-tetrazol-2-yl}-benzonitrile The title compound is prepared from 4-(5-{1-[2-(3-iodo-phenyl)-2H-tetrazol-5-yl]-ethoxy}-4-methyl-4H-[1,2,4]triazol-3-yl)-pyridine (1 mmol), zinc cyanide (1.1 mmol), palladium (0) tetrakis-triphenylphosphine (0.05 mmol) in DMF (5 mL) at 80° C. overnight.

c) 3-[5-(4-Cyclopropyl-5-pyridin-4-yl-4H-[1,2,4]triazol-3-yloxymethyl)-tetrazol-2-yl]-benzonitrile The title compound is prepared from 4-{4-cyclopropyl-5-[2-(3-iodo-phenyl)-2H-tetrazol-5-ylmethoxy]-4H-[1,2,4]triazol-3-yl}-pyridine (1 mmol), zinc cyanide (1.1 mmol), palladium (0) tetrakis-triphenylphosphine (0.05 mmol) in DMF (5 mL) at 80° C. overnight.

d) 3-{5-[1-(4-Cyclopropyl-5-pyridin-4-yl-4H-[1,2,4]triazol-3-yloxy)-ethyl]-tetrazol-2-yl}-benzonitrile The title compound is prepared from 4-(4-cyclopropyl-5-{1-[2-(3-iodo-phenyl)-2H-tetrazol-5-yl]-ethoxy}-4H-[1,2,4]triazol-3-yl)-pyridine (1 mmol), zinc cyanide (1.1 mmol), palladium (0) tetrakis-triphenylphosphine (0.05 mmol) in DMF (5 mL) at 80° C. overnight.

e) 3-(5-{[Methyl-(4-methyl-5-pyridin-4-yl-4H-[1,2,4]triazol-3-yl)-amino]-methyl}-tetrazol-2-yl)-benzonitrile The title compound is prepared from [2-(3-Iodo-phenyl)-2H-tetrazol-5-ylmethyl]-methyl-(4-methyl-5-pyridin-4-yl-4H-[1,2,4]triazol-3-yl)-amine (1 mmol), zinc cyanide (1.1 mmol), palladium (0) tetrakis-triphenylphosphine (0.05 mmol) in DMF (5 mL) at 80° C. overnight.

f) 3-(5-{1-[Methyl-(4-methyl-5-pyridin-4-yl-4H-[1,2,4]triazol-3-yl)-amino]-ethyl}-tetrazol-2-yl)-benzonitrile The title compound is prepared from {1-[2-(3-Iodo-phenyl)-2H-tetrazol-5-yl]-ethyl}-methyl-(4-methyl-5-pyridin-4-yl-4H-[1,2,4]triazol-3-yl)-amine (1 mmol), zinc cyanide (1.1 mmol), palladium (0) tetrakis-triphenylphosphine (0.05 mmol) in DMF (5 mL) at 80° C. overnight.

g) 3-[5-(3-Pyridin-4-yl-6,7-dihydro-5H-[1,2,4]triazolo[4,3-a]pyrimidin-8-ylmethyl)-tetrazol-2-yl]-benzonitrile The title compound is prepared from 8-[2-(3-iodo-phenyl)-2H-tetrazol-5-ylmethyl]-3-pyridin-4-yl-5,6,7,8-tetrahydro-[1,2,4]triazolo[4,3-a]pyrimidine (1 mmol), zinc cyanide (1.1 mmol), palladium (0) tetrakis-triphenylphosphine (0.05 mmol) in DMF (5 mL) at 80° C. overnight.

h) 3-{5-[1-(3-Pyridin-4-yl-6,7-dihydro-5H-[1,2,4]triazolo[4,3-a]pyrimidin-8-yl)-ethyl]-tetrazol-2-yl}-benzonitrile The title compound is prepared from 8-{1-[2-(3-iodo-phenyl)-2H-tetrazol-5-yl]-ethyl}-3-pyridin-4-yl-5,6,7,8-tetrahydro-[1,2,4]triazolo[4,3-a]pyrimidine (1 mmol), zinc cyanide (1.1 mmol), palladium (0) tetrakis-triphenylphosphine (0.05 mmol) in DMF (5 mL) at 80° C. overnight.

i) 3-[5-(3-Pyridin-4-yl-4,5,6,7-tetrahydro-1,2,3a,8-tetraaza-azulen-8-ylmethyl)-tetrazol-2-yl]-benzonitrile The title compound is prepared from 8-[2-(3-iodo-phenyl)-2H-tetrazol-5-ylmethyl]-3-pyridin-4-yl-5,6,7,8-tetrahydro-4H-1,2,3a,8-tetraaza-azulene (1 mmol), zinc cyanide (1.1 mmol), palladium (0) tetrakis-triphenylphosphine (0.05 mmol) in DMF (5 mL) at 80° C. overnight.

j) 3-{5-[1-(3-Pyridin-4-yl-4,5,6,7-tetrahydro-1,2,3a, 8-tetraaza-azulen-8-yl)-ethyl]-tetrazol-2-yl}-benzonitrile The title compound is prepared from 8-{1-[2-(3-iodo-phenyl)-2H-tetrazol-5-yl]-ethyl}-3-pyridin-4-yl-5,6,7,8-tetrahydro-4H-1,2,3a,8-tetraaza-azulene (1 mmol), zinc cyanide (1.1 mmol), palladium (0) tetrakis-triphenylphosphine (0.05 mmol) in DMF (5 mL) at 80° C. overnight.

EXAMPLE 29 a1) & a2) (R) & (S)-4-(5-{1-[2-(3-chlorophenyl)-2H-tetrazol-5-yl]ethoxy}-4-methyl-4H-1,2,4-triazol-3-yl)pyridine The racemic mixture of 4-(5-{1-[2-(3-chlorophenyl)-2H-tetrazol-5-yl]ethoxy}-4-methyl-4H-1,2,4-triazol-3-yl)pyridine was separated with a chiralpak AD column (4.6×250) using 50% isopropanol and 50% ethanol and a flow rate of 2.0 mL/minute. The first enantiomer (15.6 mg) had a retention time of 6.10 minutes and the second enantiomer (9.5 mg) had a retention time of 11.97 minutes.

In a similar manner, the following compounds were prepared:

b1) & b2) (R) and (S) 3-(5-{1-[3-(2-methoxypyridin-4-yl)-6,7-dihydro[1,2,4]triazolo[4,3-a]pyrimidin-8(5H)-yl]ethyl}-2H-tetrazol-2-yl)benzonitrile HPLC conditions: Chiralpak AD; 39° C.; iPrOH; 4.6×250 mm; 1 mL/min; Rt=6.93 min (b1), 11.93 min (b2); semi-prep 21×250 mm @ 20 mL/min.; yield 19.3 mg b1 and 18.5 mg b2 c1) & c2) (R) and (S) ethyl 4-{1-[2-(3-chlorophenyl)-2H-tetrazol-5-yl]ethyl}piperazine-1-carboxylate HPLC conditions: Chiralpak AD; semi-prep 21×250 mm @ 20 mL/min with 50:50 iPrOH/hexane; Rt=22 min (E1), 42.5 min (E2); 16 mg E1 and 14 mg E2 d1) & d2) (R) and (S) ethyl 4-{1-[2-(5-chloro-2-fluorophenyl)-2H-tetrazol-5-yl]ethyl}piperazine-1-carboxylate HPLC conditions: Chiralpak AD; EtOH; 4.6×250 mm; 1 mL/min; Rt=6.1 min (E1), 6.7 min (E2); semi-prep 21×250 mm @ 20 mL/min with 70:30 EtOH/hexane->5 mg E1 and 6 mg E2 e1) & e2) (R) and (S) 6-(4-{1-[2-(3-chlorophenyl)-2H-tetrazol-5-yl]ethyl}piperazin-1-yl)nicotinonitrile HPLC conditions: Chiralpak AD; 39° C.; MeOH; 4.6×250 mm; 2 mL/min; Rt=14.3 min (e1), 34.8 min (e2); semi-prep 21×250 mm @ 20 mL/min.; yield e1: 37.8 mg white solid; e2: 37 mg white solid f1) & f2) (R) and (S) 3-(4-{1-[2-(3-chlorophenyl)-2H-tetrazol-5-yl]ethyl}piperazin-1-yl)pyrazine-2-carbonitrile Chiralpak AD; 39° C.; MeOH; 4.6×250 mm; 2 mL/min; Rt=10.9 min (f1), 17.4 min ([2); semi-prep 21×250 mm @ 20 mL/min.; yield f1: 29.2 mg viscous yellow oil; f2: 28.7 mg viscous yellow oil

EXAMPLE 30 a) 2-(3-chloro-phenyl)-5-[(triphenyl-$\lambda^5$-phosphanyl)-methyl]-2H-tetrazole hydrobromide Triphenylphosphine (89.4 mg, 0.341 mmol) was added to 5-bromomethyl-2-(3-chloro-phenyl)-2H-tetrazole (93.2 mg, 0.341 mmol) in toluene (5 mL). The reaction was heated at 80° C. under Argon for 4.5 hours. The reaction was cooled and concentrated to yield the title compound as a white solid (165.1 mg, 90%). $^1$H NMR CDCl$_3$ δ (ppm): 7.96 (m, 6H), 7.80 (m, 4H), 7.70 (m, 6H), 7.44 (d, 2H), 7.28 (s, 1H), 6.17 (d, 2H).

b) 4-(5-{2-[2-(3-chloro-phenyl)-2H-tetrazol-5-yl]-vinyl}-4-ethyl-4H-[1,2,4]triazol-3-yl)-pyridine 4-Ethyl-5-pyridin-4-yl-4H-[1,2,4]triazole-3-carbaldehyde (56.4 mg, 0.279 mmol) was dissolved in dimethylformamide (2 mL) and added to a vial containing 2-(3-chloro-phenyl)-5-[(triphenyl-$\lambda^5$-phosphanyl)-methyl]-2H-tetrazole hydrobromide (165.1 mg, 0.307 mmol) dissolved in dimethylformamide (2 mL). After addition of DBU (84.9 mg, 0.558 mmol), the vial was capped and the reaction was allowed to stir at room temperature for two hours. It was then heated at 80° C. for 1.5 hours. After cooling, water was added and an aqueous workup was done extracting with ethyl acetate three times. The combined organic layers were washed with water twice, brine, dried over sodium sulfate, filtered and concentrated. The crude product was purified by an SPE tube (5% MeOH/CH$_2$Cl$_2$) to yield the title compound as a white solid. $^1$H NMR (CDCl$_3$) δ (ppm): 8.84 (d, 2H), 8.22 (m, 1H), 8.10 (d oft, 1H), 8.04 (d, 1H), 7.67 (d, 1H), 7.64 (m, 2H), 7.51 (m, 2H), 4.27 (q, 2H), 1.51 (t, 3H).

c) 4-(5-{2-[2-(3-chloro-phenyl)-2H-tetrazol-5-yl]-vinyl}-4-ethyl-4H-[1,2,4]triazol-3-yl)-pyridine The title compound is obtained from 4-(5-{2-[2-(3-chloro-phenyl)-2H-tetrazol-5-yl]-vinyl}-4-ethyl-4H-[1,2,4]triazol-3-yl)-pyridine (1 mmol) by reduction of the olefin.

d) 1-[2-(3-Chloro-phenyl)-2H-tetrazol-5-yl]-2-(4-cyclopropyl-5-pyridin-4-yl-4H-[1,2,4]triazol-3-yl)-ethanol The title compound is obtained from 2-(3-chloro-phenyl)-2H-tetrazole-5-carbaldehyde (1 mmol) by addition of the Grignard reagent formed from magnesium and 4-(5-bromomethyl-4-cyclopropyl-4H-[1,2,4]triazol-3-yl)-pyridine.

e) 2-[2-(3-Chloro-phenyl)-2H-tetrazol-5-yl]-1-(4-cyclopropyl-5-pyridin-4-yl-4H-[1,2,4]triazol-3-yl)-ethanol The title compound is obtained from 4-cyclopropyl-5-pyridin-4-yl-4H-[1,2,4]triazole-3-carbaldehyde (1 mmol) by addition of the Grignard reagent formed from magnesium and 5-bromomethyl-2-(3-chloro-phenyl)-2H-tetrazole.

f) 4-(5-{2-[2-(3-chloro-phenyl)-2H-tetrazol-5-yl]-vinyl}-4-ethyl-4H-[1,2,4]triazol-3-yl)-pyridine The title compound is obtained from 1-[2-(3-Chloro-phenyl)-2H-tetrazol-5-yl]-2-(4-cyclopropyl-5-pyridin-4-yl-4H-[1,2,4]triazol-3-yl)-ethanol (1 mmol) or 2-[2-(3-Chloro-phenyl)-2H-tetrazol-5-yl]-1-(4-cyclopropyl-5-pyridin-4-yl-4H-

[1,2,4]triazol-3-yl)-ethanol (1 mmol) using triethylsilane (mmol) and trifluoroacetic acid (mL) in dichloromethane (mL).

g) 3-(5-{2-[2-(3-Chloro-phenyl)-2H-tetrazol-5-yl]-propyl}-4-methyl-4H-[1,2,4]triazol-3-yl)-pyridine The title compound is obtained analogously to the sequence used for 2-(3-chloro-phenyl)-5-[(triphenyl-$\lambda^5$-phosphanyl)-methyl]-2H-tetrazole hydrobromide (example 30a), 4-(5-{2-[2-(3-chloro-phenyl)-2H-tetrazol-5-yl]-vinyl}-4-ethyl-4H-[1,2,4]triazol-3-yl)-pyridine (example 30b), and 4-(5-{2-[2-(3-chloro-phenyl)-2H-tetrazol-5-yl]-vinyl}-4-ethyl-4H-[1,2,4]triazol-3-yl)-pyridine (example 30c), by starting from 5-(1-bromo-ethyl)-2-(3-chloro-phenyl)-2H-tetrazole as a precursor to the phosphonium salt and 4-methyl-5-pyridin-3-yl-4H-[1,2,4]triazole-3-carbaldehyde as the aldehyde this is reacted with.

h) 2-(3-Chloro-phenyl)-5-{2-[5-(3,5-difluoro-phenyl)-4-methyl-4H-[1,2,4]triazol-3-yl]-1-methyl-ethyl}-2H-tetrazole The title compound is obtained analogously to the sequence used for 2-(3-chloro-phenyl)-5-[(triphenyl-$\lambda^5$-phosphanyl)-methyl]-2H-tetrazole hydrobromide (example 30a), 4-(5-{2-[2-(3-chloro-phenyl)-2H-tetrazol-5-yl]-vinyl}-4-ethyl-4H-[1,2,4]triazol-3-yl)-pyridine (example 30b), and 4-(5-{2-[2-(3-chloro-phenyl)-2H-tetrazol-5-yl]-vinyl}-4-ethyl-4H-[1,2,4]triazol-3-yl)-pyridine (example 30c), by starting from 5-(1-bromo-ethyl)-2-(3-chloro-phenyl)-2H-tetrazole as a precursor to the phosphoniumsalt and 5-(3,5-Difluoro-phenyl)-4-methyl-4H-[1,2,4]triazole-3-carbaldehyde as the aldehyde this is reacted with.

EXAMPLE 31

General Procedure for Tetrahydro-triazolo-pyrimidine synthesis:

Pyridine (~0.5 mL/mmol) was added to acid chloride. The aryl hydrazide (1 equivalent) was then added and the reaction mixture was heated at 130° C. over night. The solution was basified using potassium carbonate and the product was partitioned between ethyl acetate and water, and the organic layer was washed with brine, dried over anhydrous sodium sulfate, filtered and concentrated. An SPE or Flash column was run using a 10-20% MeOH:EtOAc solvent system. The eluting fractions were collected and concentrated. The following aminotriazoles were formed in this way:

a) 3-(3,5-difluorophenyl)-5,6,7,8-tetrahydro[1,2,4]triazolo[4,3-a]pyrimidine;

yield 418 mg (42.8%); white solid; $^1$H NMR CDCl$_3$ δ: 7.26 (d, 2H), 6.9 (t, 1H), 4.1 (t, 2H), 3.52 (t, 2H), 2.13 (m, 2H).

b) 3-(4-methoxyphenyl)-5,6,7,8-tetrahydro[1,2,4]triazolo[4,3-a]pyrimidine;

yield 76.4 mg (8.0%); white solid; $^1$H NMR CDCl$_3$ δ: 7.60 (d, 2H), 7.00 (d, 2H), 5.6 (br, 1H), 4.01 (t, 2H), 3.88 (s, 3H), 3.49 (m, 2H), 2.10 (m, 2H).

c) 3-(2-chloro-6-methoxypyridin-4-yl)-5,6,7,8-tetrahydro[1,2,4]triazolo[4,3-a]pyrimidine;

yield 400 mg (36.5%); white solid; $^1$H NMR CDCl$_3$ δ: 7.34 (s, 1H), 6.93 (s, 1H), 5.60 (br, 1H), 4.112 (t, 2H), 3.98 (s, 3H), 3.52 (m, 2H), 2.15 (m, 2H).

EXAMPLE 32 a) 3-(2-methoxypyridin-4-yl)-5,6,7,8-tetrahydro[1,2,4]triazolo[4,3-a]pyrimidine 3-(2-Chloro-6-methoxy-pyridin-4-yl)-5,6,7,8-tetrahydro-[1,2,4]triazolo[4,3-a]pyrimidine (200 mg) and palladium on carbon (10%, 100 mg) were combined and EtOH (3.2 mL) and triethylamine (0.6 mL) were added. The reaction mixture was stirred under an atmosphere of hydrogen at room temperature overnight, and then filtered through celite. Chromatography (silica, 10% 1M NH$_3$ MeOH in DCM) yielded the product (white solid, 163 mg, 75%). 1H-NMR (CDCl$_3$), δ (ppm): 8.27 (d, 1H), 7.28 (m, 1H), 6.99 (s, 1H), 6.05 (br, 1H), 4.14 (t, 2H), 4.1 (s, 3H), 3.6 (t, 2H), 2.1 (m, 2H)

b) 3-(2-methoxypyridin-4-yl)-6,7,8,9-tetrahydro-5H-[1,2,4]triazolo[4,3-a][1,3]diazepine The title compound was synthesized in quantitative yield in a similar fashion. 1H-NMR (CDCl$_3$), δ (ppm): 8.33 (d, 1H), 7.18 (d, 1H), 7.03 (s, 1H), 4.06 (t, 2H), 3.58 (q, 2H), 2.02 (m, 4H).

EXAMPLE 33

3-[5-(3-chlorophenyl)-2H-tetrazol-2-yl]-N-methylbutanamide a) 2-(3-{[tert-butyl(dimethyl)silyl]oxy}-1-methylpropyl)-5-(3-chlorophenyl)-2H-tetrazole To triphenylphosphine (2.6 g, 10 mmol) in THF (50 mL) at 0° C. under argon, DEAD (1.6 mL, 10 mmol) added during 5 minutes. After stirring for 40 minutes at 0° C. 5-(3-chlorophenyl)-2H-tetrazole (0.90 g, 5 mmol) followed by a solution of 4-{[tert-butyl(dimethyl)silyl]oxy}butan-2-ol (1.53 g, 7.5 mmol) (Tett. 2003, 59, 4739-4748) in THF (5 mL) was added. Stirring at 0° C. for 10 minutes was followed by 21 h at r.t. The mixture was concentrated and purified by flash column chromatography (SiO$_2$, Heptane-EtOAc 7:1) to give 1.8 g (98%) of the title compound.

1H NMR: −0.01 (s, 6H), 0.87 (s, 9H), 1.67 (d, 3H), 2.11 (m, 1H), 2.35 (m, 1H), 3.46 (m, 1H), 3.65 (m, 1H), 5.25 (m, 1H), 7.41 (m, 2H), 8.04 (m, 1H), 8.15 (m, 1H)

b) 3-[5-(3-chlorophenyl)-2H-tetrazol-2-yl]butan-1-ol

TBAF was added to a solution of 2-(3-{[tert-butyl(dimethyl)silyl]oxy}-1-methylpropyl)-5-(3-chlorophenyl)-2H-tetrazole in THF (25 mL). The mixture was concentrated after 4 h and the crude was purified by flash column chromatography (SiO$_2$, Heptane-EtOAc 1:1) to give 0.90 g (91%) of the title compound.

$^1$H NMR: 1.72 (d, 3H), 1.97 (t, 1H), 2.19 (m, 1H), 2.35 (m, 1H), 3.50 (m, 1H), 3.70 (m, 1H), 5.29 (m, 1H), 7.43 (m, 2H), 8.04 (m, 1H), 8.14 (s, 1H)

c) 3-[5-(3-chlorophenyl)-2H-tetrazol-2-yl]butanoic acid

A mixture of CrO$_3$ (0.46 g, 4.63 mmol), H$_2$O (2.5 mL) and concentrated H$_2$SO$_4$ (0.46 mL) was added to a solution of 3-[5-(3-chlorophenyl)-2H-tetrazol-2-yl]butan-1-ol (0.9 g, 3.6 mmol) in acetone (30 mL) at 0° C. The reaction was stirred at r.t. for 1.5 h. 2-Propanol was added and the mixture was concentrated. Sat. NaCl (25 mL) and EtOAc (50 mL) were added to the residue and the mixture was extracted. The water phase was re-extracted with EtOAc (50 mL) and the combined organic phases were dried (MgSO$_4$) and concentrated to give 0.95 g (100%) of the title compound.

$^1$H NMR (MeOH): 1.60 (d, 3H), 2.94 (dd, 1H), 3.16 (dd, 1H), 5.34 (m, 1H), 7.39 (m, 2H), 7.91 (m, 1H), 7.97 (m, 1H);

d) 3-[5-(3-chlorophenyl)-2H-tetrazol-2-yl]-N-methylbutanamide

Oxalylchloride (2 mL, 3.9 mmol) was added during 5 minutes to 3-[5-(3-chlorophenyl)-2H-tetrazol-2-yl]butanoic acid in DCM (40 mL) and DMF (5 drops) under argon. The mixture was stirred at r.t. for 3 h and then was MeNH$_2$ (2M in THF, 3.6 mL, 7.2 mmol) added and the resulting mixture was stirred o.n. Saturated NaHCO$_3$ (75 mL) was added and the mixture was extracted with CHCl$_3$ (3×100 mL). The combined organic phases were dried (MgSO$_4$) and concentrated. The crude was purified by flash column chromatography (SiO$_2$, Heptane-EtOAc 1:2) to give 0.74 g (74%) of the title compound.

$^1$H NMR: 1.71 (d, 3H), 2.78 (d, 3H), 2.82 (dd, 1H), 5.53 (q, 1H), 5.87 (br. s., 1H), 7.42 (m, 2H), 8.01 (m, 1H), 8.12 (s, 1H);

EXAMPLE 34

3-[4-methyl-5-(methylsulfonyl)-4H-1,2,4-triazol-3-yl pyridine a) 4-methyl-5-pyridin-3-yl-2,4-dihydro-3H-1,2,4-triazole-3-thione

Nicotinohydrazide (10 g, 73 mmol) and methyl isothiocyanate (5.6 g, 76 mmol) were mixed in 2-propanol (150 ml) and heated to 70° C. o.n. The reaction was cooled to r.t. and evaporated to dryness. H$_2$O (180 mL) and NaHCO$_3$ (12.8 g, 152 mmol) were added to the residue and the mixture was refluxed o.n. The reaction mixture was cooled to r.t., acidified with concentrated HCl and the title compound, 13.1 g (93%), was collected by filtration. LC-MS (M$^+$+1): 193 b) 3-[4-methyl-5-(methylthio)-4H-1,2,4-triazol-3-yl]pyridine

MeI (2 mL, 32 mmol) in EtOH (10 mL) was added to a mixture of 4-methyl-5-pyridin-3-yl-2,4-dihydro-3H-1,2,4-triazole-3-thione in 1 M NaOH (70 mL, 70 mmol). After 1 h stirring at r.t., DCM was added and the layers were separated. The water phase was washed with DCM and the combined organic phases were dried and concentrated to give 6.5 g (98%) of the title compound. $^1$H NMR: 2.76 (s, 3H) 3.59 (s, 3H) 7.43 (m, 1H) 7.99 (m, 1H) 8.71 (m, 1H) 8.86 (m, 1H)

c) 3-[4-methyl-5-(methylsulfonyl)-4H-1,2,4-triazol-3-yl]pyridine

KMnO$_4$ (5 g, 32 mmol) was added to a solution of 3-[4-methyl-5-(methylthio)-4H-1,2,4-triazol-3-yl]pyridine (6.0 g, 29 mmol) in H$_2$O (40 mL) and acetic acid (100 mL). After 1 h stirring at r.t. the reaction was basified with 4M NaOH. CHCl$_3$ was added and the mixture was filtrated through celite. The layers were separated and the water phase was washed with CHCl$_3$. The combined organic phase was dried and concentrated to give 3.67 g (53%) of the title compound. $^1$H NMR: 3.59 (s, 3H) 3.99 (s, 3H) 7.52 (m, 1H) 8.02 (dt, 1H) 8.83 (dd, 1H) 8.91 (m, 1H)

EXAMPLE 35

3-(3,5-difluorophenyl)-4-methyl-5-(methylsulfonyl)-4H-1,2,4-triazole a) 5-(3,5-difluorophenyl)-4-methyl-2,4-dihydro-3H-1,2,4-triazole-3-thione 3,5-difluorobenzohydrazide (5 g, 29 mol) and methyl isothiocyanate (2.1 g, 29 mmol) were mixed in 2-propanol (100 ml) and heated to 70° C. o.n. The reaction was cooled to r.t. and the formed precipitate was filtered off. H$_2$O (100 mL) and NaHCO$_3$ (4 g, 48 mmol) were added to the solid and the mixture was heated to 70° C. for 2 h. The reaction mixture was cooled to r.t., acidified with concentrated HCl and the title compound, 6.4 g (97%), was collected by filtration. LC-MS (M$^+$+1): 228 b) 3-(3,5-difluorophenyl)-4-methyl-5-(methylthio)-4H-1,2,4-triazole

MeI (1.4 mL, 22.4 mmol) was added to a mixture of 5-(3,5-difluorophenyl)-4-methyl-2,4-dihydro-3H-1,2,4-triazole-3-thione (5 g, 22 mmol) in acetone (80 mL). NaOH (0.9 g, 22 mmol) in H$_2$O (20 mL) was added and the reaction was stirred for 3 h at r.t. The formed precipitate was filtered off and the solution is evaporated to half volume and the formed precipitate was filtered off and combined with the first filtrate to give 4.92 g (93%) of the title compound.

$^1$H NMR: 2.75 (s, 3H), 3.79 (s, 3H), 6.80 (m, 1H), 7.58 (m, 2H)

c) 3-(3,5-difluorophenyl)-4-methyl-5-(methylsulfonyl)-4H-1,2,4-triazole m-CPBA (10 g, 33-50 mmol, 57-86% pure) was added to a solution of 3-(3,5-difluorophenyl)-4-methyl-5-(methylthio)-4H-1,2,4-triazole (4.9 g, 20.3 mmol) in DCM (60 mL) and the reaction was stirred o.n. 2M NaOH (50 mL) was added and the mixture was extracted. The water phase was re-extracted with EtOAc (2×) and the combined organic phases were dried (MgSO4) and evaporated to give 5.4 g (98%) of the title compound.

$^1$H NMR: 3.48 (s, 3H), 4.23 (s, 3H), 6.87 (m, 1H), 7.59 (m, 2H)

EXAMPLE 36

(1R)-1-[2-(3-chlorophenyl)-2H-tetrazol-5-yl]ethyl acetate 2.22 g (9.93 mmol) racemic 1-[2-(3-chlorophenyl)-2H-tetrazol-5-yl]ethanol and 0.40 g Novozyme 435® are taken up under Ar in toluene (120 mL). After addition of 109 μL (1.18 mmol) vinyl acetate the reaction was run at r.t. o.n., followed by addition of 0.12 g Novozyme 435® and 218 μL (2.36 mmol) vinylacetate and increasing the temperature to 30° C. o.n. Further addition of 2 g Novozyme 435® and 150 μL (1.63 mmol) vinylacetate gave after 7 h ca 41% conversion of starting material. To enhance yield, the reaction was filtered over celite washed with DCM, evaporated to dryness, then taken up in toluene (250 mL). After addition of 0.3 g Novozyme 435® and 200 μL (2.17 mmol) vinylacetate under Ar, 48% conversion after 4 h at r.t. were achieved. Filtration over celite and washing with DCM gave crude which was purified over silica using DCM neat, followed by EA/Hep=1/

2, yielding 1.26 g (48%) of the title compound. $^1$H NMR: 8.15 (m, 1H), 8.03 (m, 1H), 7.48 (m, 2H), 6.27 (q, 1H), 2.14 (s, 3H), 1.77 (d, 3H).

EXAMPLE 37

(1R)-1-[2-(3-chlorophenyl)-2H-tetrazol-5-yl]ethanol 1.25 g (4.68 mmol) (1R)-1-[2-(3-chlorophenyl)-2H-tetrazol-5-yl]ethyl acetate and 0.48 g (11.4 mmol) lithium hydroxide monohydrate were mixed with 3:1 THF/Water (28 mL) and stirred for 20 h. After acidification with aq. HCl, followed by reducing the volume of the mixture in vacuo, followed by dilution with brine and extraction with DCM. 5.8 g (97%) of the title compound was obtained after evaporation & coevaporation with toluene, followed by drying. $^1$H NMR: 8.15 (m, 1H), 8.03 (m, 1H), 7.48 (m, 2H), 6.27 (q, 1H), 2.14 (s, 3H), 1.77 (d, 3H).

EXAMPLE 38

(1S)-1-[2-(3-chlorophenyl)-2H-tetrazol-5-yl]ethanol

The title compound was isolated from the reaction as described for the synthesis of (1R)-1-[2-(3-chlorophenyl)-2H-tetrazol-5-yl]ethyl acetate. Isolation took place during heptane/ethyl acetate elution of the column chromatography, yielding 1.09 g (49%) of the title compound. $^1$H NMR: 8.16 (m, 1H), 8.04 (m, 1H), 7.48 (m, 2H), 5.28 (q, 1H), 1.74 (d, 3H), 1.54 (s, 1H)

EXAMPLE 39

General Procedure: Nucleophilic Displacement with 2-Chloro-3-Nitro-Pyridine

Piperazine (2-5 mmol) and 2-chloro-3-nitro-pyridine (1 mmol) were dissolved in DMF or acetonitrile (2-3 mL) and stirred for 5 min at room temperature. A slight exothermic was observed shortly after addition of the solvent. When TLC analysis showed that the reaction was complete, the mixture was diluted with dichloromethane, and washed with water. The organic layer was dried, filtered and concentrated, then chromatographed in 10% methanol in dichloromethane to yield the desired product.

In this manner the following compounds were synthesized:

a) (3S)-3-methyl-1-(3-nitropyridin-2-yl)piperazine;

yield 92%; $^1$H NMR 300 MHz, CDCl$_3$) δ: 1.11 (d, J=6.3 Hz, 3H); 2.74 (dd, J=12.8, 10.4 Hz, 1H); 2.99 (m, 4H); 3.72 (m, 2H); 6.74 (dd, J=8.1, 4.5 Hz, 1H); 8.14 (dd, J=8.1, 1.8 Hz, 1H); 8.34 (dd, J=4.5, 1.8 Hz, 1H).

b) (3R)-3-methyl-1-(3-nitropyridin-2-yl)piperazine;

yield 100%; $^1$H NMR 300 MHz, CDCl$_3$) δ: 1.11 (d, J=6.3 Hz, 3H); 2.74 (dd, J=12.8, 10.4 Hz, 1H); 2.99 (m, 4H); 3.72 (m, 2H); 6.74 (dd, J=8.1, 4.5 Hz, 1H); 8.14 (dd, J=8.1, 1.8 Hz, 1H); 8.34 (dd, J=4.5, 1.8 Hz, 1H).

c) 1-(3-nitropyridin-2-yl)piperazine;

yield 63%; $^1$H NMR 300 MHz, CDCl$_3$) δ: 3.00 (m, 4H); 3.45 (m, 4H); 6.75 (dd, J=8.1, 4.5 Hz, 1H); 8.14 (dd, J=8.1, 1.8 Hz, 1H); 8.34 (dd, J=4.5, 1.8 Hz, 1H).

EXAMPLE 40

General Procedure: Nucleophilic Displacement with 2-Chloro-3-Cyano-Pyrazine

Piperazine (1.5 mmol) and 2-chloro-3-nitro-pyridine (1 mmol) were dissolved in acetonitrile (3 mL) and stirred for 30 min at 85° C. The reaction mixture was diluted with dichloromethane and washed with water. The organic layer was isolated, washed with brine, dried over anhydrous Na$_2$SO$_4$ and concentrated in vacuo. The product was purified (SPE column chromatography, silica gel, 0-10% methanol in ethyl acetate).

In this manner the following compounds were synthesized:
a) 3-[(3S)-3-methylpiperazin-1-yl]pyrazine-2-carbonitrile;
yield 127.1 mg, 35%, orange oil; $^1$H NMR 300 MHz, CDCl$_3$) δ: 8.26 (m, 1H); 8.00 (m, 1H); 4.40 (m, 2H); 3.05 (m, 4H); 2.77 (m, 1H); 1.74 (m, 1H); 1.16 (d, 3H).
b) 3-[(3R)-3-methylpiperazin-1-yl]pyrazine-2-carbonitrile;
yield 195.3 mg, 54%, orange oil; $^1$H NMR 300 MHz, CDCl$_3$) δ: 8.26 (m, 1H); 8.00 (m, 1H); 4.40 (m, 2H); 3.05 (m, 4H); 2.77 (m, 1H); 1.74 (m, 1H); 1.16 (d, 3H).

EXAMPLE 41

General Procedure: Palladium Catalyzed Coupling to Heteroaryl Chloride

2-Chloro-nicotinonitrile (1.0 mmol), (S)-2-methyl piperazine (1.5 mmol), sodium tert-butoxide (1.5 mmol) and tris(dibenzylideneacetone)-dipalladium(0) (0.04 mmol) were added to a screw cap vial. 2,8,9-Triisobutyl-2,5,8,9-tetraaza-1-phospha-bicyclo[3.3.3]undecane (0.08 mmol) was dissolved in toluene (5 mL) and this solution was added to the other reagents. The reaction mixture was stirred at 100° C. overnight. The solution was diluted with dichloromethane and washed with water. The organic phase was dried, filtered and concentrated, then purified by flash chromatography in 10% (2M ammonia in methanol) in dichloromethane to yield the desired product.

In this manner the following compounds were synthesized:
a) 2-[(3S)-3-methylpiperazin-1-yl]nicotinonitrile;
yield 64%; $^1$H NMR 300 MHz, CDCl$_3$) δ: 1.03 (d, J=6.3 Hz, 3H); 1.73 (s, broad, 1H); 2.59 (dd, J=12.9, 10.2 Hz, 1H); 2.94 (m, 4H); 4.16 (m, 2H); 6.64 (dd, J=7.8, 4.8 Hz, 1H); 7.66 (dd, J=7.8, 2.1 Hz, 1H); 8.23 (dd, J=4.8, 2.1 Hz, 1H).
b) 2-[(3R)-3-methylpiperazin-1-yl]nicotinonitrile;
yield 46%; $^1$H NMR 300 MHz, CDCl$_3$) δ: 1.03 (d, J=6.3 Hz, 3H); 1.73 (s, broad, 1H); 2.59 (dd, J=12.9, 10.2 Hz, 1H); 2.94 (m, 4H); 4.16 (m, 2H); 6.64 (dd, J=7.8, 4.8 Hz, 1H); 7.66 (dd, J=7.8, 2.1 Hz, 1H); 8.23 (dd, J=4.8, 2.1 Hz, 1H).

EXAMPLE 42

4-(5-{2-[5-(3-chlorophenyl)-2H-tetrazol-2-yl]propyl}-4-methyl-4H-1,2,4-triazol-3-yl)pyridine Oxalylchloride (2M in DCM, 0.28 mL, 0.55 mmol) was dropwise added during 5 minutes to a solution of 3-[5-(3-chlorophenyl)-2H-tetrazol-2-yl]-N-methylbutanamide (140 mg, 0.5 mmol) and 2,6-lutidine (0.12 mL, 1 mmol) in DCM (5 mL) at 0° C. The mixture was stirred at 0° C. for 1 h and isonicotinic acid hydrazide (103 mg, 0.75 mmol) was added. DCM was evaporated after 4 h stirring at r.t. Sat. aq. NaHCO$_3$ (10 mL) was added to the residue and the mixture was refluxed for 16 h. The reaction was allowed to attain r.t., followed by extracted with CHCl$_3$ (3×20 mL). The combined organic phases were dried (MgSO$_4$), concentrated and purified by prep HPLC to yield the title compound (3 mg, 2%).
$^1$H NMR: 1.91 (d, 3H), 3.51 (m, 1H), 3.65 (m, 4H), 5.74 (q, 1H), 7.43 (m, 2H), 7.62 (d, 2H), 8.01 (dt, 1H), 8.11 (m, 1H), 8.78 (br. s., 2H) MS (ESI) m/z 381 (M+1).

EXAMPLE 43

4-(5-[{(R)-1-[2-(3-Chloro-phenyl)-2H-tetrazol-5-yl]-ethoxy}-4-methyl-4H-[1,2,4]triazol-3-yl)-pyridine (1R)-1-[2-(3-chlorophenyl)-2H-tetrazol-5-yl]ethanol (0.31 g, 1.38 mmol), 4-(5-Methanesulfonyl-4-methyl-4H-[1,2,4]triazol-3-yl)-pyridine (0.32 g, 1.34 mmol), cesium carbonate (0.58 g, 1.78 mmol) and DMF (4 mL) are mixed and stirred at 60° C. o.n. under Argon. Partitioning between water and DCM and reextraction of aq. layer with DCM, combining the organic layers, gave after evaporation in vacuo, followed by flash chromatography (heptane/ethyl acetate/methanol=10/10/1 to 5/5/1) & drying the title compound (490 mg, 96%). $^1$H-NMR: 8.66 (m, 2H), 8.07 (t, 1H), 7.96 (m, 1H), 7.55 (m, 2H), 7.40 (m, 2H), 6.51 (q, 1H), 3.57 (s, 3H), 1.95 (d, 3H).

In a similar manner, the following compounds were prepared:

b) 4-(5-{(S)-1-[2-(3-Chloro-phenyl)-2H-tetrazol-5-yl]-ethoxy}-4-methyl-4H-[1,2,4]triazol-3-yl)-pyridine;

yield 1.55 g, 91%; $^1$H NMR CDCl$_3$ δ: 8.66 (m, 2H), 8.07 (t, 1H), 7.96 (m, 1H), 7.55 (m, 2H), 7.40 (m, 2H), 6.51 (q, 1H), 3.57 (s, 3H), 1.95 (d, 3H)

c) 2-(3-Chloro-phenyl)-5-{(R)-1-[5-(3,5-difluoro-phenyl)-4-methyl-4H-[1,2,4]triazol-3-yloxy]-ethyl}-2H-tetrazole;

yield 77 mg, 77%; $^1$H NMR CDCl$_3$ δ: 8.16 (m, 1H), 8.04 (dt, 1H), 7.48 (m, 2H), 7.21 (m, 2H), 6.92 (m, 1H), 6.57 (q, 1H), 3.56 (s, 3H), 2.01 (d, 3H)

d) 3-(5-{(R)-1-[2-(3-Chloro-phenyl)-2H-tetrazol-5-yl]-ethoxy}-4-methyl-4H-[1,2,4]triazol-3-yl)-pyridine;

yield 72 mg, 55%; $^1$H NMR CDCl$_3$ δ: 8.88 (m, 1H), 8.71 (dd, 1H), 8.16 (m, 1H), 8.03 (m, 2H), 7.48 (m, 2H), 7.43 (m, 1H), 6.58 (q, 1H), 3.57 (s, 3H), 2.02 (d, 3H)

EXAMPLE 44

1-[2-(3-chloro-phenyl)-2H-tetrazol-5-yl-ethanol

Ozone was bubbled through a solution of 2-(3-chlorophenyl)-5-[1-methyl-2-phenylvinyl]-2H-tetrazole (2.73 g, 9.2 mmol) in methanol (75 mL) and dichloromethane (75 mL) at −78° C. When the color lightened and the starting material had disappeared by TLC, oxygen was bubbled through the mixture for approximately 2-3 minutes. Sodium borohydride (635 mg, 16.8 mmol) was added. The reaction was allowed to warm to room temperature, stirred for 30 minutes and quenched with water (5 mL) and saturated ammonium chloride (5 mL). After removal of the solvent in vacuo, the product was partitioned between dichloromethane and water, dried over sodium sulfate, and the solvent was removed in vacuo. Flash chromatography (15-35% ethyl acetate in hexane) yielded the title compound as a yellow solid (1.795 g, 87%).
$^1$H NMR (CDCl$_3$) δ (ppm): 8.19 (m, 1H), 8.06 (m, 1H), 7.50 (m, 2H), 5.3 (m, 1H), 2.54 (m, 1H), 1.78 (d, 3H).

Pharmacology

The pharmacological properties of the compounds of the invention can be analyzed using standard assays for functional activity. Examples of glutamate receptor assays are well known in the art as described in for example Aramori et al., Neuron 8:757 (1992), Tanabe et al., Neuron 8:169 (1992), Miller et al., J. Neuroscience 15: 6103 (1995), Balazs, et al., J. Neurochemistry 69:151 (1997). The methodology described in these publications is incorporated herein by reference. Conveniently, the compounds of the invention can be studied by means of an assay that measures the mobilization of intracellular calcium, [Ca$^{2+}$]$_i$ in cells expressing mGluR5.

For FLIPR analysis, cells expressing human mGluR5d as described in WO97/05252 were seeded on collagen coated clear bottom 96-well plates with black sides and analysis of [Ca$^{2+}$]$_i$ mobilization was done 24 h after seeding.

FLIPR experiments were done using a laser setting of 0.800 W and a 0.4 second CCD camera shutter speed. Each FLIPR experiment was initiated with 160 µl of buffer present in each well of the cell plate. After each addition of the compound, the fluorescence signal was sampled 50 times at 1 second intervals followed by 3 samples at 5 second intervals. Responses were measured as the peak height of the response within the sample period. EC$_{50}$ and IC$_{50}$ determinations were made from data obtained from 8-point concentration response curves (CRC) performed in duplicate. Agonist CRC were generated by scaling all responses to the maximal response observed for the plate. Antagonist block of the agonist challenge was normalized to the average response of the agonist challenge in 14 control wells on the same plate.

We have validated a secondary functional assay for mGluR5d as described in WO97/05252 based on Inositol Phosphate (IP$_3$) turnover. IP$_3$ accumulation is measured as an index of receptor mediated phospholipase C turnover. GHEK cells stably expressing the human mGluR5d receptors were incubated with [3H] myo-inositol overnight, washed three times in HEPES buffered saline and pre-incubated for 10 min with 10 mM LiCl. Compounds (agonists) were added and incubated for 30 min at 37° C. Antagonist activity was determined by pre-incubating test compounds for 15 min, then incubating in the presence of glutamate (80 µM) or DHPG (30 µM) for 30 min. Reactions were terminated by the addition of perchloric acid (5%). Samples were collected and neutralized, and inositol phosphates were separated using Gravity-Fed Ion-Exchange Columns.

A detailed protocol for testing the compounds of the invention is provided in the assay below.

Assay of Group I Receptor Antagonist Activity

For FLIPR analysis, cells expressing human mGluR5d as described in WO97/05252 were seeded on collagen coated clear bottom 96-well plates with black sides and analysis of [Ca$^{2+}$]$_i$ mobilization was performed 24 h following seeding. Cell cultures in the 96-well plates were loaded with a 4 µM solution of acetoxymethyl ester form of the fluorescent calcium indicator fluo-3 (Molecular Probes, Eugene, Oreg.) in 0.01% pluronic. All assays were performed in a buffer containing 127 mM NaCl, 5 mM KCl, 2 mM MgCl$_2$, 0.7 mM NaH$_2$PO$_4$, 2 mM CaCl$_2$, 0.422 mg/ml NaHCO$_3$, 2.4 mg/ml HEPES, 1.8 mg/ml glucose and 1 mg/ml BSA Fraction IV (pH 7.4).

FLIPR experiments were done using a laser setting of 0.800 W and a 0.4 second CCD camera shutter speed with excitation and emission wavelengths of 488 nm and 562 nm, respectively. Each FLIPR experiment was initiated with 160 µl of buffer present in each well of the cell plate. A 40 µl addition from the antagonist plate was followed by a 50 µL addition from the agonist plate. After each addition the fluorescence signal was sampled 50 times at 1 second intervals followed by 3 samples at 5 second intervals. Responses were measured as the peak height of the response within the sample period.

$EC_{50}/IC_{50}$ determinations were made from data obtained from 8 points concentration response curves (CRC) performed in duplicate. Agonist CRC were generated by scaling all responses to the maximal response observed for the plate. Antagonist block of the agonist challenge was normalized to the average response of the agonist challenge in 14 control wells on the same plate.

Measurement of Inositol Phosphate Turnover in Intact Whole Cells

GHEK stably expressing the human mGluR5d receptor were seeded onto 24 well poly-L-lysine coated plates at $40 \times 10^4$ cells/well in media containing 1 µCi/well [3H] myo-inositol. Cells were incubated overnight (16 h), then washed three times and incubated for 1 h at 37° C. in HEPES buffered saline (146 mM NaCl, 4.2 mM KCl, 0.5 mM $MgCl_2$, 0.1% glucose, 20 mM HEPES, pH 7.4) supplemented with 1 unit/ml glutamate pyruvate transaminase and 2 mM pyruvate. Cells were washed once in HEPES buffered saline and pre-incubated for 10 min in HEPES buffered saline containing 10 mM LiCl. Compounds (agonists) were added and incubated at 37° C. for 30 min. Antagonist activity was determined by pre-incubating test compounds for 15 min, then incubating in the presence of glutamate (80 µM) or DHPG (30 µM) for 30 min. The reaction was terminated by the addition of 0.5 ml perchloric acid (5%) on ice, with incubation at 4° C. for at least 30 min. Samples were collected in 15 ml Falcon tubes and inositol phosphates were separated using Dowex columns, as described below.

Assay for Inositol Phosphates Using Gravity-Fed Ion-Exchange Columns

Preparation of Ion-Exchange Columns

Ion-exchange resin (Dowex AG1-X8 formate form, 200-400 mesh, BIORAD) was washed three times with distilled water and stored at 4° C. 1.6 ml resin was added to each column, and washed with 3 ml 2.5 mM HEPES, 0.5 mM EDTA, pH 7.4.

a) Sample Treatment

Samples were collected in 15 ml Falcon tubes and neutralized with 0.375 M HEPES, 0.75 M KOH. 4 ml of HEPES/EDTA (2.5/0.5 mM, pH 7.4) were added to precipitate the potassium perchlorate. Supernatant was added to the prepared Dowex columns.

b) Inositol Phosphate Separation

Elute glycero phosphatidyl inositols with 8 ml 30 mM ammonium formate. Elute total inositol phosphates with 8 ml 700 mM ammonium formate/100 mM formic acid and collect eluate in scintillation vials. Count eluate mixed with 8 ml scintillant.

One aspect of the invention relates to a method for inhibiting activation of mGluR 5, comprising treating a cell containing said receptor with an effective amount of the compound of formula I.

Screening for Compounds Active Against tlesr

Adult Labrador retrievers of both genders, trained to stand in a Pavlov sling, are used. Mucosa-to-skin esophagostomies are formed and the dogs are allowed to recover completely before any experiments are done.

Motility Measurement

In brief, after fasting for approximately 17 h with free supply of water, a multilumen sleeve/sidehole assembly (Dentsleeve, Adelaide, South Australia) is introduced through the esophagostomy to measure gastric, lower esophageal sphincter (LES) and esophageal pressures. The assembly is perfused with water using a low-compliance manometric perfusion pump (Dentsleeve, Adelaide, South Australia). An air-perfused tube is passed in the oral direction to measure swallows, and an antimony electrode monitored pH, 3 cm above the LES. All signals are amplified and acquired on a personal computer at 10 Hz.

When a baseline measurement free from fasting gastric/LES phase III motor activity has been obtained, placebo (0.9% NaCl) or test compound is administered intravenously (i.v., 0.5 ml/kg) in a foreleg vein. Ten min after i.v. administration, a nutrient meal (10% peptone, 5% D-glucose, 5% Intralipid, pH 3.0) is infused into the stomach through the central lumen of the assembly at 100 ml/min to a final volume of 30 ml/kg. The infusion of the nutrient meal is followed by air infusion at a rate of 500 ml/min until an intragastric pressure of $10 \pm 1$ mmHg is obtained. The pressure is then maintained at this level throughout the experiment using the infusion pump for further air infusion or for venting air from the stomach. The experimental time from start of nutrient infusion to end of air insufflation is 45 min. The procedure has been validated as a reliable means of triggering TLESRs.

TLESRs is defined as a decrease in lower esophageal sphincter pressure (with reference to intragastric pressure) at a rate of >1 mmHg/s. The relaxation should not be preceded by a pharyngeal signal <2 s before its onset in which case the relaxation is classified as swallow-induced. The pressure difference between the LES and the stomach should be less than 2 mmHg, and the duration of the complete relaxation longer than 1 s.

| Abbreviations | |
|---|---|
| atm | atmosphere |
| Aq | aqueous |
| BOC | tert-butoxycarbonyl |
| BSA | Bovine Serum Albumin |
| nBu | normal butyl |
| CCD | Charge Coupled Device |
| MCPBA | meta-chloroperoxybenzoic acid |
| CRC | Concentration Response Curve |
| DCM | dichloromethane |
| DEAD | diethyl azodicarboxylate |
| DHPG | 3,5-dihydroxyphenylglycine |
| DMAP | 4(N,N-dimethylamino)pyridine |
| DMF | N,N-dimethylformamide |
| EA | ethyl acetate |
| EDC | 1-Ethyl-3-(3-dimethylaminopropyl)carbodiimide |
| EDTA | Ethylene Diamine Tetraacetic Acid |
| FLIPR | Fluorometric Imaging Plate reader |
| GHEK | GLAST-containing Human Embryonic Kidney |
| GLAST | glutamate/aspartate transporter |
| h. | hour |
| HBTU | O-benzotriazol-1-yl-N,N,N',N'-tetramethyluronium hexafluorophosphate |
| HEPES | 4-(2-hydroxyethyl)-1-piperazineethanesulfonic acid (buffer) |
| hep | heptane |
| hex | hexane(s) |
| $IP_3$ | inositol triphosphate |
| LAH | lithium aluminumhydride |
| Novozyme 435 ® | Polymer supported Candida Antartica Lipase (Novozymes, Bagsvaerd, Denmark) |

-continued

| Abbreviations | |
|---|---|
| o.n. | overnight |
| PCC | Pyridinium chlorochromate |
| PPTS | pyridinium p-toluenesulfonate |
| prep | preparative |
| r.t. | room temperature |
| sat. | saturated |
| TBAF | tetrabutylammonium fluoride |
| THF | tetrahydrofuran |
| pTsOH | p-toluenesulfonic acid |

RESULTS

Typical $IC_{50}$ values as measured in the assays described above are 10 µM or less. In one aspect of the invention the $IC_{50}$ is below 2 µM. In another aspect of the invention the $IC_{50}$ is below 0.2 µM. In a further aspect of the invention the $IC_{50}$ is below 0.05 µM.

Examples of $IC_{50}$ values for individual compounds is given below:

| Compound | FLIPR $IC_{50}$ |
|---|---|
| 4-[5-({1-[2-(5-chloro-2-fluorophenyl)-2H-tetrazol-5-yl]ethyl}thio)-4-methyl-4H-1,2,4-triazol-3-yl]pyridine | 55 nM |
| Ethyl 4-{1-[2-(3-chlorophenyl)-2H-tetrazol-5-yl]ethyl}piperazine-1-carboxylate | 132 nM |

The invention claimed is:

1. A compound according to formula I $$(R^1)_m-P-\underset{N=N}{\overset{N=N}{\underset{X_3}{\bigvee}}}X_4-X^1-X^2-Q-(R^2)_p$$

wherein
$X_3$ and $X_4$ are selected from N and C, such that when $X_3$ is N, $X_4$ is C and when $X_3$ is C, $X_4$ is N;
P is selected from aryl and heteroaryl;
if m=1 then $R^1$ is attached to P via a carbon atom on ring P at the meta-position of the ring P relative to the attachment point of P at $X^3$, and if m=2 then $R^1$ is attached to P via carbon atoms on ring P at the 2-, and 5-positions of the ring P;
$R^1$ is selected from the group consisting of hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, CHO, $(CO)R^5$, $O(CO)R^5$, $O(CO)OR^5$, $O(CNR^5)OR^5$, $C_{1-6}$alkyl$OR^5$, $OC_{2-6}$alkyl$OR^5$, $C_{1-6}$alkyl$(CO)R^5$, $OC_{1-6}$alkyl$(CO)R^5$, $C_{0-6}$alkyl$CO_2R^5$, $OC_{1-6}$alkyl$CO_2R^5$, $C_{0-6}$alkylcyano, $OC_{2-6}$alkylcyano, $C_{0-6}$alkyl$NR^5R^6$, $OC_{2-6}$alkyl$NR^5R^6$, $C_{1-6}$alkyl$(CO)NR^5R^6$, $OC_{1-6}$alkyl$(CO)NR^5R^6$, $C_{0-6}$alkyl$NR^5(CO)R^6$, $OC_{2-6}$alkyl$NR^5(CO)R^6$, $C_{0-6}$alkyl$NR^5(CO)NR^5R^6$, $C_{0-6}$alkyl$SR^5$, $OC_{2-6}$alkyl$SR^5$, $C_{0-6}$alkyl$(SO)R^5$, $OC_{2-6}$alkyl$(SO)R^5$, $C_{0-6}$alkyl$SO_2R^5$, $OC_{2-6}$alkyl$SO_2R^5$, $C_{0-6}$alkyl$(SO_2)NR^5R^6$, $OC_{2-6}$alkyl$(SO_2)NR^5R^6$, $C_{0-6}$alkyl$NR^5(SO_2)R^6$, $OC_{2-6}$alkyl$NR^5(SO_2)R^6$, $C_{0-6}$alkyl$NR^5(SO_2)NR^5R^6$, $OC_{2-6}$alkyl$NR^5(SO_2)NR^5R^6$, $(CO)NR^5R^6$, $O(CO)NR^5R^6$, $NR^5OR^6$, $C_{0-6}$alkyl$NR^5(CO)OR^6$, $OC_{2-6}$alkyl$NR^5(CO)OR^6$, $SO_3R^5$ and a 5- or 6-membered ring containing one or more atoms independently selected from the group consisting of C, N, O and S;
$X^1$ is selected from the group consisting of $C_{2-3}$alkyl, $C_{2-3}$alkenyl, $NR^3$, O, S, $CR^3R^4$, SO, $SO_2$
$X^2$ is selected from the group consisting of a bond, $CR^3R^4$, O, S, $NR^3$, SO, $SO_2$
$R^3$ and $R^4$ are independently selected from a group consisting of hydrogen, hydroxy, $C_{1-6}$alkyl, $C_{0-6}$alkylcyano, oxo, $=NR^5$, $=NOR^5$, $C_{1-4}$alkylhalo, halo, $C_{1-4}$alkyl$C_{3-7}$cycloalkyl, $C_{3-7}$cycloalkyl, $O(CO)C_{1-4}$alkyl, $(CO)C_{1-4}$alkyl, $C_{1-4}$alkyl$(SO)C_{0-4}$alkyl, $C_{1-4}$alkyl$(SO_2)C_{0-4}$alkyl, $(SO)C_{0-4}$alkyl, $(SO_2)C_{0-4}$alkyl, $OC_{1-4}$alkyl, $C_{1-4}$alkyl$OR^5$ and $C_{0-4}$alkyl$NR^5R^6$;
Q is either selected from triazole, piperazine, and imidazole, or else, Q is any other 4-, 5-, 6-, or 7-membered heterocyclic ring containing one or more heteroatoms selected from N, O and S and is fused to a triazole ring;
$R^2$ is selected from the group consisting of hydroxy, $C_{0-6}$alkylcyano, $=NR^5$, $=O$, $=NOR^5$, $C_{1-4}$alkylhalo, halo, $C_{1-6}$alkyl, $C_{3-6}$cycloalky, $C_{0-6}$alkylaryl, $C_{0-6}$alkylheteroaryl, $C_{0-6}$alkycycloalkyl, $C_{0-6}$alkylheterocycloalkyl, $OC_{1-4}$alkyl, $OC_{0-6}$alkylaryl, $O(CO)C_{1-4}$alkyl, $(CO)OC_{1-4}$alkyl, $C_{0-4}$alkyl$(S)C_{0-4}$alkyl, $C_{1-4}$alkyl$(SO)C_{0-4}$alkyl, $C_{1-4}$alkyl$(SO_2)C_{0-4}$alkyl, $(SO)C_{0-4}$alkyl, $(SO_2)C_{0-4}$alkyl, $C_{1-4}$alkyl$OR^5$, $C_{0-4}$alkyl$NR^5R^6$ and a 5- or 6-membered ring containing one or more atoms independently selected from C, N, O and S, which ring may optionally be fused with a 5- or 6-membered ring containing one or more atoms independently selected from the group consisting of C, N and O and wherein said ring and said fused ring may be substituted by one or more A; and any $C_{1-6}$alkyl, aryl, or heteroaryl defined under $R^1$, $R^2$ and $R^3$ may be substituted by one or more A; and A is selected from the group consisting of hydrogen, hydroxy, halo, nitro, oxo, $C_{0-6}$alkylcyano, $C_{0-4}$alkyl$C_{3-6}$cycloalky, $C_{1-6}$alkyl, $OC_{1-6}$alkyl, $C_{1-6}$alkylhalo, $OC_{1-6}$alkylhalo, $C_{2-6}$alkenyl, $C_{0-3}$alkylaryl, $C_{0-6}$alkyl$OR^5$, $OC_{2-6}$alkyl$OR^5$, $C_{1-6}$alkyl$SR^5$, $OC_{2-6}$alkyl$SR^5$, $(CO)R^5$, $O(CO)R^5$, $OC_{2-6}$alkylcyano, $OC_{1-6}$alkyl$CO_2R^5$, $O(CO)OR^5$, $OC_{1-6}$alkyl$(CO)R^5$, $C_{1-6}$alkyl$(CO)R^5$, $NR^5OR^6$, $C_{0-6}NR^5R^6$, $OC_{2-6}$alkyl$NR^5R^6$, $C_{0-6}$alkyl$(CO)NR^5R^6$, $OC_{1-6}$alkyl$(CO)NR^5R^6$, $OC_{2-6}$alkyl$NR^5(CO)R^6$, $C_{0-6}$alkyl$NR^5(CO)R^6$, $C_{0-6}$alkyl$NR^5(CO)NR^5R^6$, $O(CO)NR^5R^6$, $C_{0-6}$alkyl$(SO_2)NR^5R^6$, $OC_{2-6}$alkyl$(SO_2)NR^5R^6$, $C_{0-6}$alkyl$NR^5(SO_2)R^6$, $OC_{2-6}$alkyl$NR^5(SO_2)R^6$; $SO_3R^5$, $C_{1-6}$alkyl$NR^5(SO_2)NR^5R^6$, $OC_{2-6}$alkyl$(SO_2)R^5$, $C_{0-6}$alkyl$(SO_2)R^5$, $C_{0-6}$alkyl$(SO)R^5$, $OC_{2-6}$alkyl$(SO)R^5$ and a 5- or 6-membered ring containing one or more atoms independently selected from the group consisting of C, N, O and S;

$R^5$ and $R^6$ are independently selected from, H, $C_{1-6}$alkyl, $C_{3-7}$cycloalkyl and aryl
and salts and hydrates thereof
m is selected from 1 or 2
p is selected from 0, 1, 2, 3 or 4
or a salt or hydrate thereof;
provided that the compound is not
1-(2-benzothiazolyl)-4-[[5-(5-methyl-2-furanyl)-2H-tetrazol-2-yl]acetyl-piperazine,
1-(4-acetylphenyl)-4-[[5-(5-methyl-2-furanyl)-2H-tetrazol-2-yl]acetyl]-piperazine, or 5-(5-methyl-2-furanyl)-N-(2-phenyl-2H-benzotriazol-5-yl)-2-acetamide.

2. A compound according to claim 1 wherein $X_3$ is N and $X_4$ is C.

3. A compound according to claim 1 wherein P is aryl.

4. A compound according to claim 3 wherein P is phenyl.

5. A compound according to claim 1 wherein $R^1$ is selected from halo, $C_{1-6}$alkyl, —$OC_{1-6}$alkyl, $C_{0-6}$alkylcyano.

6. A compound according to claim 5 wherein, $R^1$ is selected from Cl, F, cyano and methyl.

7. A compound according to claim 1 wherein $X^1$ is $CR^3R^4$.

8. A compound according to claim 7 wherein $X^2$ is selected from $CR^3R^4$, O, S and $NR^3$.

9. A compound according to claim 1 wherein Q is either selected from triazole and piperazine, or else Q is any other 4-, 5-, 6-, or 7-membered heterocyclic ring containing one or more heteroatoms selected from N, O and S and is fused to a triazole ring.

10. A compound according to claim 1 wherein Q is triazole.

11. A compound according to claim 1 wherein $X^2$ is a bond.

12. A compound according to claim 1 wherein Q is piperazine.

13. A compound according to claim 1 wherein Q is a 5-, 6-, or 7-membered heterocyclic ring, other than triazole or piperazine, and is fused to a triazole ring.

14. A compound according to claim 1 wherein $R^2$ is selected from the group consisting of $C_{1-6}$alkyl, $C_{1-6}$alkylhalo, $C_{3-7}$cylcoalkyl, $C_{0-6}$alkylaryl, $C_{0-6}$alkylheteroaryl, $O(CO)C_{1-4}$alkyl.

15. A compound according to claim 1 wherein $R^2$ is a 5- or 6-membered ring containing one or more atoms independently selected from C, N, O and S, which ring may optionally be fused with a 5- or 6-membered ring containing one or more atoms independently selected from the, group consisting of C, N and O and wherein said ring and said fused ring may be substituted by one or more A.

16. A compound according to claim 1 wherein A is selected from the group consisting of halo, —$OC_{1-6}$alkyl, $C_{0-6}NR^5R^6$, $C_{1-6}$alkylhalo.

17. A compound according to claim 1 selected from:
Ethyl 4-{[2-(3-chlorophenyl)-2H-tetrazol-5-yl]methyl}piperazine-1-carboxylate,
4-[2-(5-Chloro-2-fluoro-phenyl)-2H-tetrazol-5-ylmethyl]-piperazine-1-carboxylic acid ethyl ester,
4-(2-m-Tolyl-2H-tetrazol-5-ylmethyl)-piperazine-1-carboxylic acid ethyl ester,
4-[2-(3-Iodo-phenyl)-2H-tetrazol-5-ylmethyl]-piperazine-1-carboxylic acid ethyl ester,
4-[2-(3-Cyano-phenyl)-2H-tetrazol-5-ylmethyl]-piperazine-1-carboxylic acid ethyl ester,
4-[2-(2-Fluoro-5-methyl-phenyl)-2H-tetrazol-5-ylmethyl]-piperazine 1-carboxylic acid ethyl ester,
4-[5-({[2-(3-chlorophenyl)-2H-tetrazol-5-yl]methyl}thio)-4-cyclopropyl-4H-1,2,4-triazol-3-yl]pyridine,
4-[5-({1-[2-(3-chlorophenyl)-2H-tetrazol-5-yl]ethyl}thio)-4-cyclopropyl-4H-1,2,4-triazol-3-yl]pyridine,
Ethyl 4-{1-[2-(3-chlorophenyl)-2H-tetrazol-5-yl]ethyl}piperazine-1-carboxylate,
4-{5-[2-(5-Chloro-2-fluoro-phenyl)-2H-tetrazol-5-ylmethylsulfanyl]-4-methyl-4-H [1,2,4]triazol-3-yl}-pyridine,
4-{5-[2-(5-Chloro-2-fluoro-phenyl)-2H-tetrazol-5-ylmethylsulfanyl]-4-cyclopropyl-4H-[1,2,4]triazol-3-yl}-pyridine,
4-(5-{1-[2-(5-Chloro-2-fluoro-phenyl)-2H-tetrazol-5-yl]-ethylsulfanyl}-4-methyl-4H-[1,2,4]triazol-3-yl)-pyridine,
4-(5-{1-[2-(5-Chloro-2-fluoro-phenyl)-2H-tetrazol-5-yl]-ethylsulfanyl}-4-cyclopropyl-4H-[1,2,4]triazol-3-yl)-pyridine,
4-{1-[2-(5-Chloro-2-fluoro-phenyl)-2H-tetrazol-5-yl]-ethyl}-piperazine-1-carboxylic acid ethyl ester,
4-[4-Cyclopropyl-5-(2-m-tolyl-2H-tetrazol-5-ylmethylsulfanyl)-4H-[1,2,4]triazol-3-yl]-pyridine,
4-{4-Cyclopropyl-5-[1-(2-m-tolyl-2H-tetrazol-5-yl)-ethylsulfanyl]-4H-[1,2,4]triazol-3-yl}-pyridine,
4-{4-Methyl-5-[1-(2-m-tolyl-2H-tetrazol-5-yl)-ethylsulfanyl]-4H-[1,2,4]triazol-3-yl }-pyridine,
3-[5-(4-Cyclopropyl-5-pyridin-4-yl-4H-[1,2,4]triazol-3-ylsulfanylmethyl)-tetrazol-2-yl]-benzonitrile,
3-{5-[1-(4-Cyclopropyl-5-pyridin-4-yl-4H-[1,2,4]triazol-3-ylsulfanyl)-ethyl]-tetrazol-2-yl}-benzonitrile
3-{5-[1-(4-Methyl-5-pyridin-4-yl-4H-[1,2,4]triazol-3-ylsulfanyl)-ethyl]-tetrazol-2-yl}-benzonitrile4-{4-Cyclopropyl-5-[2-(2-fluoro-5-methyl-phenyl)-2H-tetrazol-5-ylmethylsulfanyl]-4H-[1,2,4]triazol-3-yl}-pyridine,
4-(4-Cyclopropyl-5-{1-[2-(2-fluoro-5-methyl-plenyl)-2H-tetrazol-5-yl]-ethylsulfanyl}-4H-[1,2,4]triazol-3-yl)-pyridine,
4-(5-{1-[2-(2-Fluoro-5-methyl-phenyl)-2H-tetrazol-5-yl]-ethylsulfanyl}-4-methyl-4H-[1,2,4]triazol-3-yl)-pyridine,
Methyl-(4-methyl-5-pyridin-4-yl-4H-[1,2,4]triazol-3-yl)-(2-m-tolyl-2H-tetrazol-5-ylmethyl)-amine,
Methyl-(4-methyl-5-pyridin-4-yl-4H-[1,2,4]triazol-3-yl)-[1-(2-m-tolyl-2H-tetrazol-5-yl)-ethyl]-amine,
[2-(3-Chloro-phenyl)-2H-tetrazol-5-ylmethyl]-methyl-(4-methyl-5-pyridin-4-yl-4H-[1,2,4]triazol-3-yl)-amine,
{1-[2-(3-Chloro-phenyl)-2H-tetrazol-5-yl]-ethyl}-methyl-(4-methyl-5-pyridin-4-yl-4H-[1,2,4]triazol-3-yl)-amine,
[2-(2-Fluoro-5-methyl-phenyl)-2H-tetrazol-5'-ylmethyl]-methyl-(4-methyl-5-pyridin-4-yl-4H-[1,2,4]triazol-3-yl)-amine,
{1-[2-(2-Fluoro-5-methyl-phenyl)-2H-tetrazol-5-yl]-ethyl}-methyl-(4-methyl-5-pyridin-4-yl-4H-[1,2,4]triazol-3-yl)-amine,
[2-(3-Iodo-phenyl)-2H-tetrazol-5-ylmethyl]-methyl-(4-methyl5-pyridin-4-yl-4H-[1,2,4]triazol-3-yl)-amine,
{1-[2-(3-Iodo-phenyl)-2H-tetrazol-5-yl]-ethyl}-methyl-(4-methyl-5-pyridin-4-yl-4H-[1,2,4]triazol-3-yl)-amine,
Methyl-(4-methyl-5-pyridin-4-yl-4H-[1,2,4]triazol-3-yl)-(2-m-tolyl-2H-tetrazol-5-ylmethyl)-amine,
Methyl-(4-methyl-5-pyridin-4-yl-4H-[1,2,4]triazol-3-yl)-[1-(2-m-tolyl-2H-tetrazol-5-yl)-ethyl]-amine,
[2-(3-Chloro-phenyl)-2H-tetrazol-5-ylmethyl]-methyl-(4-methyl-5-pyridin-4-yl-4H-[1,2,4]triazol-3-yl)-amine,
{1-[2-(3-Chloro-phenyl)-2H-tetrazol-5-yl]-ethyl}-methyl-(4-methyl-5-pyridin-4-yl-4H-[1,2,4]triazol-3-yl)-amine,
[2-(2-Fluoro-5-methyl-phenyl)-2H-tetrazol-5-ylmethyl]-methyl-(4-methyl-5-pyridin-4yl -4H-[1,2,4]triazol-3-yl)-amine,
{1-[2-(2-Fluoro-5-methyl-phenyl)-2H-tetrazol-5-yl]-ethyl}-methyl-(4-methyl-5-pyridin-4-yl-4H-[1,2,4]triazol-3-yl)-amine, 8-{1-]2-(3-Iodo-phenyl)-2H-tetrazol-5-yl]-ethyl}-3-pyridin-4-yl-5,6,7,8-tetrahydro -[1,2,4]triazolo[4,3-a]pyrimidine,
8-{1-]2-(3-Iodo-phenyl)-2H-tetrazol-5-yl]-ethyl}-3-pyridin-4-yl-5,6,7,8-tetrahydro -[1,2,4]triazolo[4,3-a]pyrimidine,
3-Pyridin-4-yl-8-(2-m-tolyl-2H-tetrazol-5-yl methyl)-5,6,7,8-tetrahydro-4H-1,2,3a, 8-tetraaza-azulene,
3-Pyridin-4-yl-8-[1-(2-m-tolyl-2H-tetrazol-5-yl)-ethyl]-5,6,7,8-tetrahydro-4H-1,2,3a, 8-tetraaza-azulene,
8-[2-(3-Chloro-phenyl)-2H-tetrazol-5-ylmethyl]-3-pyridin-4-yl-5,6,7,8-tetrahydro-4H-1,2,3a, 8-tetraaza-azulene,
8-{1-(2-(3-Chloro-phenyl)-2H-tetrazol-5-yl]-ethyl}-3-pyridin-4-yl-5,6,7,8-tetrahydro-4H-1,2,3a, 8-tetraaza-azulene,
8-[2-(2-Fluoro-5-methyl-phenyl)-2H-tetrazol-5-ylmethyl]-3-pyridin-4-yl-5,6,7,8-tetrahydro-4H-1,2,3a, 8-tetraaza-azulene,
8-{1-[2-(2-Fluoro-5-methyl-phenyl)-2H-tetrazol-5-yl]-ethyl}-3-pyridin-4-yl5,6,7,8-tetra-hydro-4H-1,2,3a, 8-tetraaza-azulene,
8-[2-(3-Iodo-phenyl)-2H-tetrazol-5-ylmethyl]-3-pyridin-4-yl-5,6,7,8-tetrahydro-4H -1,2,3a,8-tetraaza-azulene,
8-{1-[2-(3-Iodo-phenyl)-2H-tetrazol-5-yl]-ethyl}-3-pyridin-4-yl-5,6,7,8-tetrahydro-4H-1,2,3a,8-tetraaza-azulene,
4-(5-{[2-(3-chlorophenyl)-2H-tetrazol-5-yl]methoxy}-4-methyl-4H-1,2,4-triazol-3-yl)pyridine,
4-(5-{1-[2-(3-chlorophenyl)-2H-tetrazol-5-yl]ethoxy}-4-methyl-4H-1,2,4-triazol-3-yl)pyridine,
4-[4-Methyl-5-(2-m-tolyl-2H-tetrazol-5-ylmethoxy)-4H-[1,2,4]triazol-3-yl]-pyridine,
4-{4-Methyl-5-[1-(2-m-tolyl-2H-tetrazol-5-yl)-ethoxy]-4H-[1,2,4]triazol-3-yl }-pyridine,
4-{5-[2-(2-Fluoro-5-methyl-phenyl)-2H-tetrazol-5-ylmethoxy]-4-methyl-4H-[1,2,4]triazol-3-yl}-pyridine,
4-(5-{1-[2-(2-Fluoro-5-methyl-phenyl)-2H-tetrazol-5-yl]-ethoxy}-4-methyl-4H-[1,2,4]triazol-3-yl)-pyridine,
4-{5-[2-(3-Chloro-phenyl)-2H-tetrazol-5-ylmethoxy]-4-cyclopropyl-4H-[1,2,4]triazol-3-yl}-pyridine,
4-(5-{1-[2-(3-Chloro-phenyl)-2H-tetrazol-5-yl]-ethoxy}-4-cyclopropyl-4H-[1,2,4]triazol-3-yl)-pyridine,
4-[4-Cyclopropyl-5-(2-m-tolyl-2H-tetrazol-5-ylmethoxy)-4H-(1,2,4]triazol-3-yl-]-pyridine,
4-{4-Cyclopropyl-5-[1-(2-m-tolyl-2H-tetrazol-5-yl)-ethoxy]-4H-[1,2,4]triazol-3-yl}-pyridine,
4-{4-Cyclopropyl-5-[2-(2-fluoro-5-methyl-phenyl)-2H-tetrazol5-ylmethoxyl4H-[1,2,4]triazol-3-yl) -pyridine,
4-(4-Cyclopropyl-5-{1-[2-(2-fluoro-5-methyl-phenyl)-2H-tetrazol-5-yl]-ethoxy)-4H-[1,2,4]triazol-3-yl)-pyridine,
4-{5-[2-(3-iodo-phenyl)-2H-tetrazol-5-yl methoxy]-4-methyl-4H-[1,2,4]triazol-3-yl}-pyridine,
4-(5-(1-[2-(3-iodo-phenyl)-2H-tetrazol-5-yl]-ethoxy}-4-methyl-4H-[1,2,4]triazol-3-yl)-pyridine,
4-{4-Cyclopropyl-5-[2-(3-iodo-phenyl)-2H-tetrazol-5-ylmethoxy]-4H-[1,2,4]triazol-3-yl }-pyridine,
4-(4-Cyclopropyl-5-{1-[2-(3-iodo-phenyl)-2H-tetrazol-5-yl]-ethoxy}-4H-[1,2,4]triazol-3-yl)-pyridine,
3-[5-(4-Methyl-5-pyridin-4-yl-4H-[1,2,4]triazol-3-yloxymethyl)-tetrazol-2-yl]-benzonitrile,
3-{5-[1-(4-Methyl-5-pyridin-4-yl-4H-[1,2,4]triazol-3-yloxy)-ethyl]-tetrazol-2-yl}-benzonitrile,
3-[5-(4-Cyclopropyl-5-pyridin-4-yl-4H-[1,2,4]triazol-3-yloxymethyl)-tetrazol-2-yl]-benzonitrile,
3-{5-[1-(4-Cyclopropyl-5-pyridin-4-yl-4H-[1,2,4]triazol-3-yloxy)-ethyl]-tetrazol-2-yl}-benzonitrile,
3-(5-{[Methyl-(4-methyl-5-pyridin-4-yl-4H-[1,2,4]triazol-3-yl)-amino]-methyl}-tetrazol-2-yl)-benzonitrile,
3-(5-{1-[Methyl-(4-methyl-5-pyridin-4-yl-4H-[1,2,4] triazol-3-yl)-amino]-ethyl}-tetrazol-2-yl)-benzonitrile,
3-[5-(3-Pyridin-4-yl-6,7-dihydro-5H-[1,2,4]triazolo[4,3-a]pyrimidin-8-ylmethyl)-tetrazol-2-yl]-benzonitrile,
3-{5-[1-(3-Pyridin-4-yl-6,7-dihydro-5H-[1,2,4]triazolo[4,3-a]pyrimidin-8-yl)-ethyl)-tetrazol-2-yl }-benzonitrile,
3-[5-(3-Pyridin-4-yl-4,5,6,7-tetrahydro- 1,2,3a,8-tetraaza-azulen-8-ylmethyl)-tetrazol-2-yl]-benzonitrile,
3-{5-[1-(3-Pyridin-4-yl-4,5,6,7-tetrahydro-1,2,3a,8-tetraaza-azulen-8-yl)-ethyl]-tetrazol-2-yl }-benzonitrile,
(R) & (S)-4-(5-{1-[2-(3-chlorophenyl)-2H-tetrazol-5-yl]ethoxy}-4-methyl-4H- 1,2,4-triazol-3-yl)pyridine,
2-(3-chloro-phenyl)-5-[(triphenyl-$\lambda^5$-phosphanyl)-methyl]-2H-tetrazole hydrobromide,
4-(5-{2-[2-(3-chloro-phenyl)-2H-tetrazol-5-yl]-vinyl}-4-ethyl-4H-[1,2,4]triazol-3-yl)-pyridine,
1-[2-(3-Chloro-phenyl)-2H-tetrazol-5-yl]-2-(4-cyclopropyl-5-pyridin-4-yl-4H-[1,2,4]triazol-3-yl)-ethanol,
2-[2-(3-Chloro-phenyl)-2H-tetrazol-5-yl]-1-(4-cyclopropyl-5-pyridin-4-yl-4H-[1,2,4]triazol-3-yl)-ethanol,
4-(5-{2-[2-(3-chloro-phenyl)-2H-tetrazol-5-yl]-vinyl}-4-ethyl-4H-[1,2,4]triazol-3-yl)-pyridine,
3-[4-Methyl-5-({[2-(3-methylphenyl)-2H-tetrazol-5-yl]methyl}thio)-4H-1,2,4-triazol-3-yl]benzonitrile,
5-({[5-(3,5-Difluorophenyl)-4-ethyl-4H-1,2,4-triazol-3-yl]thio}methyl)-2-(3-methylphenyl)-2H-tetrazole,
3-[4-Methyl-5-({1-[2-(3-methylphenyl)-2H-tetrazol-5-yl]ethyl)thio)-4H-1,2,4-triazol-3-yl]benzonitrile,
5-(1-{[5-(3,5-Difluorophenyl)-4-ethyl-4H-1,2,4-triazol-3-yl]thio}ethyl)-2-(3-methylphenyl)-2H-tetrazole,
6-(4-{1-[2-(3-Chlorophenyl)-2H-tetrazol-5-yl]ethyl}piperazin-1-yl)nicotinonitrile,
3-(4-{1-[2-(3-Chlorophenyl)-2H-tetrazol-5-yl]ethyl}piperazin-1-yl)pyrazine-2-carbonitrile,
2-(4-{1-[2-(3-Chlorophenyl)-2H-tetrazol-5-yl]ethyl}piperazin-1-yl)nicotinonitrile,
1-{1-[2-(3-Chlorophenyl)-2H-tetrazol-5-yl]ethyl}-4-(3-nitropyridin-2-yl)piperazine,
8-{1-[2-(3-Chlorophenyl)-2H-tetrazol-5-yl]ethyl}-3-(3,5-difluorophenyl)-5,6,7,8-tetrahydro[1,2,4]triazolo[4,3-a]pyrimidine,
8-{1-[2-(3-Chlorophenyl)-2H-tetrazol-5-yl]ethyl-}-3-(4-methoxyphenyl)-5,6,7,8-tetrahydro[1,2,4]triazolo[4,3-a]pyrimidine,
3-(2-Chloro-6-methoxypyridin-4-yl)-8-{1-[2-(3-chlorophenyl)-2H-tetrazol-5-yl]ethyl}-5,6,7,8-tetrahydro[1,2,4]triazolo[4,3-a]pyrimidine,
8-{1-[2-(3-Chlorophenyl)-2H-tetrazol-5-yl]ethyl}-3-(2-methoxypyridin-4-yl)-5,6,7,8-tetrahydro[1,2,4]triazolo[4,3-a]pyrimidine,
8-{[2-(3-Chlorophenyl)-2H-tetrazol-5-yl]methyl}-3-(2-methoxypyridin-4-yl)-5,6,7,8-tetrahydro[1,2,4]triazolo[4,3-a]pyrimidine,
3-(5-{[3-(2-Methoxypyridin-4-yl)-6,7-dihydro[1,2,4]triazolo[4,3-a]pyrimidine-8(5H)-yl]methyl}-2H-tetrazol-2-yl)benzonitrile,
3-(2-Methoxypyridin-4-yl)-8-{1-[2-(3-iodophenyl)-2H-tetrazol-5-yl]ethyl}-5,6,7,8-tetrahydro[1,2,4]triazolo[4,3-a]pyrimidine,
3-(5-{1-[3-(2-Methoxypyridin-4-yl)-6,7-dihydro[1,2,4]triazolo[4,3-a]pyrimidin-8(5H)-yl]ethyl}-2H-tetrazol-2-yl)benzonitrile, 3(5-{[3-(2-Methoxypyridin-4-yl)-5,6,7,8-tetrahydro-9H-[1,2,4]triazolo[4,3-a][1,3]diazepin-9-yl]methyl}-2H-tetrazol-2-yl)benzonitrile, 3-(5-{[3-(2,6-Dimethoxypyrimidin-4-yl)-6,7-dihydro[1,2,4]triazolo[4,3-a]pyrimidin-8(5H)-yl]methyl}-2H-tetrazol-2-yl)benzonitrile, (R) 3-(5-(1-[3-(2-Methoxypyridin-4-yl)-6,7-dihydro[1,2,4]triazolo]4,3-a]pyrimidin-8(5H)-yl]ethyl}-2H-tetrazol-2-yl)benzonitrile, (S) 3-(5-(1-[3-(2-Methoxypyridin-4-yl)-6,7-dihydro [1,2,4]triazolo[4,3-a]pyrimidin-8(5H)-yl]ethyl}-2H-tetrazol-2-yl)berizonitrile, (R) Ethyl 4-{1-[2-(3-chlorophenyl)-2H-tetrazol-5-yl]ethyl)piperazine-1-carboxylate, (S) Ethyl 4-{1-[2-(3-chlorophenyl)-2H-tetrazol-5-yl]ethyl}piperazine-1-carboxylate, (R) Ethyl 4-{1-[2-(5-chloro-2-fluorophenyl)-2H-tetrazol-5-yl]ethyl}piperazine-1-carboxylate, (S) Ethyl 4-{1-[2-(5-chloro-2-fluorophenyl)-2H-tetrazol-5-yl]ethyl}piperazine-1-carboxylate, (R) 6-(4-{1-[2-(3-Chlorophenyl)-2H-tetrazol-5-yl]ethyl}piperazin-1-yl)nicotinonitrile, (S) 6-(4-{1-[2-(3-Chlorophenyl)-2H-tetrazol-5-yl]ethyl}piperazin-1-yl)nicotinonitrile, (R) 3-(4-{1-[2-(3-Chlorophenyl)-2H-tetrazol-5-yl]ethyl}piperazin- 1-yl)pyrazine-2-carbonitrile (S) 3-(4-{1-[2-(3-Chlorophenyl)-2H-tetrazol-5-yl]ethyl}piperazin-1-yl)pyrazine-2-carbonitrile, 4-(5-{(S)-1-[2-(3-Chloro-phenyl)-2H-tetrazol-5-yl]-ethoxy}-4-methyl-4H-[1,2,4]triazol-3-yl)-pyridine, 2-(3-Chloro-phenyl)-5-{(R)-1-[5-(3,5-difluoro-phenyl)-4-methyl-4H-(1,2,4]triazol-3-yloxy]-ethyl)-2H-tetrazole, 3-(5-{(R)-1-[2-(3-Chloro-phenyl)-2H-tetrazol-5-yl]-ethoxy}-4-methyl-4H-[1,2,4]triazol-3-yl)-pyridine, 4-(5-{2-[5-(3-Chlorophenyl)-2H-tetrazol-2-yl]propyl}-4-methyl-4H- 1,2,4-triazol-3-yl)pyridine, 4-(5-{(R)-1-[2-(3-Chloro-phenyl)-2H-tetrazol-5-yl]-ethoxy}-4-methyl-4H-[1,2,4]triazol-3-yl)-pyridine, 2-(3-chlorophenyl)-5-[1-methyl-2-phenylvinyl]-2H-tetrazole, and 2-({1-[2-(3-chlorophenyl)-2H-tetrazol-5-yl)ethyl}thio)-imidazo[4,5-b]pyridine.

18. A pharmaceutical composition comprising as active ingredient a therapeutically effective, amount of the compound of claim 1, in association with one or more of a pharmaceutically acceptable diluent, excipient and/or inert carrier.

19. A compound according to claim 4 wherein $R^1$ is selected from halo, $C_{1-6}$alkyl, —$OC_{1-6}$alkyl, $C_{0-6}$alkylcyano.

20. A compound according to claim 19 wherein Q is triazole or piperazine.

21. A compound according to claim 20 wherein $R^2$ is selected from the group consisting of $C_{1-6}$alkyl, $C_{1-6}$alkylhalo, $C_{3-7}$cylcoalkyl, $C_{0-6}$alkylaryl, $C_{0-6}$alkylheteroaryl, and $O(CO)C_{1-4}$alkyl.

22. A compound according to claim 21 wherein $R^2$ is pyridine.

\* \* \* \* \*